(12) United States Patent
Egorov et al.

(10) Patent No.: US 9,173,946 B2
(45) Date of Patent: Nov. 3, 2015

(54) BIFUNCTIONAL HYDROXY-BISPHOSPHONIC ACID DERIVATIVES

(75) Inventors: Maxim Egorov, Bouguenais (FR); Jean-Yves Goujon, Derval (FR); Ronan Le Bot, Nantes (FR)

(73) Assignee: ATLANTHERA, Saint Herblain (FR)

( * ) Notice: Subject to any disclaimer, the term of this patent is extended or adjusted under 35 U.S.C. 154(b) by 19 days.

(21) Appl. No.: 14/008,986

(22) PCT Filed: Mar. 28, 2012

(86) PCT No.: PCT/EP2012/055569
§ 371 (c)(1),
(2), (4) Date: Dec. 2, 2013

(87) PCT Pub. No.: WO2012/130911
PCT Pub. Date: Oct. 4, 2012

(65) Prior Publication Data
US 2014/0086843 A1     Mar. 27, 2014

(30) Foreign Application Priority Data
Mar. 28, 2011 (FR) .................................. 11 52546

(51) Int. Cl.
| | | |
|---|---|---|
| *A61K 31/663* | (2006.01) | |
| *A61K 47/48* | (2006.01) | |
| *C07F 9/38* | (2006.01) | |
| *C07F 9/6509* | (2006.01) | |
| *C07F 9/655* | (2006.01) | |
| *C07F 9/6561* | (2006.01) | |
| *A61K 31/662* | (2006.01) | |
| *A61K 49/00* | (2006.01) | |

(52) U.S. Cl.
CPC ......... *A61K 47/48084* (2013.01); *A61K 31/662* (2013.01); *A61K 49/0052* (2013.01); *C07F 9/3869* (2013.01); *C07F 9/3873* (2013.01); *C07F 9/6552* (2013.01); *C07F 9/6561* (2013.01); *C07F 9/65517* (2013.01); *C07F 9/65522* (2013.01); *C07F 9/650958* (2013.01)

(58) Field of Classification Search
CPC . A61K 31/663; A61K 31/664; A61K 31/675; A61K 47/48; A61K 49/00; C07F 9/38; C07F 9/28
USPC ........................................................ 424/9.6
See application file for complete search history.

(56) References Cited

U.S. PATENT DOCUMENTS 5,036,058 A     7/1991  Jaeggi
2010/0311695 A1*  12/2010  Egorov et al. ................. 514/107

FOREIGN PATENT DOCUMENTS

| EP | 0 387 194 A1 | 9/1990 |
| FR | 2 296 080 A1 | 7/2009 |
| WO | WO 2009/083614 A1 | 7/2009 |

OTHER PUBLICATIONS

PCT/ISA/210—International Search Report for PCT/EP2012/055569 dated May 22, 2012.
PCT/ISA/237—Written Opinion of the International Searching Authority for PCT/EP2012/055569 dated May 22, 2012.
Heymann et al., "Bisphosphonates: New Therapeutic Agents for the Treatment of Bone Tumors", Trends in Molecular Medicine, vol. 10, No. 7 (2004) pp. 337-343.
Manolagas, "Birth and Death of Bone Cells; Basic Regulatory Mechanisms and Implications for the Pathogenesis and Treatment of Osteoporosis", Endocrine Reviews, vol. 21 (2000) pp. 115-137.
Ory et al., "Zoledronic Acid Suppresses Lung Metastases and Prolongs Overall Survival of Osteosarcoma-Bearing Mice", Cancer, vol. 104 (2005) pp. 2522-2529.
Owen et al., "New Developments in Bone Formation", Current Opinion in Nephrology and Hypertension, vol. 7 (1998) pp. 363-366.
Roodman, "Advances in Bone Biology: The Osteoclast", Endocrine Reviews, vol. 17 (1996) pp. 308-332.
Zhao et al., "Novel Prodrugs of SN38 Using Multiarm Poly(ethylene glycol) Linkers", Bioconjugate Chem., vol. 19 (2008) pp. 849-859.

* cited by examiner

*Primary Examiner* — Michael G Hartley
*Assistant Examiner* — Jagadishwar Samala
(74) *Attorney, Agent, or Firm* — Birch, Stewart, Kolasch & Birch, LLP

(57) ABSTRACT

The present invention relates to a bifunctional hydroxy-bisphosphonic acid derivative of formula (I) below:

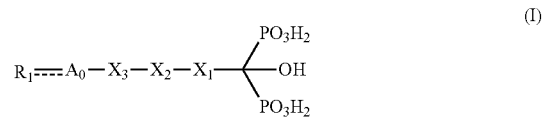

or a pharmaceutically-acceptable salt thereof,
a method for producing the same, pharmaceutical compositions containing the same,
and the use thereof as a medicament,
as well as a compound of formula (II) below:

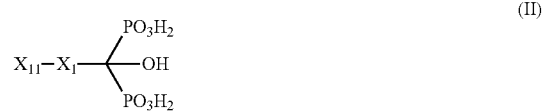

or a pharmaceutically-acceptable salt thereof,
and the use thereof for producing a vectorized molecule of therapeutic or diagnostic purpose.

19 Claims, 6 Drawing Sheets

BIFUNCTIONAL HYDROXY-BISPHOSPHONIC ACID DERIVATIVES

The present invention relates to bifunctional hydroxy-bisphosphonic acid derivatives, the synthesis method thereof, pharmaceutical compositions containing them, and their use as a medicament as well as vectorization of molecules of therapeutic or diagnostic interest by a vector targeting bone tissue.

Bone tissue is a connective tissue composed of a mineral fraction consisting of calcium phosphate in the form of hydroxyapatite crystals ($Ca_{10}(PO_4)_6(OH)_2$) and an organic fraction containing an extracellular matrix of specialized cells.

Bone tissue is continuously rearranged via a process called bone remodeling. It is characterized by a building phase due to the activity of osteoblasts, synthesizing a new organic matrix and causing it to be mineralized (Owen et al., Curr. Opin. Nephrol. Hypertens. 1998, 7, 363) and a degradation phase induced by osteoclasts that resorb the organic matrix and dissolve the mineral (Roodman et al., Endocr. Rev. 1996, 17, 308). This physiological process allows maintaining calcium and phosphate homeostasis and bone mass (Manologas et al., Endocriv. Rev. 2000, 21, 115) and adapting to mechanical stress. Any disruption of this equilibrium is related to the appearance of osteocondensing diseases, such as osteopetrosis or, more often, osteolysis, possibly tumor induced (with primary tumors, such as osteosarcoma, or secondary tumors, such as bone metastases), or non-tumor induced, in the case of metabolic diseases such as osteoporosis.

Bisphosphonates (basic form of bisphosphonic acid derivatives, including hydroxy-bisphosphonic acid derivatives) are synthetic analogs of endogenous pyrophosphates for which the P—O—P chain has been replaced by a P—C—P chain, leading to stable metabolic compounds that represent an effective tool for osteolysis (Heymann et al., Trends Mol. Med., 2004, 10, 337).

These molecules are primarily used for their ability to target bone tissue. Like pyrophosphates, bisphosphonates have a strong affinity for the mineral component of bone (affinity between phosphate groups and the calcium of the mineral component of bone) and at high doses can modulate the calcification process. These substances have proven useful for the treatment of various bone metabolism disorders. Bisphosphonates are particularly used to treat pathologies involving excessive bone resorption leading, on the one hand to hypercalcemia, and on the other hand, to bone damage that cause pain and fractures.

Thus, their use is necessary for about a decade for treatment of osteoporosis, tumor-induced or non-tumor induced hypercalcemia, and for osteolytic tumor pathologies such as multiple myeloma or bone metastases secondary to prostate or breast carcinoma.

Structure-activity studies developed to date have clearly shown that the ability of bisphosphonates to inhibit bone resorption depends on two structural factors:

phosphonate groups (and hydroxyl in the case of hydroxy-bisphosphonates), essential for a good affinity of the compound with the mineral component of bone, the RES side chain, specific for a molecular target, which determines the biological activity associated with the molecule.

Hydroxy-biphosphonate derivative:

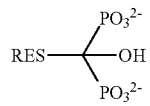

Patent application FR 2 926 081 describes notably bifunctional hydroxy-bisphosphonic acid derivatives comprising an active ingredient bound to a hydroxy-bisphosphonic acid function by means of a spacer arm, thus enabling bone tissue to be targeted. However, these derivatives are prepared from the active ingredient itself by progressive construction of the spacer arm. This method is therefore not economical and leads to the loss of large amounts of active ingredient, a product having always a high cost.

Therefore the inventors developed novel bifunctional hydroxy-bisphosphonic acid derivatives that can be synthesized by simple grafting of the spacer arm comprising the hydroxy-bisphosphonic function onto the optionally functionalized active ingredient. In the present invention, the optionally functionalized active ingredient is bound to the spacer arm by means of an imine function, thus enabling bifunctional hydroxy-bisphosphonic acids to be prepared in a simpler and more economical way, while preserving the therapeutic or diagnostic activity of these derivatives.

The present invention concerns bifunctional hydroxy-bisphosphonic acid derivatives having general formula (I) below:

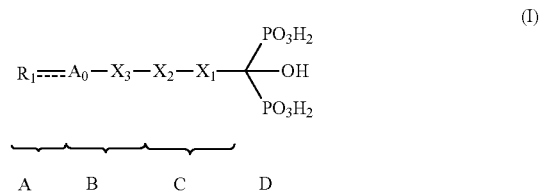

for which:
  ==== $A_0$ represents a single bond, $A_0$ then being absent, or a =N or =$CR_0$ group,
  $A_0$ then representing N or $CR_0$, with $R_0$=H or ($C_1$-$C_6$)-alkyl,
  $R_1$ represents a residue of a molecule of therapeutic or diagnostic interest,
  $X_1$ represents an —$X_4$-$A_1$-$(CH_2)_n$-$A_2$-$(CH_2)_m$— chain ($X_4$ being bound to $X_2$),
  $X_2$ represents an imine function (—C=N— or —N=C—),
  $X_3$ represents a single bond or a ($C_1$-$C_{20}$)-alkyl chain, especially ($C_1$-$C_{15}$)-alkyl, in particular ($C_1$-$C_{10}$)-alkyl, and preferably ($C_1$-$C_4$)-alkyl, optionally broken up and/or followed and/or replaced by one or more moieties chosen from the group consisting of aryl, heteroaryl, cycloalkyl, heterocyclic, —C=C—, —C($R_7$)=C($R_3$)—, —O—, —S—, —$NR_9$—, —C(O)—, —C(S)—, —C=N—, —N=C—, —C=C—, —C≡C—, —OC(O)—, —C(O)O—, —SC(O)—, —C(O)S—, —N($R_{10}$)C(O)— and —C(O)N($R_{11}$)— groups, the aryl, heteroaryl and heterocyclic rings being optionally substituted,
  $X_4$ represents a single bond or an optionally substituted aryl or heteroaryl group, $A_1$ represents a single bond, O, S, $NR_{27}$, —C(O)—, —C(S)—, —C=N—, —N=C—, —C=C—, —C≡C—, —OC(O)—, —C(O)O—, —SC(O)—, —C(O)S—, —N($R_{28}$)C(O)— or —C(O)N($R_{29}$)—, $A_2$ represents a single bond, O, S, $NR_{30}$, —C(O)—, —C(S)—, —C=N—, —N=C—, —C=C—, —C≡C—, —OC(O)—, —C(O)O—, —SC(O)—, —C(O)S—, —N($R_{31}$)C(O)—, —C(O)N($R_{32}$)—, —O—($CH_2CH_2O)_k$— or a -$A_9$-$(CH_2)_a$-$A_{10}$-$(CH_2)_b$-$A_{11}$- group, $A_9$ and $A_{11}$ each represent, independently of one another, O, S or $NR_{38}$, $A_{10}$ represents an aryl, heteroaryl or heterocyclic group, n represents a whole number comprised between 0 and 5, particularly between 1 and 5, and especially 3, m represents a whole number comprised between 0 and 5, particularly between 1 and 5, and especially 2, k represents a whole number comprised between 1 and 10, especially between 1 and 5, a and b each represent, independently of one another, a whole number comprised between 0 and 5, $R_7$ and $R_8$ represent, independently of one another, a hydrogen atom or a ($C_1$-$C_6$) alkyl group.

$R_9$ to $R_{11}$ represent, independently of one another, a hydrogen atom or a $C_1$-$C_6$ alkyl, cycloalkyl, heterocyclic, aryl, heteroaryl or acyl group, and preferably a hydrogen atom or a ($C_1$-$C_6$) alkyl or aryl group, and still more preferably a hydrogen atom or a ($C_1$-$C_6$) alkyl group, $R_{27}$ and $R_{29}$ represent, independently of one another, a hydrogen atom or a ($C_1$-$C_6$) alkyl group, and $R_{30}$ to $R_{32}$ and $R_{38}$ represent, independently of one another, a hydrogen atom or a $C_1$-$C_6$ alkyl, cycloalkyl, heterocyclic, aryl, heteroaryl or acyl group, and preferably a hydrogen atom or a ($C_1$-$C_6$) alkyl or aryl group, and still more preferably a hydrogen atom or a ($C_1$-$C_6$) alkyl group such as methyl, or pharmaceutically-acceptable salts thereof.

The molecules of the invention are therefore composed of three separate parts:

a part D corresponding to the hydroxy-bisphosphonic acid function that will allow the molecule to target bone tissue due to the strong affinity of this function for the mineral component of bone, a part C that is a spacer arm, onto which residue $R_1$ can be grafted, a part B that is a linker for grafting residue $R_1$ onto the spacer arm, and finally a part A corresponding to residue $R_1$ of a molecule with therapeutic or diagnostic activity, notably enabling a targeted treatment of a bone tissue disease or even a diagnosis, especially for imaging this bone tissue.

In the present invention, "residue of a molecule of therapeutic or diagnostic interest" means the residue obtained when the molecule of therapeutic or diagnostic interest is bound to the rest of the molecule, and in particular to spacer arm B. Thus, the molecule of therapeutic or diagnostic interest must include or must be modified so a functional group allows binding with the spacer arm, such as a —OH, —SH, —NH, —$NH_2$, C=O, —CHO, —COOH or —$CONH_2$ group. Note that when ==== $A_0$ represents a =N group, the residue will advantageously have a C=O or —CHO function that can react with an amine function of the linker to form the =N group. When ==== $A_0$ represents a, =$CR_0$, group, the double bond will advantageously be linked to a nitrogen atom present on $R_1$ to give an imine function. Thus, the residue will advantageously have an amine function that can react with a C=O or —CHO function of the linker to form the group or =$CR_0$.

In the present invention, "alkyl" group means a saturated, linear or branched hydrocarbon chain.

In the present invention, "($C_1$-$C_6$)alkyl" means an alkyl group such as defined above, containing 1 to 6 carbon atoms, such as, for example, methyl, ethyl, isopropyl, tert-butyl, pentyl, etc.

In the present invention, "($C_1$-$C_{20}$)alkyl, especially ($C_1$-$C_{15}$)-alkyl, in particular ($C_1$-$C_{10}$)-alkyl, and preferably ($C_1$-$C_4$)-alkyl", means an alkyl group such as defined above, respectively containing 1 to 20 carbon atoms, especially 1 to 15, in particular 1 to 10 and preferably 1 to 4 carbon atoms, such as, for example, methyl, ethyl, isopropyl, tert-butyl, pentyl, hexyl, decyl, etc.

In the present invention, "aryl" means an aromatic group, especially containing 6 to 20 carbon atoms, preferably 6 to 10 carbon atoms, and comprising one or more fused rings, such as, for example, a phenyl or naphthyl group. Advantageously, it is a phenyl group.

In the present invention, "heteroaryl" means an aromatic group comprising one or more fused rings and comprising 5 to 10 cyclic atoms, including one or more heteroatoms, advantageously 1 to 4 and even more advantageously 1 or 2, such as, for example, sulfur, nitrogen, oxygen, phosphorus or selenium atoms, and preferably sulfur, nitrogen or oxygen, the other cyclic atoms being carbon atoms, Examples of heteroaryl groups are furyl, thienyl, pyrrolyl, pyridinyl, pyrimidinyl, pyrazolyl, imidazolyl, triazolyl, tetrazolyl indyl or selenophenyl.

In the present invention, "cycloalkyl" means a saturated mono- or polycyclic hydrocarbon chain (especially a bicyclic or tricyclic chain) containing 3 to 10 cyclic carbon atoms. When it is a polycyclic group, the rings can be fused, bridged or joined by a spiro ring junction two by two. Examples include cyclopropyl, cyclopentyl, cyclohexyl and cycloheptyl groups.

In the present invention, "heterocyclic" group means a 5 to 10-membered ring, saturated or unsaturated, but not aromatic, and containing one or more, advantageously 1 to 4, more advantageously 1 or 2 heteroatoms, such as, for example, sulfur, nitrogen or oxygen atoms. It can particularly be a pyrrolidinyl, piperidinyl, piperazinyl or morpholinyl group.

The aryl, heteroaryl and heterocyclic group, when substituted, can be with substituted one or more groups chosen from the group consisting of a halogen atom, $NO_2$, —CN, —OH, —SH, —$NR_{12}R_{13}$, —$B(OH)_2$, —$SO_3R_{14}$, —$COOR_{15}$, —C(O)ON$R_{16}R_{17}$, —OPH(O)O$R_{18}$, —PH(O)O$R_{19}$, —OP(O)(O$R_{20}$)(O$R_{21}$), —P(O)(O$R_{22}$)(O$R_{23}$), —C(O)$R_{24}$, —P$R_{25}R_{26}$, ($C_1$-$C_6$) alkyl and ($C_1$-$C_6$) alkoxy, with $R_{12}$ to $R_{24}$ representing, independently of one another, a hydrogen atom or a ($C_1$-$C_6$)alkyl group and $R_{25}$ and $R_{26}$ representing, independently of one another, a ($C_1$-$C_6$)alkyl group.

In the present invention "halogen atom" means fluorine, chlorine, bromine and iodine atoms.

In the present invention, "($C_1$-$C_6$)alkoxy" means a ($C_1$-$C_6$) alkyl group as defined above, bound to the rest of the molecule by an oxygen atom. Examples include methoxy, ethoxy, propoxy, isopropoxy, butoxy or tert-butoxy groups, and especially methoxy groups.

In the present invention, "acyl" group means a $C_1$-$C_6$) alkyl, cycloalkyl, heterocyclic, aryl, or heteroaryl group, and preferably a ($C_1$-$C_6$) alkyl or aryl group, and still more preferably a ($C_1$-$C_6$) alkyl group.

In the present invention, "pharmaceutically acceptable" means what is used in the preparation of a pharmaceutical composition, which is generally safe, nontoxic and not biologically or otherwise undesirable and which is acceptable for both veterinary and human pharmaceutical use.

"Pharmaceutically-acceptable salts" of a compound mean of salts that are pharmaceutically acceptable, such as defined here, that have the desired pharmacological activity of the parent compound. Such salts include:

(1) hydrates and solvates, (2) pharmaceutically-acceptable acid addition salts formed with pharmaceutically-acceptable inorganic acids such as hydrochloric acid, hydrobromic acid, sulfuric acid, nitric acid, phosphoric acid and the like, or formed with pharmaceutically-acceptable organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxy ethanesulfonic acid, lactic acid, maleic acid, malic acid, mandelic acid, methanesulfonic acid, muconic acid, 2-naphthalene sulfonic acid, propionic acid, salicylic acid, succinic acid, dibenzoyl-L-tartaric acid, tartaric acid, p-toluenesulfonic acid, trimethylacetic acid, trifluoroacetic acid and the like, or (3) pharmaceutically-acceptable base addition salts formed when an acid proton present in the parent compound is either replaced by a metal ion, for example an alkaline metal ion, an alkaline-earth metal ion or an aluminum ion, or is coordinated with a pharmaceutically-acceptable organic or inorganic base. Acceptable organic bases include diethanolamine, ethanolamine, N-methylglucamine, triethanolamine, tromethamine and the like. Acceptable inorganic bases include aluminum hydroxide, calcium hydroxide, potassium hydroxide, sodium carbonate and sodium hydroxide.

Preferably, the compounds according to the invention will be in the form of pharmaceutically-acceptable base addition salts, the base being such as NaOH or KOH, and especially NaOH.

In particular, compounds according to the invention can have formula (I) above for which:

- - - - $A_0$ represents a single bond or a $=N$ group, $R_1$ represents a residue of a molecule of therapeutic or diagnostic interest, $X_1$ represents an —$X_4$-$A_1$-$(CH_2)_n$-$A_2$-$(CH_2)_m$— chain, $X_2$ represents an imine function (—C=N— or —N=C—), $X_3$ represents a single bond or a $(C_1$-$C_{20})$-alkyl chain, especially $(C_1$-$C_{15})$-alkyl, particularly $(C_1$-$C_{10})$-alkyl, and preferably $(C_1$-$C_4)$-alkyl, optionally broken up and/or followed by one or more moieties chosen from the group consisting of aryl, heteroaryl, cycloalkyl, heterocyclic, —C≡C—, —C($R_7$)=C($R_8$)—, —O—, —S—, —$NR_9$—, —C(O)—, —OC(O)—, —C(O)O—, —SC(O)—, —C(O)S—, —N($R_{10}$)C(O)— and —C(O)N($R_{11}$)— groups, the aryl, heteroaryl and heterocyclic rings being optionally substituted, $X_4$ represents an optionally substituted aryl or heteroaryl group, $A_1$ represents a single bond, O, S, $NR_{27}$, —C(O)—, —OC(O)—, —C(O)O—, —SC(O)—, —C(O)S—, —N($R_{28}$)C(O)— or —C(O)N($R_{29}$)—, $A_2$ represents O, S, $NR_{30}$, —C(O)—, —OC(O)—, —C(O)O—, —SC(O)—, —C(O)S—, —N($R_{31}$)C(O)— or —C(O)N($R_{32}$)—, n represents a whole number comprised between 1 and 5, especially 3, m represents a whole number comprised between 0 and 5, especially between 1 and 5, and particularly 2, $R_7$ and $R_8$ represent, independently of one another, a hydrogen atom or a $(C_1$-$C_6)$alkyl group, and $R_9$ to $R_{11}$ represent, independently of one another, a hydrogen atom or a $(C_1$-$C_6)$alkyl, cycloalkyl, heterocyclic, aryl, heteroaryl or acyl group, and preferably a hydrogen atom or a $(C_1$-$C_6)$alkyl or aryl group, and still more preferably a hydrogen atom or a $(C_1$-$C_6)$alkyl group, $R_{27}$ to $R_{29}$ represent, independently of one another, a hydrogen atom or a $(C_1$-$C_6)$alkyl group, and $R_{30}$ to $R_{32}$ represent, independently of one another, a hydrogen atom or a $(C_1$-$C_6)$alkyl, cycloalkyl, heterocyclic, aryl, heteroaryl or acyl group, and preferably a hydrogen atom or a $(C_1$-$C_6)$alkyl or aryl group, and still more preferably a hydrogen atom or a $(C_1$-$C_6)$alkyl group such as methyl, or pharmaceutically-acceptable salts thereof.

Advantageously, - - - - $A_0$ represents a single bond, $A_0$ then being absent, or a $=N$ group, $A_0$ then representing N.

Advantageously, $X_1$ does not represent a single bond.

$X_4$ will advantageously represent an optionally substituted aryl or heteroaryl group, and especially an optionally substituted aryl group, such as phenyl.

$X_4$ will more particularly represent an optionally substituted phenyl, naphthyl, or indolyl group, the indolyl group being preferably bound to $A_1$ by its nitrogen atom, and preferably represents an optionally substituted phenyl group.

The aryl and heteroaryl groups, such as phenyl, naphthyl and indolyl, of $X_4$ can be substituted as defined previously, i.e., with one or more groups selected from the group consisting of a halogen atom, $NO_2$, —CN, —OH, —SH, —$NR_{12}R_{13}$, —$B(OH)_2$, —$SO_3R_{14}$, —$COOR_{15}$, —C(O)$ONR_{16}R_{17}$, —OPH(O)$OR_{18}$, —PH(O)$OR_{19}$, —OP(O)($OR_{20}$)($OR_{21}$), —P(O)($OR_{22}$)($OR_{23}$), —C(O)$R_{24}$, —$PR_{25}R_{26}$, $(C_1$-$C_6)$alkyl and $(C_1$-$C_6)$alkoxy, with $R_{12}$ to $R_{24}$ representing, independently of one another, a hydrogen atom or a $(C_1$-$C_6)$alkyl group and $R_{25}$ and $R_{26}$ representing, independently of one another, a $(C_1$-$C_6)$alkyl group. Advantageously, they will be substituted by one or more groups chosen from the group consisting of a halogen atom, $NO_2$ and $(C_1$-$C_6)$alkoxy, and especially by $NO_2$.

$A_1$ will advantageously represent a single bond, O, S, $NR_{27}$, —C(O)—, —OC(O)—, —C(O)O—, —SC(O)—, —C(O)S—, —N($R_{28}$)C(O)— or —C(O)N($R_{29}$)—.

$A_1$ will more particularly represent a single bond, O, S or $NR_{27}$, especially a single bond or O, and preferably O.

In particular, $A_1$ will represent a single bond when $X_4$ represents a heteroaryl group comprising a nitrogen atom, such as an indolyl group, and bound to $A_1$ by means of this nitrogen atom. $A_1$ will preferably be different from a single bond, and will notably represent O, S or $NR_{27}$, and in particular an oxygen atom, when $X_4$ represents an aryl, such as a phenyl or naphthyl group, or a heteroaryl bound to $A_1$ by a carbon atom.

$A_2$ advantageously will represent O, S, $NR_{30}$, —C(O)—, —OC(O)—, —C(O)O—, —SC(O)—, —C(O)S—, —N($R_{31}$)C(O)— or —C(O)N($R_{32}$)—; or will even represent —O—$(CH_2CH_2O)_k$—.

$A_2$ will more particularly represent O, S or $NR_{30}$, and preferably $NR_{30}$, with $R_{30}$ such as defined previously and notably representing a hydrogen atom or a $(C_1$-$C_6)$alkyl or aryl group, and preferably a hydrogen atom or a $(C_1$-$C_6)$alkyl group such as methyl. $A_2$ can also represent a —O—$(CH_2CH_2O)_k$— group with k such as defined previously and especially representing 2.

$A_2$ will particularly represent a $NR_{30}$ group with $R_{30}$ representing a hydrogen atom or a $(C_1-C_6)$alkyl group and preferably a $(C_1-C_6)$alkyl group such as methyl.

According to a particular embodiment of the invention, $X_1$ represents a chain of the formula $-X_4-A_1-(CH_2)_n-A_2-(CH_2)_m-$ with:
- $X_4$ representing an optionally substituted phenyl group as defined previously and especially by $NO_2$,
- $A_1$ representing an oxygen atom,
- $A_2$ representing a $NR_{30}$ group with $R_{30}$ representing a $(C_1-C_6)$alkyl group such as methyl,
- n representing 3, and
- m representing 2.

$X_2$ will more particularly represent a $-N=CH-$ function.

$=== A_0$ will advantageously represent a single bond.

$X_3$ will especially represent an $-A_3-$, $-A_3-A_4-A_5-$ or $-A_3-A_4-A_5-A_{12}-A_{13}-$ group ($A_3$ being bound to $A_0$), especially $-A_3-$, $-A_3-A_4-A_5-$ with:
- $A_3$ representing a single bond, O, S, $NR_{33}$, $-X_5-C(=X_6)-X_7-$, $-X_5-CH_2-X_7-$ or

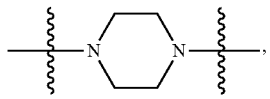

- $A_4$ and $A_{12}$ representing, independently of one another, a $(C_1-C_6)$alkyl, aryl, $(C_1-C_6)$alkyl-aryl or aryl-$(C_1-C_6)$alkyl group; and particularly $(C_1-C_6)$alkyl,
- $A_5$ representing a single bond, O, S, $NR_{34}$, $-X_8-C(=X_9)-X_{10}-$, $-X_8-CH_2-X_{10}-$ or

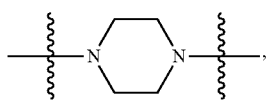

- $A_{13}$ representing a single bond, O, S, $NR_{39}$, $-X_5-C(=X_6)-X_7-$, $-X_5-CH_2-X_7-$ or

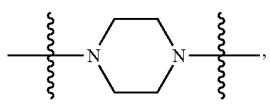

$X_5$ to $X_{10}$ representing, independently of one another, a single bond or O, S, $NR_{35}$ or

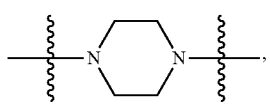

and
$R_{33}$ to $R_{35}$ and $R_{39}$ representing, independently of one another, a hydrogen atom or a $(C_1-C_6)$alkyl group, and particularly a hydrogen atom.

When $X_3$ will represent an $A_3$ group, it may particularly be an $NR_{33}$ or $-X_5-C(=X_6)-X_7-$ group, and particularly a NH, $-C(=O)-NH-$ or $-NH-C(=S)-NH-$ group.

When $X_3$ will represent an $-A_3-A_4-A_5-$ group, $A_3$ may represent a single bond, O, $NR_{33}$ or $-X_5-C(=X_6)-X_7-$, particularly a single bond, O, $NR_{33}$, $C(=O)$, or $-X_5-C(=O)-O-$; $A_4$ can represent a $(C_1-C_6)$alkyl or aryl group, particularly a phenyl or $(CH_2)_a$ group with a representing a whole number between 1 and 5, particularly between 1 and 3; and $A_5$ representing $-X_5-C(=X_6)-X_7-$, particularly $-X_5-C(=O)-NR_{35}-$ such as $-C(=O)-NH-$ or $-O-C(=O)-NH-$.

When $X_3$ will represent an $-A_3-A_4-A_5-A_{12}-A_{13}-$ group, it may particularly be a $-NR_{33}-A_4-C(O)O-A_{12}-C(O)O-$ or $-NR_{33}-A_4-C(O)O-A_{12}-C(O)NR_{39}-$ group with particularly $R_{33}$=Me and $R_{39}$=H.

$X_3$ will represent more particularly an $-A_3-$ or $-A_3-A_4-A_5-$ group with:
- $A_3$ representing a single bond, O, S, $NR_{33}$ or $-X_5-C(=X_6)-X_7-$, particularly a single bond or $NR_{33}$ or $-X_5-C(=X_6)-X_7-$ group, such as $-X_5-C(=X_6)-NR_{35}-$, and particularly such as $-C(=O)-O-$, $-C(=O)-NR_{35}-$ or $-C(=S)-NR_{35}-$,
- $A_4$ being as defined previously, for example $-CH_2-$, $-CH_2-CH_2-$, and
- $A_5$ representing an $-X_8-C(=X_9)-X_{10}-$ group, such as $-X_8-C(=O)-X_{10}-$, particularly such as $-O-C(=O)-NR_{35}-$, $X_3$ will particularly represent a group:
- $-A_3-$ representing a single bond or an $NR_{33}$ or $-X_5-C(=X_6)-NR_{35}-$ group, such as $-C(=X_6)-NR_{35}-$, with $X_6$ preferably representing O or S, or
- $-A_3-A_4-A_5-$ with:
  - $A_3$ representing a single bond or an $-X_5-C(=X_6)-X_7-$ group, such as $-C(=O)-X_7-$ and particularly $-C(=O)-O-$,
  - $A_4$ such as defined previously, and
  - $A_5$ representing an $NR_{34}$ or $-X_8-C(=X_9)-NR_{35}-$ group, such as $-X_8-C(=O)-NR_{35}-$.

$X_3$ can particularly represent an NH, $-C(=O)NH-$, $-C(=S)-NH-$ or $-C(=O)O-(CH_2)_2-OC(=O)-$ group, or even $-NH-C(=S)-NH-$.

The residue $R_1$ of the hydroxy-bisphosphonic acid derivatives of the invention can be a residue of an active ingredient useful for the treatment or diagnosis of a osteolytic or osteocondensing bone remodeling disease, such as primary bone tumors (like osteosarcoma, chondrosarcoma, a giant cell tumor or Ewing's sarcoma), bone metastases, multiple myeloma, phosphate-calcium metabolism deregulation such as hypercalcemia, osteoporosis and inflammatory diseases such as rheumatoid arthritis or prosthetic loosening.

Particularly, the residue $R_1$ may be a residue of a molecule of diagnostic interest chosen from residues of fluorescent molecules such as (5-dimethylamino)naphthalene-1-sulfonyl (dansyl group), 7-nitro-1,2,3-benzoxadiazole (NBD group), a 1-pyrene carboxaldehyde residue, fluorescein residues and derivatives thereof such as fluorescein isothiocyanate (FITC) and rhodamines such as rhodamine B, cyanine derivatives such as fluorescyanines and gallocyanine; residues of luminescent molecules such as residues of dioxetane derivatives and alkaline or alkaline earth sulfides. The corresponding hydroxy-bisphosphonic acid derivatives can also be used for bone tissue imaging, particularly for diagnostic purposes.

Particularly, the $R_1$ residue can be chosen from residues of molecules of therapeutic interest chosen from among anticancer agents, anti-inflammatories, antibiotics, antibacterial agents, anesthetics, steroids and peptides with pro-formation or anti-resorption bone activity.

The R₁ residue may particularly be derived from a molecule of therapeutic interest chosen from anticancer agents such as alkylating molecules like analogs, particularly nitrogen containing, of mustard gas, ifosfamide and derivatives thereof and chlorambucil and derivatives thereof, antineoplastic molecules such as doxorubicin, cisplatin, adriamycin, actinomycin, fluorouracil, methotrexate, etoposide, vincristine, podophyllotoxin, busulfan, docetaxel, 5-fluorouracil and derivatives thereof, or even topoisomerase 1 inhibitors such as irinotecan or analogs thereof such as SN38, anti-inflammatories such as corticosteroids like dexamethasone and derivatives thereof, or nonsteroidal anti-inflammatories such as ibuprofen, indomethacin, bendazac, etodolac, diclofenac, lonazolac, and derivatives thereof; antibiotics such as spiramycin, antibacterial agents such as salicylaldehyde and derivatives thereof such as dalyde; anesthetics such as benzocaine, and steroids such as derivatives of estradiol and estrone.

R₁ can particularly be a podophyllotoxin residue, a nitrogen containing mustard gas analog, chlorambucil, methotrexate, doxorubicin, SN38, ibuprofen, diclofenac, estrone, spiramycin, dalyde or benzocaine.

R₁ can particularly be a podophyllotoxin residue, a nitrogen containing mustard gas analog, methotrexate, ibuprofen, diclofenac, estrone, spiramycin, or benzocaine; and particularly a podophyllotoxin residue or a nitrogen containing mustard gas analog.

R₁ can also be a dansyl group, a 7-nitro-1,2,3-benzoxadiazole, a residue of 1-pyrene carboxaldehyde, of fluorescein or of derivatives thereof or a rhodamine, particularly rhodamine B, and particularly a dansyl group, a residue of 1-pyrene carboxaldehyde or fluorescein or derivatives thereof.

In particular, the compounds of the invention can have the following formula (Ia):

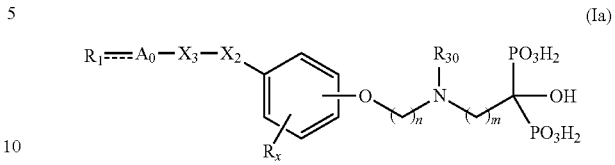

(Ia)

for which $===$ $A_0$, $R_1$, $R_{30}$, $X_2$, $X_3$, n and m are as defined previously and $R_x$ represents one or more substituents of the phenyl ring chosen from the group consisting of a hydrogen atom, a halogen atom, $NO_2$, —CN, —OH, —SH, —$NR_{12}R_{13}$, —$B(OH)_2$, —$SO_3R_{14}$, —$COOR_{15}$, —$C(O)ONR_{16}R_{17}$, —$OPH(O)OR_{18}$, —$PH(O)OR_{19}$, —$OP(O)(OR_{20})(OR_{21})$, —$P(O)(OR_{22})(OR_{23})$, —$C(O)R_{24}$, —$PR_{25}R_{26}$, $(C_1$-$C_6)$alkyl and $(C_1$-$C_6)$alkoxy, with $R_{12}$ to $R_{24}$ representing, independently of one another, a hydrogen atom or a $(C_1$-$C_6)$alkyl group and $R_{25}$ and $R_{26}$ representing, independently of one another, a $(C_1$-$C_6)$alkyl group.

Oxygen will particularly be in the meta or para position, and preferably meta, on the phenyl ring relative to the $X_2$ group.

$R_{30}$ will more particularly represent a $(C_1$-$C_6)$alkyl group, such as methyl. n can represent 3 and m can represent 2.

$R_x$ will more particularly represent one or more, and particularly a single one, phenyl ring substituents chosen from the group consisting of a hydrogen atom, a halogen atom, $NO_2$ and $(C_1$-$C_6)$alkoxy, and particularly chosen from the group consisting of a hydrogen atom and $NO_2$.

$R_x$ will particularly represent a hydrogen atom or an $NO_2$ group. It can advantageously be in the ortho position on the phenyl ring with regard to oxygen.

Examples of formula (I) according to the invention are particularly:

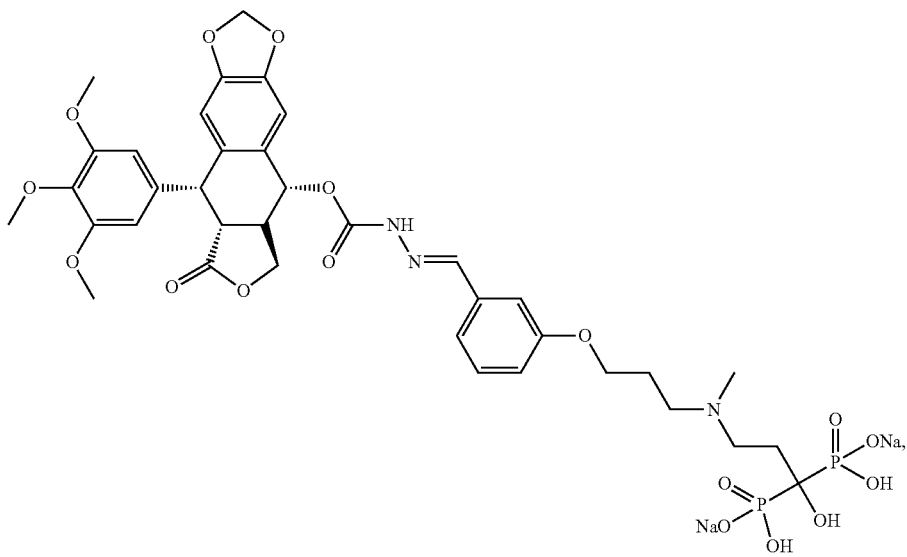

3

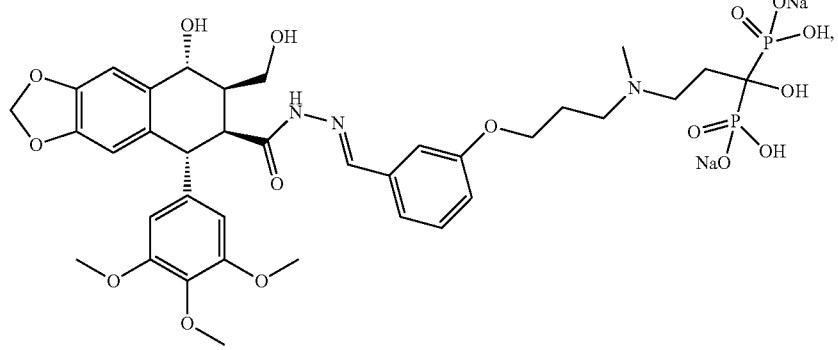
4
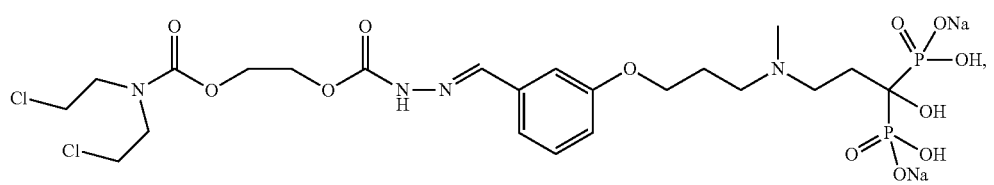
32
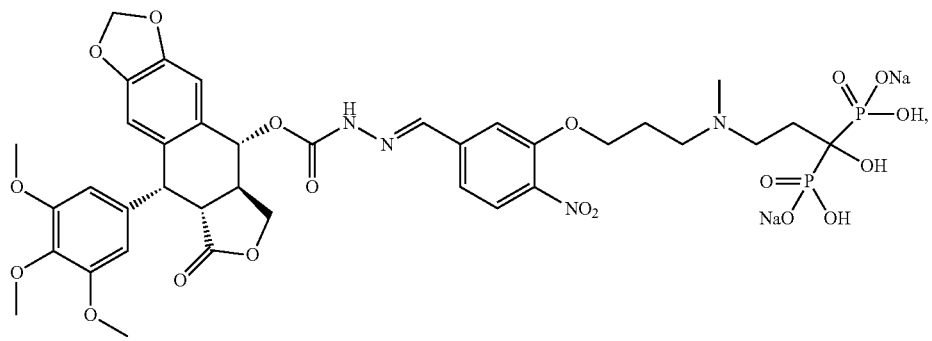
36
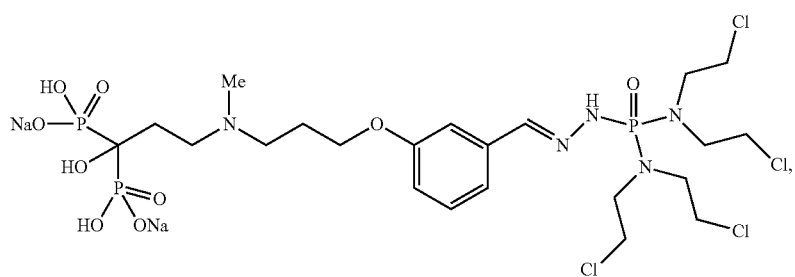
41
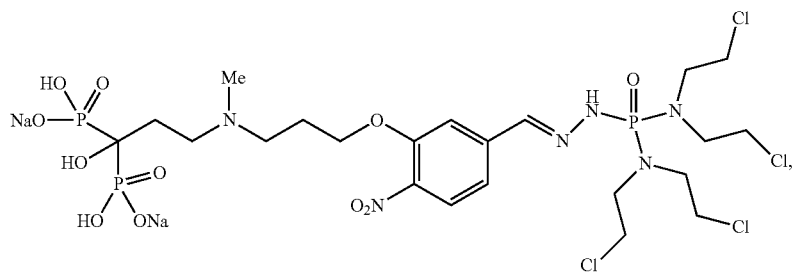
42

46
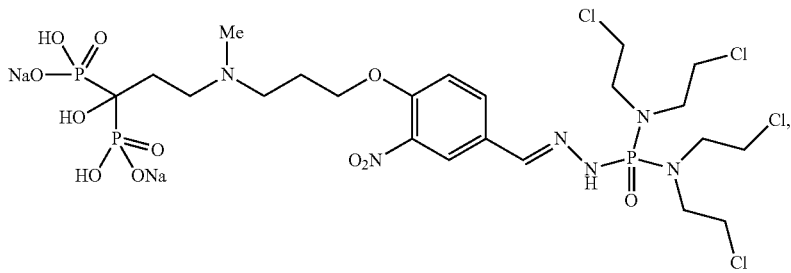
48
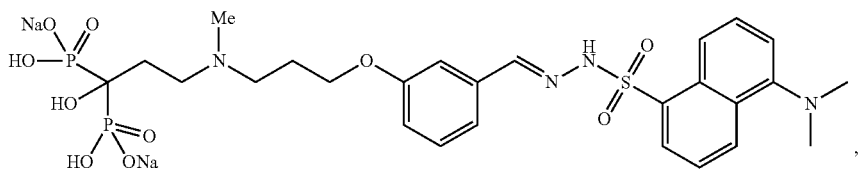
50
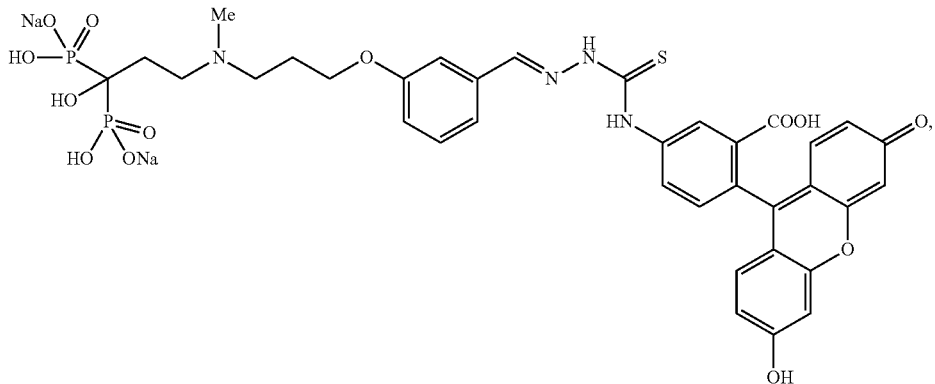
55
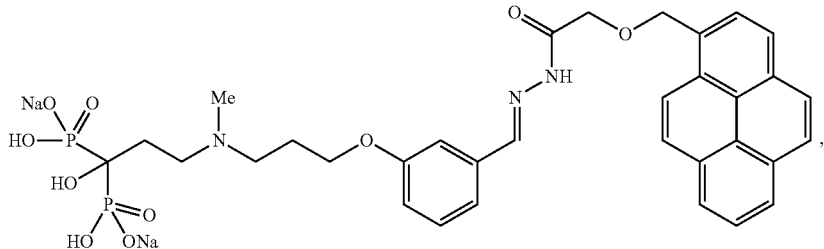
56
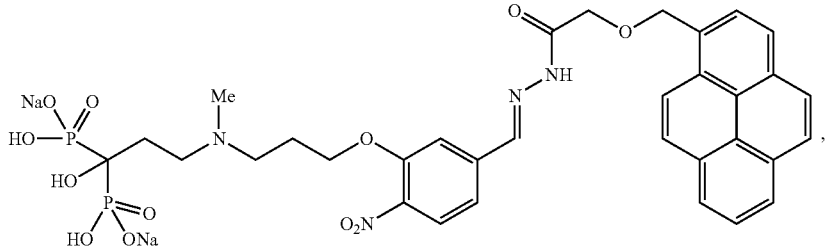

-continued
57
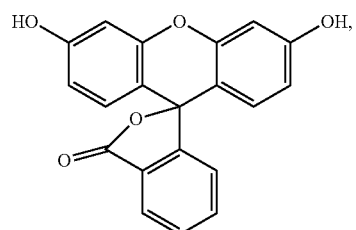
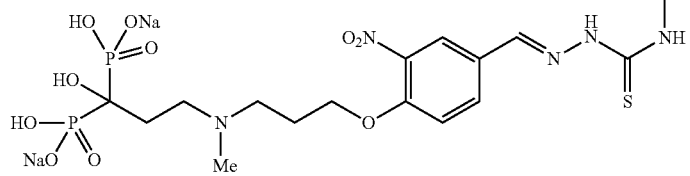
58
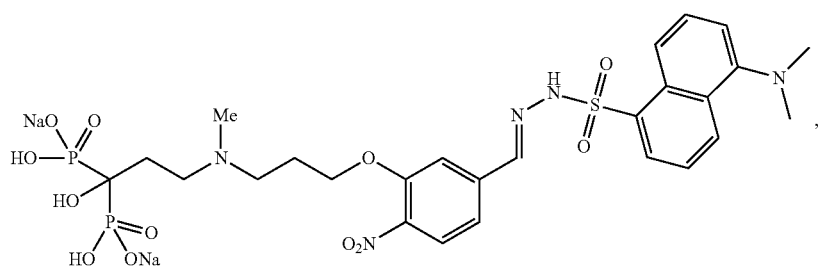
59
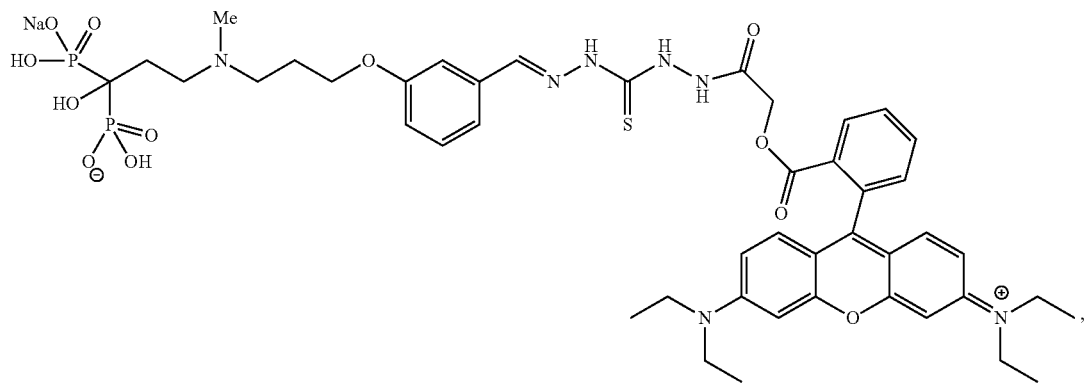
63
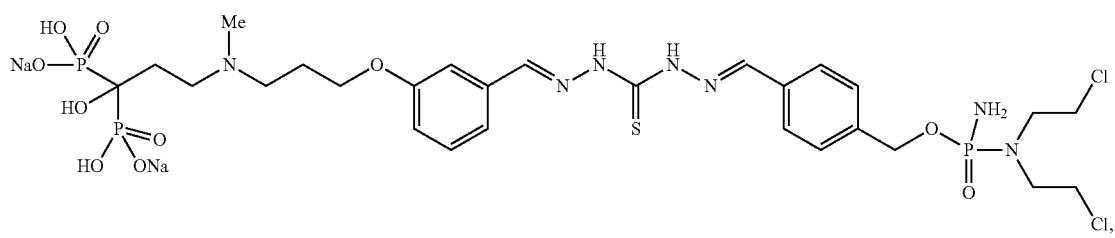
70
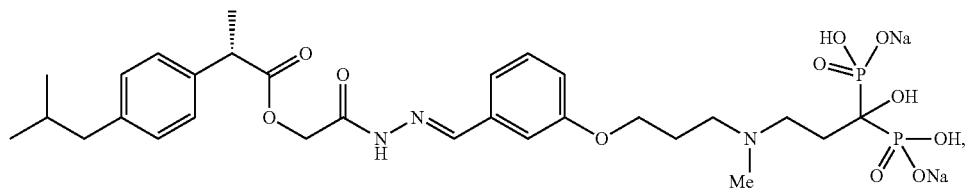

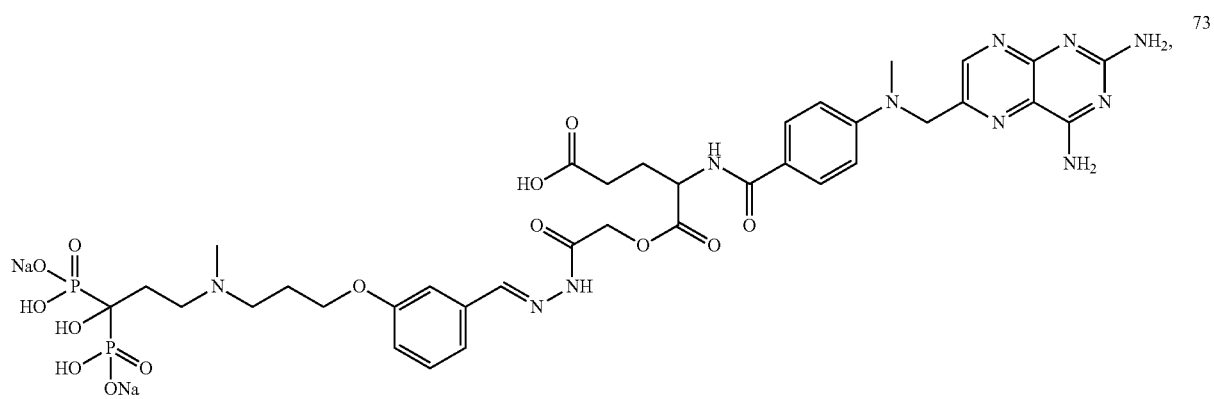
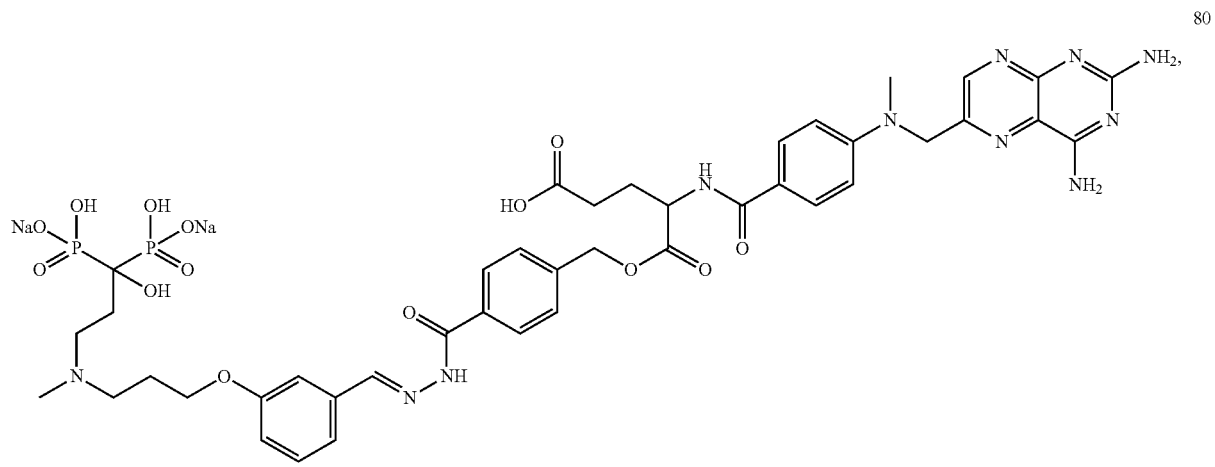
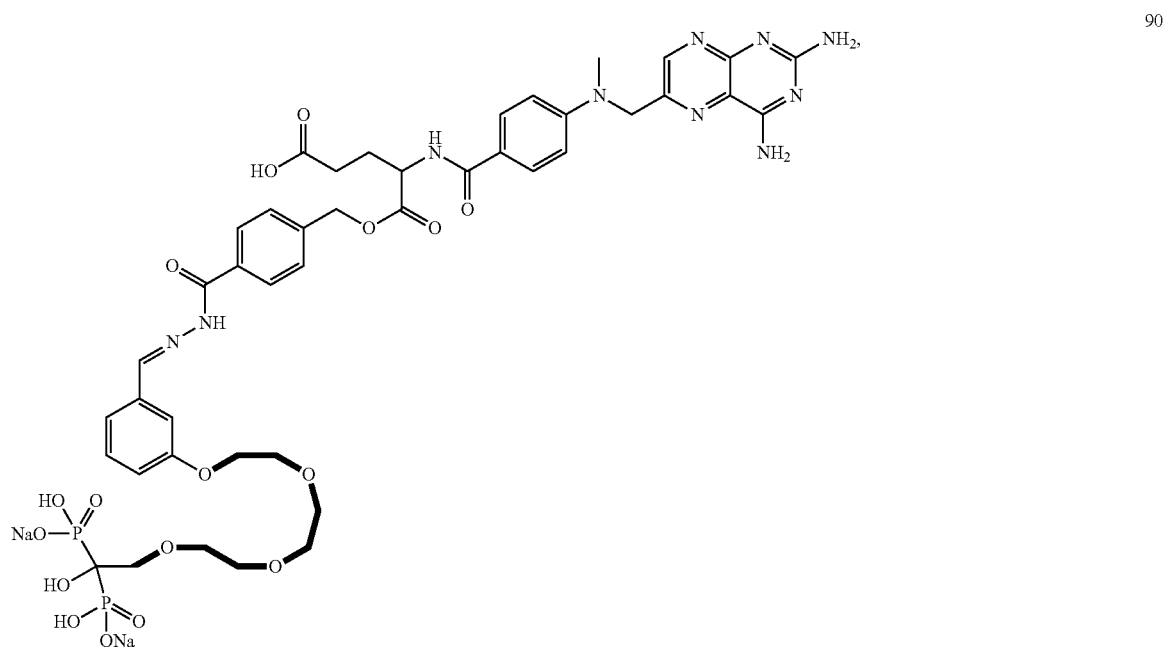

-continued
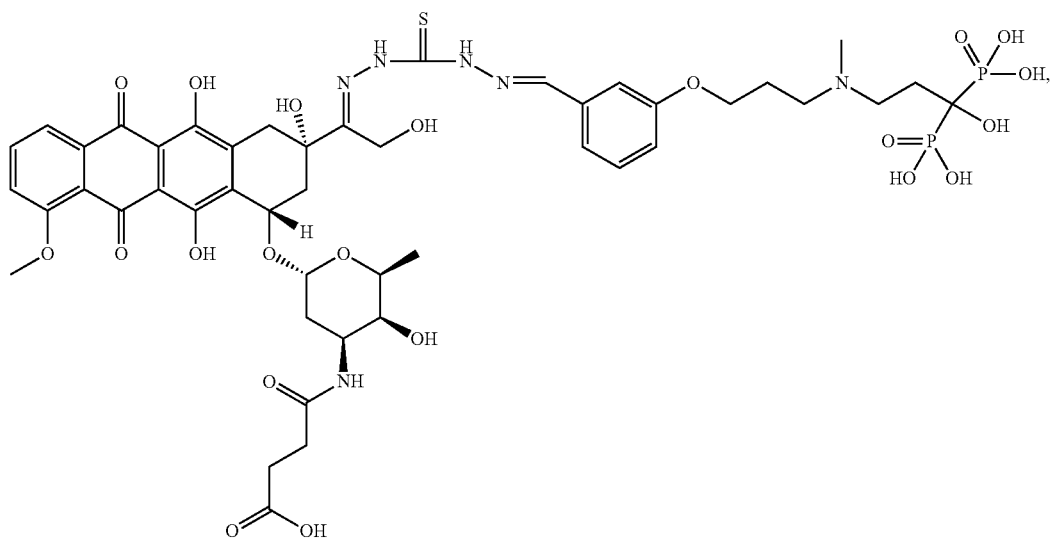
94
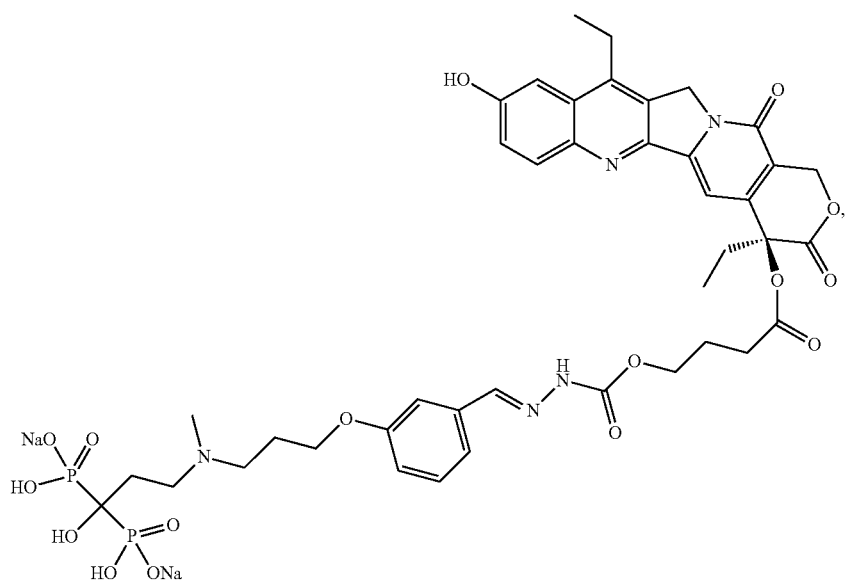
99
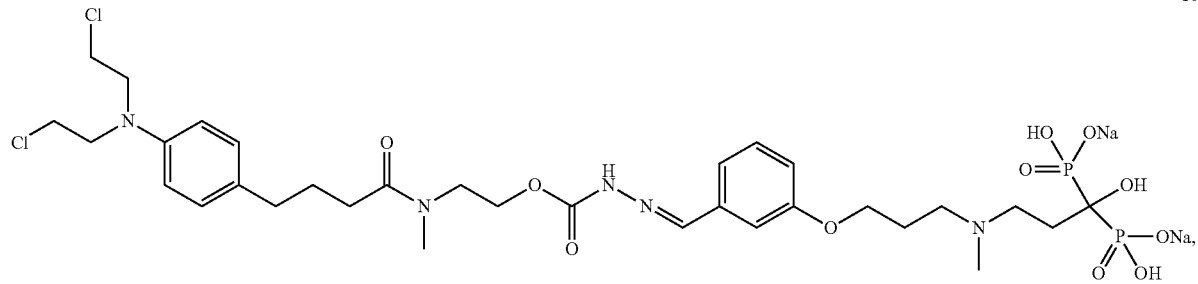
102
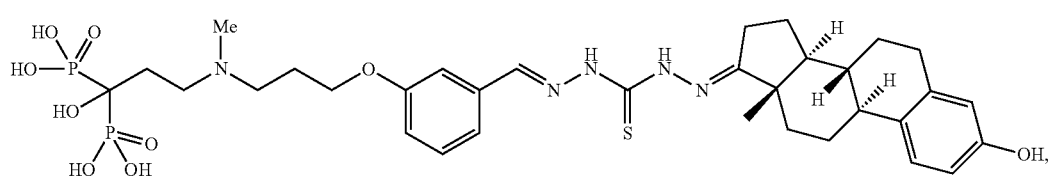
104

108
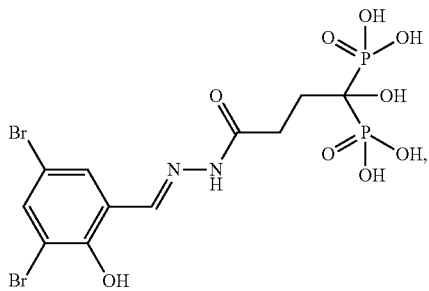
111
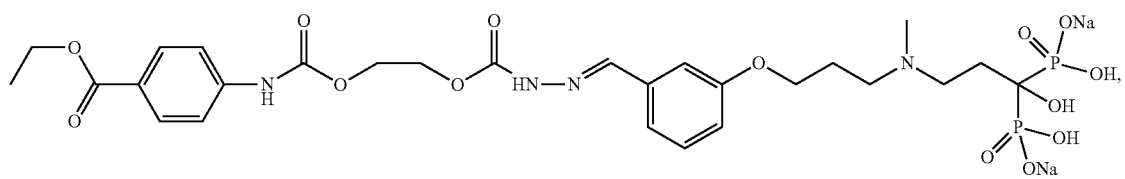
115
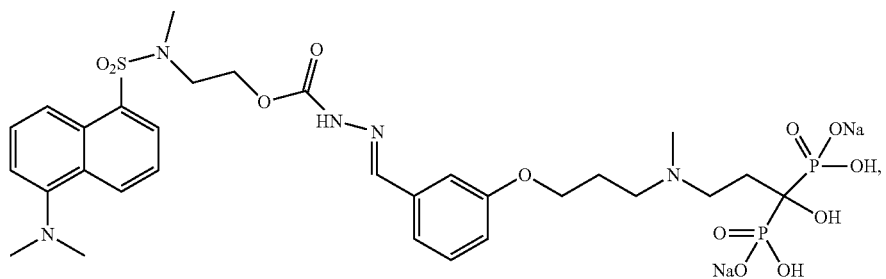
124
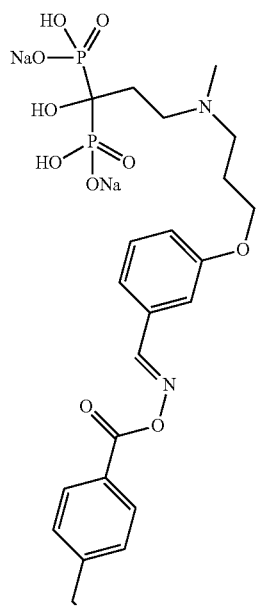
125
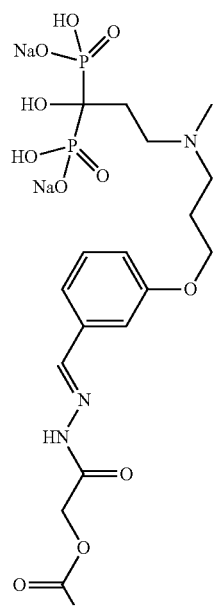

-continued
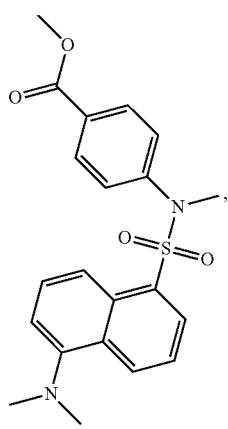
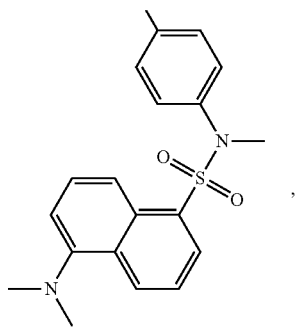
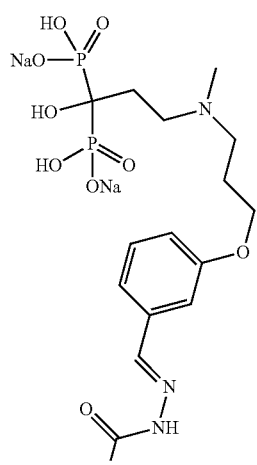
126
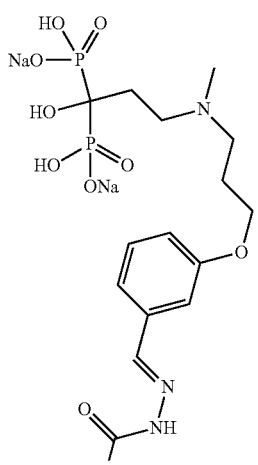
127
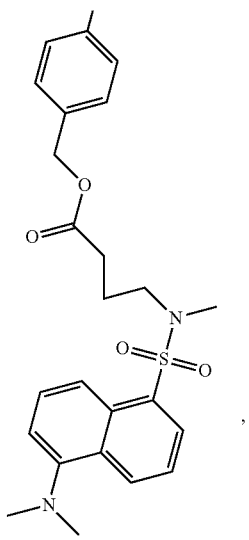
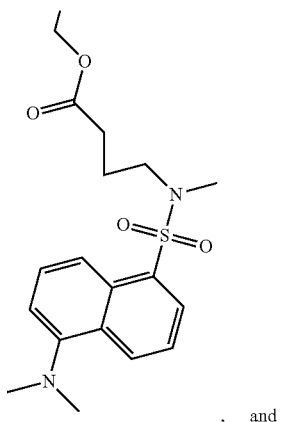
, and

131

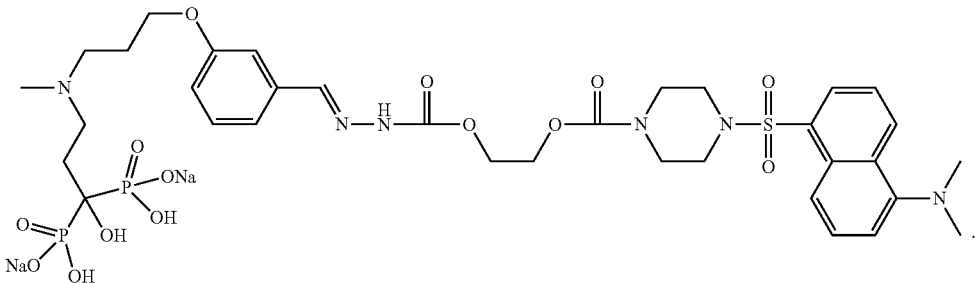

The present invention also concerns a hydroxy-bisphosphonic acid derivative such as described above or a pharmaceutically acceptable salt thereof, for its use as a medicament or a diagnostic product, particularly to target bone tissue.

The present invention also concerns a hydroxy-bisphosphonic acid derivative of the invention or a pharmaceutically acceptable salt thereof, for the preparation of a pharmaceutical or diagnostic composition, more particularly targeting bone tissue.

Particularly, the hydroxy-bisphosphonic acid derivatives of the invention can be used as medicament for the treatment of an osteolytic or osteocondensing bone remodeling condition such as primary bone tumors like osteosarcoma, chondrosarcoma, a giant cell tumor or Ewing's sarcoma; bone metastases; multiple myeloma; phosphate-calcium metabolism deregulation such as hypercalcemia; osteoporosis; and inflammatory diseases such as rheumatoid arthritis or prosthetic loosening, or as a product for diagnostic imaging of bone tissue particularly to diagnose osteolytic or osteocondensing bone remodeling condition such as primary bone tumors like osteosarcoma, chondrosarcoma, giant cell tumor or Ewing's sarcoma; bone metastases; multiple myeloma; and phosphate-calcium metabolism deregulation such as hypercalcemia; osteoporosis; and inflammatory diseases such as rheumatoid arthritis or prosthetic loosening.

According to a first embodiment, hydroxy-bisphosphonic acid derivatives are used for bone tissue imaging.

According to a second embodiment, hydroxy-bisphosphonic acid derivatives are used in a tumor treatment, particularly to treat malignant hypercalcemia, primary bone tumors like osteosarcoma and bone metastases.

According to a third embodiment, hydroxy-bisphosphonic acid derivatives are used in the treatment of osteoporosis or in an anti-inflammatory treatment, particularly to treat rheumatoid arthritis.

The present invention also concerns a pharmaceutical or diagnostic composition comprising at least one hydroxy-bisphosphonic acid derivative of the invention such as described previously, or a pharmaceutically-acceptable salt thereof and at least one pharmaceutically-acceptable carrier.

This composition can be formulated so as to be administered, particularly, subcutaneously, intravenously, intramuscularly or transdermally, i.e., preferably in an injectable form or a patch, and intended for mammals, including humans. The dosage will vary according to the treatment and according to the condition in question.

The compounds of the invention as active ingredients can be used in doses comprised between 0.01 mg and 1000 mg per day, given in a single dose once daily or administered in several doses throughout the day, for example twice daily in equal doses. The dose administered per day is advantageously comprised between 5 mg and 500 mg, and still more advantageously between 10 mg and 200 mg. It may be necessary to use doses exceeding these ranges, which those skilled in the art can realize themselves.

The present invention also relates to a pharmaceutical or diagnostic composition such as defined above for its use as a medicament or diagnostic product.

Particularly, the compositions of the invention can be used for bone tissue imaging or for the treatment or diagnosis of an osteolytic or osteocondensing bone remodeling disease, such as primary bone tumors (like osteosarcoma, chondrosarcoma, a giant cell tumor or Ewing's sarcoma), bone metastases, multiple myeloma, phosphate-calcium metabolism deregulation (such as hypercalcemia), osteoporosis and inflammatory diseases (such as rheumatoid arthritis or prosthetic loosening).

According to a first embodiment, the diagnostic compositions are used for bone tissue imaging.

According to a second embodiment, the therapeutic compositions are used in a tumor treatment, particularly to treat malignant hypercalcemia, primary bone tumors and bone metastases.

According to a third embodiment, the therapeutic compositions are used in the treatment of osteoporosis or in an anti-inflammatory treatment, particularly to treat rheumatoid arthritis.

Compounds of formula (I) can be prepared according to the following successive steps:

(a1) coupling between a compound of formula (II) below:

for which $X_1$ is as defined above and $X_{11}$ represents a —CHO, or —NH$_2$ function, with a compound of formula (III) below:

for which $====$ $A_0$, $R_1$ and $X_3$ are as defined previously and $X_{12}$ represents a —NH$_2$ function when $X_{11}$=CHO and represents a —CHO function when $X_{11}$=NH$_2$, to give a compound of formula (I), (b1) optionally salifying the compound of formula (I) obtained in step (a1) above to give a pharmaceutically-acceptable salt thereof, and (c1) separation from the reaction medium of the compound of formula (I) or one of its pharmaceutically-acceptable salts obtained in step (a1) or (b1).

Step (a1):

The coupling reaction between aldehyde (CHO) and amine ($NH_2$) to give an imine function can be carried out in a polar solvent such as water, MeOH, EtOH, iPrOH, PrOH, BuOH, BuOH, DMF, DMSO, MeNO2, MeCN, THF, dioxane, pyridine, HMPT, diglime, ethylene glycol, glycerol, and mixtures thereof and particularly such as water, methanol and mixtures thereof.

A base may optionally be added to the reaction medium, such as NaOH, KOH, LiOH, $Ca(OH)_2$, $NaHCO_3$, $Na2CO_3$, $KHCO_3$, $K_2CO_3$, $Li_2CO_3$, $NH_3$, amine, pyridine, picoline, quinoline, DMAP, DBU, etc., and particularly NaOH or KOH.

Conversely, an acid can be added, such as HCl, $H_2SO_4$, AcOH, $CF_3COOH$, or even HCOOH.

The reaction is advantageously conducted at room temperature, i.e., at a temperature comprised between 15 and 40° C., particularly between 20 and 30° C., and particularly around 25° C.

However, if the reagents are not heat sensitive, the reaction medium can be heated to around 100-150° C.

Additional protection and deprotection steps may be used in this process, if necessary, particularly in the case where the active ingredient will have other functionalities that can react under the reaction conditions.

Step (b1):

The salification step will be conducted in the presence of a pharmaceutically acceptable acid or base such as defined above. It may particularly be a base such as NaOH, KOH, LiOH, $Ca(OH)_2$, $NaHCO_3$, $Na_2CO_3$, $KHCO_3$, $K_2CO_3$, $Li_2CO_3$, $NH_3$, an amine, pyridine, picoline, quinoline, DMAP, DBU, etc., particularly NaOH or KOH, and particularly NaOH.

Step (c1):

The compound of formula (I) thus obtained can be separated from the reaction medium by methods well-known to the person skilled in the art, such as, for example, by extraction, evaporation of the solvent or even by precipitation and filtration.

Furthermore, this compound can also be purified, if necessary, by techniques well known to the person skilled in the art, such as recrystallization if the compound is crystalline, by silica gel column or reverse phase chromatography or even by high performance liquid chromatography (HPLC).

Compounds of formula (II) can be prepared by techniques known to the person skilled in the art.

When $A_2=NR_{30}$, the compound of formula (II) can be prepared from a compound of formula (IV) below:

$$X_{11}-X_4-A_1-H \quad (IV)$$

for which $X_4$, $X_{11}$ and $A_1$ are as defined previously according to the following successive steps:

(a2) optionally protection of the $X_{11}$ function to give a compound of formula (IVbis) below:

$$Xbis_{11}-X_4-A_1-H \quad (IVbis)$$

for which $X_4$ and $A_1$ are as defined previously and $Xbis_{11}$ represents a protected CHO or $NH_2$ function, (b2) reaction of a compound of formula (IV) or (IVbis) with a compound of formula (V) below:

$$A6-(CH_2)_n-A_7 \quad (V)$$

for which n is such as defined previously and $A_6$ and $A_7$ represent, independently of one another, a leaving group such as a halogen atom, and particularly a bromine atom, a tosylate or even a mesylate, to give a compound of formula (VI) or (VIbis) below:

$$X_{11}-X_4-A_1-(CH_2)_n-A_7 \quad (VI)$$

or $$Xbis_{11}-X_4-A_1-(CH_2)_n-A_7 \quad (VIbis)$$

for which $X_4$, $X_{11}$, $Xbis_{11}$, $A_1$, $A_7$ and n are as defined previously, (c2) reaction of the compound of formula (VI) or (VIbis) above with an amine of formula $R_{30}NH_2$, $R_{30}$ being as defined previously to give a compound of formula (VII) or (VIIbis) below:

$$X_{11}-X_4-A_1-(CH_2)_n-NHR_{30} \quad (VII)$$

or $$Xbis_{11}-X_4-A_1-(CH_2)_n-NHR_{30} \quad (VIIbis)$$

for which $X_4$, $X_{11}$, $Xbis_{11}$, $A_1$, $R_{30}$ and n are as defined previously, (d2) reaction of the compound of formula (VII) or (VIIbis) above with an acid of formula $A_8-(CH_2)_mCOOH$ for which $A_8$ represents a leaving group such as a halogen atom, a tosylate or mesylate, or with acrylic acid when m=2 to give a compound of formula (VIII) or (VIIIbis) below:

$$X_{11}-X_4-A_1-(CH_2)_n-NR_{30}-(CH_2)_m-COOH \quad (VIII) \text{ or}$$

$$Xbis_{11}-X_4-A_1-(CH_2)_n-NR_{30}-(CH_2)_m-COOH \quad (VIIIbis)$$

for which $X_4$, $X_{11}$, $Xbis_{11}$, $A_1$, $R_{30}$, n and m are as defined previously, (e2) conversion of the acid function of the compound of formula (VIII) or (VIIIbis) above into a hydroxy-bisphosphonic acid to give a compound of formula (II) or a compound of formula (IIbis) below:

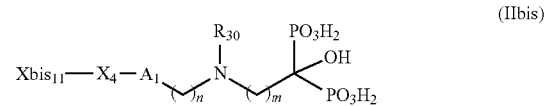

for which $X_4$, $Xbis_{11}$, $A_1$, $R_{30}$, n and m are as defined previously, (f2) optionally deprotection of function $Xbis_{11}$ to give a compound of formula (II), and (g2) separation from the reaction medium of the compound of formula (II) obtained in step (e2) or (f2) above.

Step (a2):

Compounds of formula (IV) are either commercial or accessible by techniques known to the person skilled in the art.

The aldehyde function (CHO) can be protected by any protective group well known to the skilled person and particularly a cyclic or noncyclic acetal of formula $-C(OR_{36})(OR_{37})$ where $R_{36}$ and $R_{37}$, identical or different, preferably identical, represent a ($C_1$-$C_6$)alkyl group or $R_{35}$ and $R_{37}$ together form a chain of formula $-(CH_2)_p-$ with p representing 2 or 3, particularly 3.

The aldehyde function can also be protected in the acetal form by reaction with the corresponding alcohol, $R_{36}OH$ and $R_{37}OH$, preferably identical, or, when $R_{36}$ and $R_{37}$ together form a chain with $HO-(CH_2)_p-OH$.

The amine function ($NH_2$) can be protected by any protective group well known to the skilled person and particularly by a Boc (butyloxycarbonyl) group.

Step (b2):

In the present invention, "leaving group" means a chemical group that can be easily displaced by a nucleophile during a nucleophilic substitution reaction, the nucleophile being more particularly an amine, and particularly a secondary amine. Such a leaving group can also more particularly be a halogen atom such as a chlorine atom, a mesylate (MsO—) or even a tosylate (p-Me-Ph-O—).

This step can be conducted in the presence of a base such as $K_2CO_3$. $A_6$ and $A_7$ can each represent a halogen atom such as a bromine atom.

Step (c2):

This step can be conducted in a solvent such as THF, particularly at room temperature.

Step (d2):

This step can be conducted in the presence of a base such as DIPEA, particularly in a solvent such as alcohol, for example methanol, and particularly at room temperature.

Step (e2):

During this step, the carboxylic acid function can be activated, particularly in the form of acid chloride (—COCl) or even borane derivative by reaction with a borane such as catecholborane.

The activated carboxylic acid function is then reacted with tris(trimethylsilyl)phosphite and then with an aliphatic alcohol such as methanol to give the hydroxy-bisphosphonic acid function.

Step (f2):

The functionalities (aldehyde or amine) in the protected form are deprotected by techniques well known to the skilled person, particularly by acid or basic treatment. The acetal derivatives may particularly be deprotected to release the aldehyde function, in acid medium, particularly in the presence of HCl.

Step (g2): see step (c1) above.

The present invention also relates to a compound of the following formula (II):

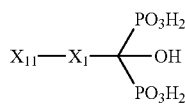

(II)

for which
$X_1$ represents an —$X_4$-$A_1$-$(CH_2)_n$-$A_2$-$(CH_2)_m$— chain,
$X_{11}$ represents a —CHO or —$NH_2$ group, and particularly —CHO,
$X_4$ represents a single bond or an optionally substituted aryl or heteroaryl group,
$A_1$ represents a single bond, O, S, $NR_{27}$, —C(O)—, —C(S)—, —C=N—, —N=C—, —C=C—, —C≡C—, —OC(O)—, —C(O)O—, —SC(O)—, —C(O)S—, —N($R_{28}$)C(O)— or —C(O)N($R_{29}$)—,
$A_2$ represents a single bond, O, S, $NR_{30}$, —C(O)—, —C(S)—, —C=N—, —N=C—, —C=C—, —C≡C—, —OC(O)—, —C(O)O—, —SC(O)—, —C(O)S—, —N($R_{31}$)C(O)—, —C(O)N($R_{32}$)—, —O—$(CH_2CH_2O)_k$— or an -$A_9$-$(CH_2)_a$-$A_{10}$-$CH_2)_b$-$A_{11}$- group,
$A_9$ and $A_{11}$ each represent, independently of one another, O, S, or $NR_{38}$,
$A_{10}$ represents an aryl, heteroaryl or heterocyclic group,
n represents a whole number comprised between 0 and 5, particularly between 1 and 5, and especially 3,
m represents a whole number comprised between 0 and 5, particularly between 1 and 5, and especially 2,
k represents a whole number comprised between 1 and 10, especially between 1 and 5,
a and b represent, independently of one another, a whole number comprised between 0 and 5,
$R_{27}$ to $R_{29}$ represent, independently of one another, a hydrogen atom or a ($C_1$-$C_6$)alkyl group, and
$R_{30}$ to $R_{32}$ and $R_{38}$ represent, independently of one another, a hydrogen atom or a ($C_1$-$C_6$)alkyl, cycloalkyl, heterocyclic, aryl, heteroaryl or acyl group, and preferably a hydrogen atom or a ($C_1$-$C_6$)alkyl or aryl group, and still more preferably a hydrogen atom or a ($C_1$-$C_6$)alkyl group such as methyl, or a pharmaceutically-acceptable salt thereof.

In particular, the compounds of formula (II) can have the characteristics below: $X_1$ represents an —$X_4$-$A_1$-$(CH_2)_n$-$A_2$-$(CH_2)_m$— chain,
$X_{11}$ represents a —CHO or —$NH_2$ group, and particularly —CHO,
$X_4$ represents an optionally substituted aryl or heteroaryl group,
$A_1$ represents a single bond, O, S, $NR_{27}$, —C(O)—, —OC(O)—, —C(O)O—, —SC(O)—, —C(O)S—, —N($R_{28}$)C(O)— or —C(O)N($R_{29}$)—,
$A_2$ represents O, S, $NR_{30}$, —C(O)—, —OC(O)—, —C(O)O—, —SC(O)—, —C(O)S—, —N($R_{31}$)C(O)— or —C(O)N($R_{32}$)—,
n represents a whole number comprised between 1 and 5, especially 3,
m represents a whole number comprised between 0 and 5, particularly between 1 and 5, and especially 2,
$R_{27}$ to $R_{29}$ represent, independently of one another, a hydrogen atom or a ($C_1$-$C_6$)alkyl group, and
$R_{30}$ to $R_{32}$ represent, independently of one another, a hydrogen atom or a ($C_1$-$C_6$)alkyl, cycloalkyl, heterocyclic, aryl, heteroaryl or acyl group, and preferably a hydrogen atom or a ($C_1$-$C_6$)alkyl or aryl group, and still more preferably a hydrogen atom or a ($C_1$-$C_6$)alkyl group such as methyl, or a pharmaceutically-acceptable salt thereof.

Advantageously, $X_1$ will not represent a single bond.

$X_4$ will advantageously represent an optionally substituted aryl or heteroaryl group, and especially an optionally substituted aryl group, such as phenyl.

$X_4$ will more particularly represent an optionally substituted phenyl, naphthyl, or indolyl group, the indolyl group being preferably bound to $A_1$ by its nitrogen atom, and preferably an optionally substituted phenyl group.

The aryl and heteroaryl groups, such as phenyl, naphthyl and indolyl, $X_4$ can be substituted as defined previously and particularly by one or more groups chosen from the group consisting of a halogen atom, $NO_2$ and ($C_1$-$C_6$)alkoxy, and particularly $NO_2$.

$A_1$ will advantageously represent a single bond, O, S, $NR_{27}$, —C(O)—, —OC(O)—, —C(O)O—, —SC(O)—, —C(O)S—, —N($R_{28}$)C(O)— or —C(O)N($R_{29}$)—.

$A_1$ will more particularly represent a single bond, O, S or $NR_{27}$, particularly a single bond or O, and preferably O.

In particular, $A_1$ will represent a single bond when $X_4$ represents a heteroaryl group, such as an indolyl group, comprising a nitrogen atom and bound to $A_1$ by means of this nitrogen atom. $A_1$ will preferably be different from a single bond, and will particularly represent an oxygen atom, when $X_4$ represents an aryl, such as a phenyl or naphthyl group, or a heteroaryl bound to $A_1$ by a carbon atom.

$A_2$ will advantageously represent O, S, $NR_{30}$, —C(O)—, —OC(O)—, —C(O)O—, —SC(O)—, —C(O)S—, —N($R_{31}$)C(O)— or —C(O)N($R_{32}$)—.

$A_2$ will more particularly represent O, S or $NR_{30}$, and preferably $NR_{30}$, with $R_{30}$ such as defined previously and representing particularly a hydrogen atom or a ($C_1$-$C_6$)alkyl or aryl group, and preferably a hydrogen atom or a ($C_1$-$C_6$) alkyl group such as methyl.

$A_2$ will particularly represent an $NR_{30}$ group with $R_{30}$ representing a hydrogen atom or a ($C_1$-$C_6$)alkyl group and preferably a ($C_1$-$C_6$)alkyl group such as methyl.

According to a particular embodiment of the invention, $X_1$ represents a chain of the formula —$X_4$-$A_1$-$(CH_2)_n$-$A_2$-$(CH_2)_m$— with:
$X_4$ representing a phenyl group optionally substituted as defined previously and especially by $NO_2$,
$A_1$ representing an oxygen atom,
$A_2$ representing an $NR_{30}$ group with $R_{30}$ representing a ($C_1$-$C_6$)alkyl group such as methyl,
n representing 3, and
m representing 2.

The compounds of formula (II) can particularly have formula (IIa) below:

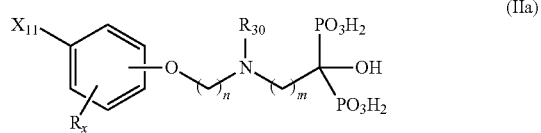

for which $R_{30}$, $X_{11}$, $R_x$, n and m are as defined previously.

This compound can particularly be a compound 20 or 35 below:

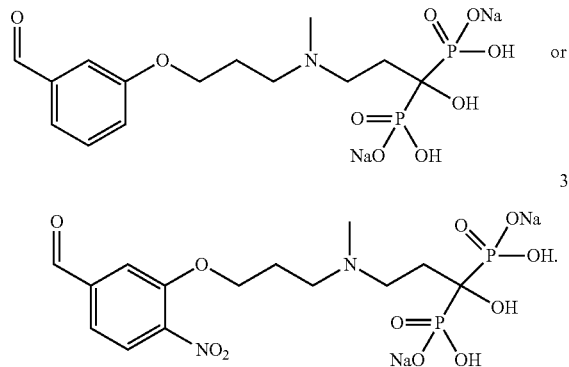

Compounds of formula (II) can be prepared by techniques known to the person skilled in the art.

When $A_2$=$NR_{30}$, the compound of formula (II) can be prepared by the method indicated above, with an optional salification step if necessary, before or after the last step of separating the prepared compound from the reaction medium.

The present invention also relates to the use of a compound of formula (II) such as defined above to prepare a vectorized molecule of therapeutic or diagnostic interest, particularly intended to target bone tissue.

The molecule of therapeutic or diagnostic interest, possibly functionalized to have a functionality $X_{12}$=CHO or $NH_2$, is then bound to the compound of formula (II) by coupling of its $X_{12}$ functionality and the $X_{11}$ functionality of the compound of formula (II) (by coupling between CHO and $NH_2$).

The molecule of therapeutic or diagnostic interest can be a molecule useful for the treatment or diagnosis of a osteolytic or osteocondensing bone remodeling disease, such as primary bone tumors (like osteosarcoma, chondrosarcoma, a giant cell tumor or Ewing's sarcoma), bone metastases, multiple myeloma, phosphate-calcium metabolism deregulation such as hypercalcemia, osteoporosis and inflammatory diseases such as rheumatoid arthritis or prosthetic loosening.

The molecule of diagnostic interest may more particularly be a molecule useful for medical imaging, particularly of bone tissue, such as a fluorescent molecule like (5-dimethylamino)naphthalene-1-sulfonyl residue (dansyl group), 7-nitro-1,2,3-benzoxadiazole (NBD group), 1-pyrene carboxaldehyde, fluorescein and its derivatives such as fluorescein isothiocyanate (FITC) and rhodamines such as rhodamine B, and cyanine derivatives such as fluorescyanines and gallocyanine; or a luminescent molecule such as derivatives of dioxetane and alkaline or alkaline earth sulfides.

The molecule of therapeutic interest can more particularly be an active ingredient chosen from among anticancer agents, anti-inflammatories, antibiotics, anesthetics, steroids and peptides with pro-formation or anti-resorption activity in bone.

The molecule of therapeutic interest may particularly be chosen from among anticancer agents such as alkylating molecules like analogs, particularly nitrogen containing, of mustard gas, ifosfamide and derivatives thereof or antineoplastic molecules such as doxorubicin, cisplatin, adriamycin, actinomycin, fluorouracil, methotrexate, etoposide, vincristine, podophyllotoxin, busulfan, docetaxel, 5-fluorouracil and derivatives thereof; anti-inflammatories such as corticosteroids like dexamethasone and derivatives thereof, or nonsteroidal anti-inflammatory drugs like ibuprofen, indomethacin, bendazac, etodolac, diclofenac, lonazolac, and derivatives thereof; antibiotics such as spiramycin; anesthetics such as benzocaine; and steroids such as derivatives of estradiol and estrone.

The molecule of therapeutic interest may particularly be podophyllotoxin or a nitrogen-containing analog of mustard gas.

The molecule of diagnostic interest may be a dansyl or pyrene derivative.

The vectorized molecule of diagnostic or therapeutic interest may more particularly be a molecule of formula (I) such as defined above.

DESCRIPTION OF THE ATTACHED FIGURES

FIG. 1 shows the percentage of living cells of the cell lines POS1 and L929 as a function of the concentration of compound 3 tested.

FIGS. 2a and 2b show images obtained by fluorescence medical imaging of the back or stomach, respectively, of mice after injection of the carrier alone (negative control), compound 49 or compound 50.

ABBREVIATIONS USED

Figure 1:
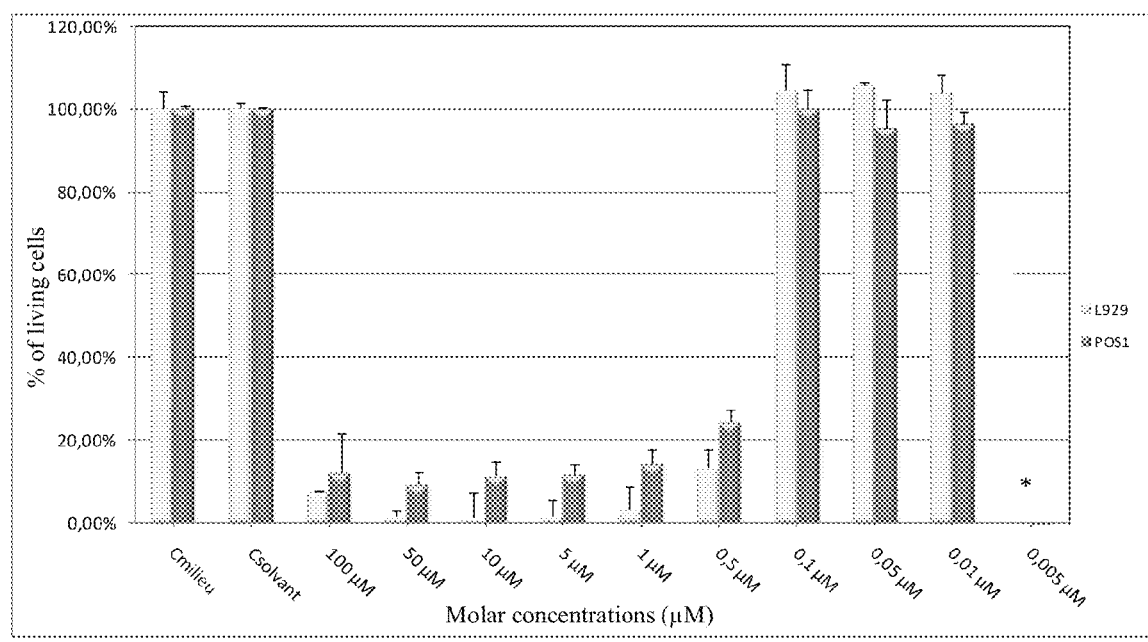

TLC Thin layer chromatography
CDI Carbonyldiimidazole
DBU Diaza(1,3)bicyclo[5.4.0]undecane
DCM Dichloromethane
DIPEA Diisopropylethylamine
DMAP Dimethylaminopyridine
DMF Dimethylformamide
DMSO Dimethylsulfoxide
EDCI 1-Ethyl-3-(3-dimethylaminopropyl)carbodiimide
eq. Equivalent
ES Electrospray
HMDS Hexamethyldisilazane
HMPT Hexa-methylphosphoramide
HOBt 1-Hydroxybenzotriazole
PTSA para-toluene sulfonic acid
Py Pyridine
NMR Nuclear magnetic resonance
RT Room temperature
TEA Triethylamine
Tf Triflate
THF Tetrahydrofuran

EXAMPLES

1. Synthesis of Compounds According to the Invention 1.1. Synthesis of Molecules of Formula (II)

Compound 20 was prepared according to the following reaction diagram:

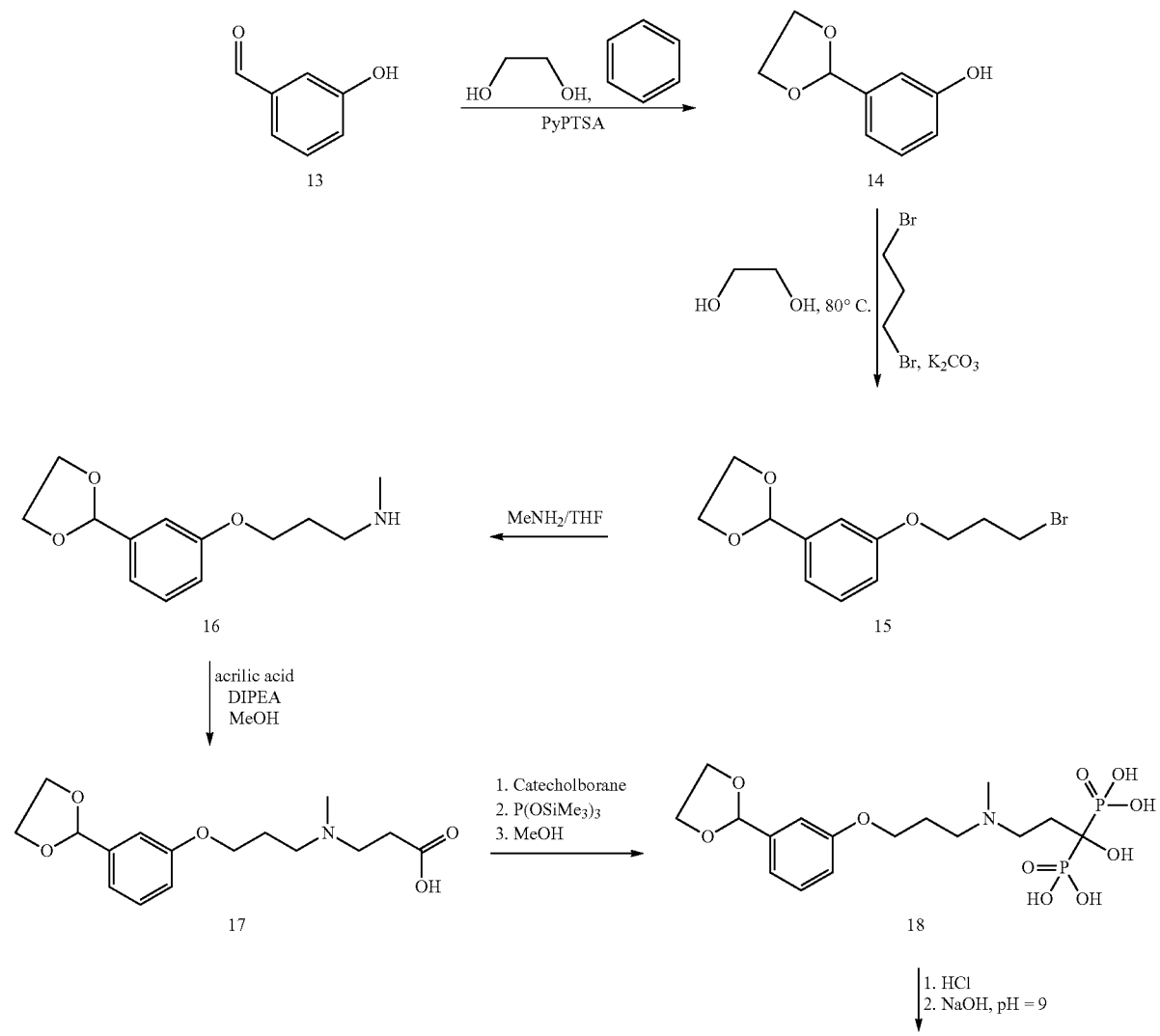

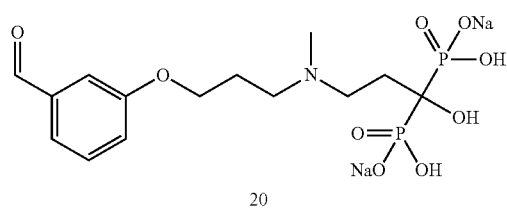

20

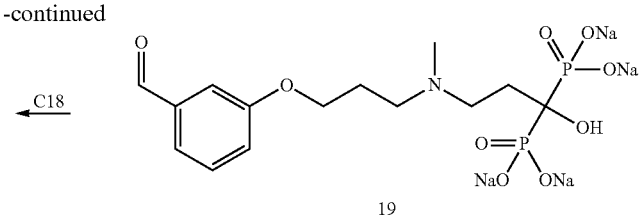 −continued

19

Compound 14:

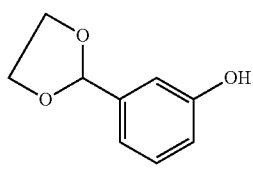

14

A solution of 13 (5 g, 41 mmol, 1 eq.), pyridine (176 mg, 2.2 mmol, 0.05 eq.) and PTSA.H$_2$O (429 mg, 2.2 mmol, 0.05 eq.) in ethylene glycol (100 ml) was stirred at 80° C. for 1 h. The reaction was monitored by TLC. The reaction mixture containing 14 was used in the step below without any treatment. The molecule was characterized by its 1H NMR spectrum.

Compound 15:

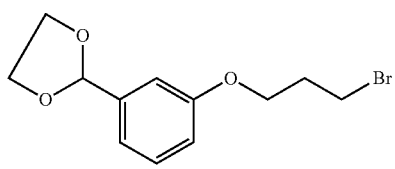

15

K$_2$CO$_3$ (6.5 g, 47 mmol, 1.15 eq.) then 1,3-dibromopropane (16.6 ml, 1.64 mmol, 4 eq.) were added to the reaction medium from the previous step still at 80° C. After 2 h of stirring at the same temperature, the reaction medium was cooled. 100 ml of water were added. The solution obtained was extracted with ether and the organic phase was dried with anhydrous Na$_2$SO$_4$. After concentration at reduced pressure (25 mbar, 90° C.), crude compound 15 (12 g) was obtained in the form of an orange oil that was used in the step below without additional purification. The molecule was characterized by its 1H NMR spectrum.

Compound 16:

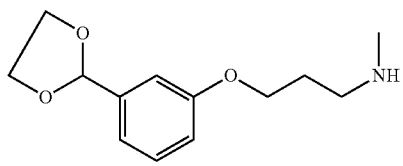

16

The crude solution 15 (~41 mmol, 1 eq.) from the previous step in MeNH$_2$ (2M/THF) was left at RT for 16 h. The reaction medium was concentrated at reduced pressure and silica gel chromatographed (gradient from DCM to DCM: MeOH=5:1). Thus, 6.9 g of 16 were obtained with a yield of 71% in three steps from 13. The molecule was characterized by its 1H NMR spectrum.

Compound 17:

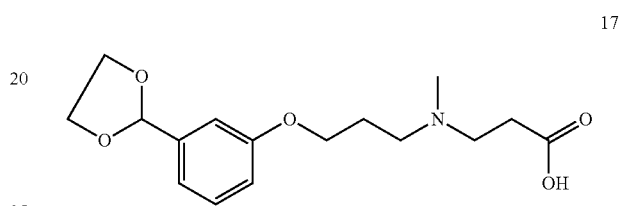

17

A solution of 16 (6.9 g, 29 mmol, 1 eq.) in a mixture of MeOH (120 ml), DIPEA (23.9 ml, 145 mmol, 5 eq.) and acrylic acid (7.7 ml, 116 mmol, 4 eq.) was left at RT for 3 days. The reaction medium was concentrated at reduced pressure at 40° C. and silica gel chromatographed (gradient from DCM to MeOH). Thus, 4.4 g of 17 were obtained with a yield of 49% The molecule was characterized by its 1H NMR spectrum.

Compound 20:

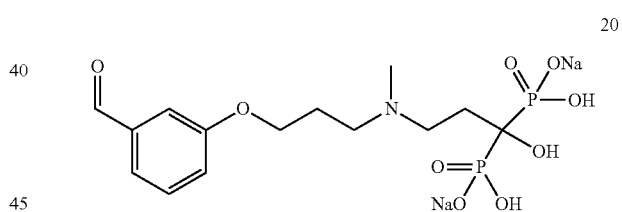

20

Catecholborane (5 ml, 1M/THF, 5 mmol, 2.1 eq.) was added to a solution of 17 (730 mg, 2.36 mmol, 1 eq.) in THF (5.5 ml), with stirring at RT under argon (hydrogen release). Three minutes later, tris(trimethylsilyl)phosphite (2.5 ml, 8.26 mmol, 3.5 eq.) was added all at once and stirring was continued for 16 h at RT. MeOH (3 ml) was added and the mixture containing a white precipitate was stirred for 30 min. Then, an excess of ether was added and after stirring, the white precipitate was separated, washed with ether, dried under vacuum and dissolved in an aqueous solution of HCl (2M, 4 ml) at RT. After 10 min, the solution was basified to pH=8-9 with concentrated NaOH and the solution obtained was chromatographed (C18, gradient from 3% MeOH/H$_2$O to 50% MeOH/H$_2$O). Thus, 435 mg of 20 were obtained with a yield of 40%. The molecule was characterized by its 1H NMR spectrum and its mass spectrum (ES).

A series of analogs of molecule 17 were synthesized in a similar way. This series includes examples of different aryl/heteroaryl rings, alternative protective groups and free aldehydes:

The compounds above were prepared according to a synthesis protocol similar to the one for compound 17. For compounds 9e3 and 9e4, the aldehyde functions were protected according to the following protocol:

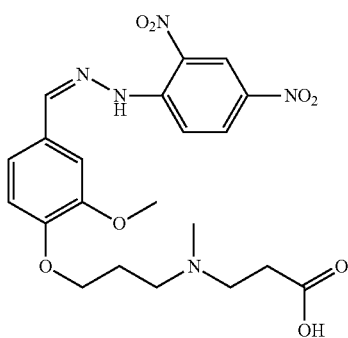

9e3

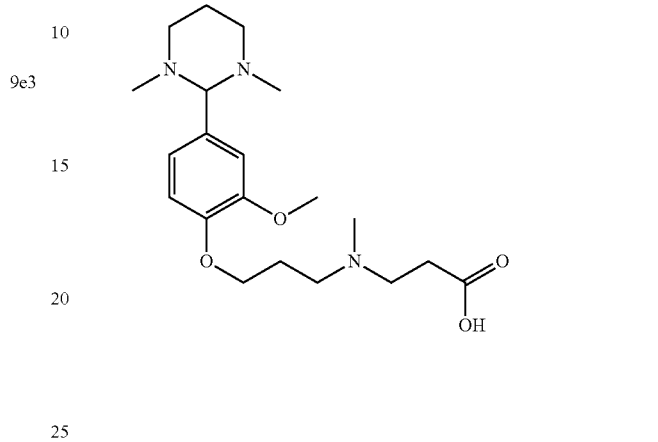

9e4

Compound 9e3:
2,4-dinitrophenylhydrazine (447 mg, 1.356 mmol, 2 eq.) was added to the solution of 9e1 (200 mg, 0,678 mg, 1 eq.) in MeOH (5 ml) and the suspension obtained was stirred at RT for 3 h. The red precipitate was filtered and introduced onto a silica gel column in a DMSO solution. After elution (gradient from MeOH to water), 140 mg (43%) of final product 9e3 were obtained in the form of a dark red power.

Compound 9e4:
A solution of 9e1 (100 mg, 0,339 mg, 1 eq.) and N,N'-dimethyl-(1,3-diaminopropane) (35 mg, 0.34 mmol, 1 eq.) in MeOH (1 ml) was evaporated to dry for 15 min at 50° C. to obtain the pure final product 9e4 (126 mg, 98%).

All these products were characterized by their 1H NMR spectra.

1.2. Synthesis of Molecules of Formula (I)

Compounds 3 and 4, podophyllotoxin derivatives, were prepared from compound 20 above according to the general diagram below:

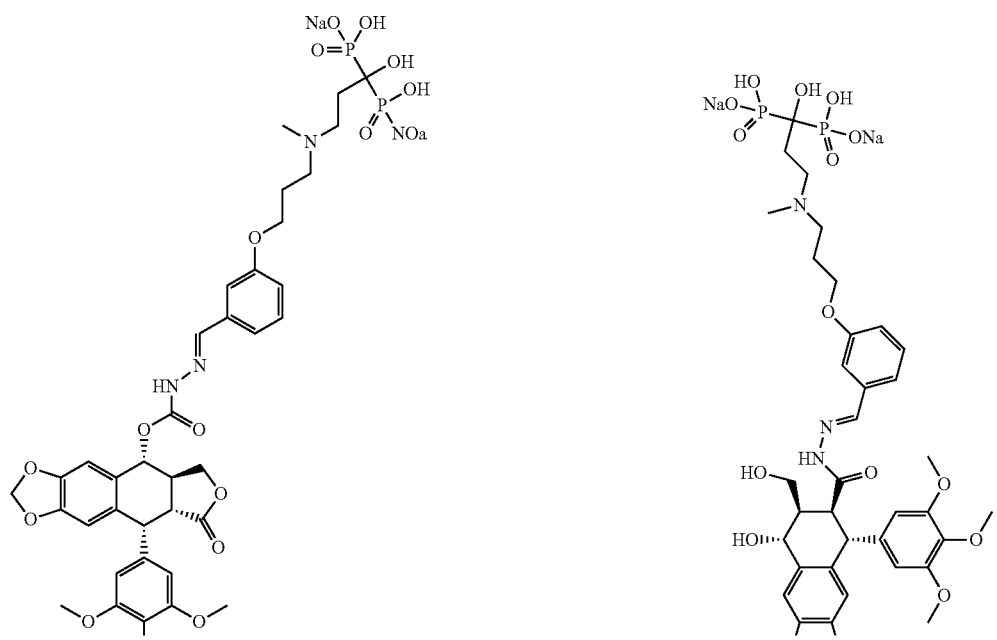

-continued

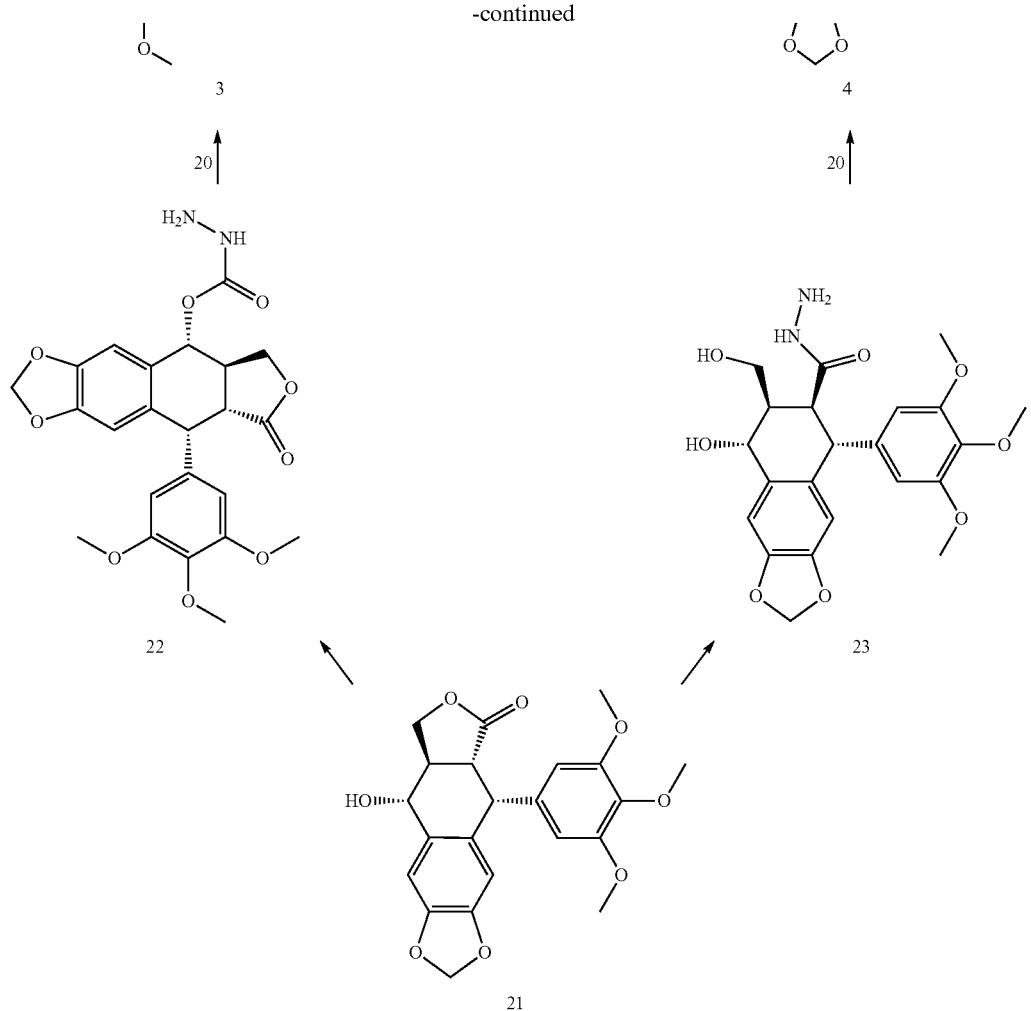

Compound 22

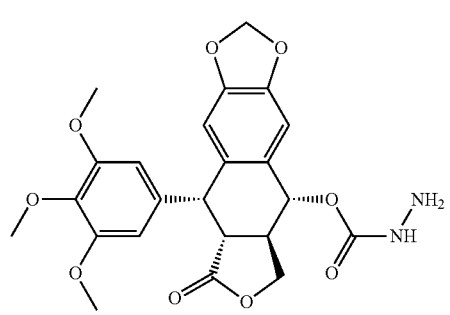

DCM (6 ml) was added to a dry mixture of podophyllotoxin 21 (90 mg, 0.217 mmol, 1 eq.) and CDI (176 mg, 1.085 mmol, 5 eq.) at RT under argon. After 1 h, NH$_2$NH$_2$.H$_2$O (1M/MeCN, 2.17 ml, 2.17 mmol, 10 eq.) was added to the transparent solution obtained. After 10 min, the reaction mixture was introduced onto a silica gel column (60 cm$^3$) and chromatographed (gradient from DCM to DCM:MeOH=10:1) to give compound 22 in the form of white powder (99 mg, yield=97%). The molecule was characterized by its 1H NMR spectrum.

Compound 23:

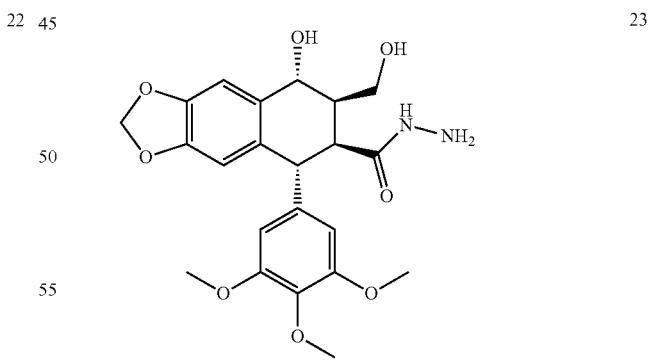

NH$_2$NH$_2$.H$_2$O (2 ml) was added to a podophyllotoxin solution (400 mg, 0.966 mmol) in MeOH (8 ml). This solution was concentrated under vacuum at 50° C. and the residue obtained was chromatographed on silica gel (gradient from DCM to MeOH). Thus, compound 23 was obtained in the form of a white solid foam (410 mg, yield=89%). The molecule was characterized by its 1H NMR spectrum.

Compound 3:

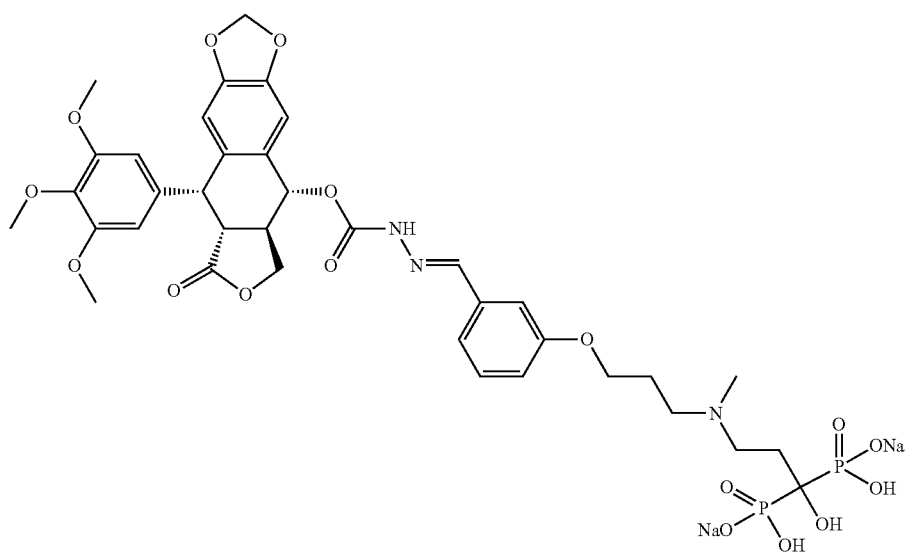

A solution of 20 (96 mg, 0.21 mmol, 1 eq.) in water (1.5 ml) was added to a solution of 22 (119 mg, 0.252 mmol, 1.2 eq.) in MeOH (1.5 ml). The mixture obtained was left at RT for 16 h. After dilution with iPrOH, the precipitate formed was filtered, washed with iPrOH and dried. 150 mg of crude compound 3 were obtained with yield of 80%. After chromatographic purification (C18, gradient from 3% MeOH/ $H_2O$ to MeOH), evaporation and crystallization ($H_2O$-iPrOH-$Et_2O$), 75 mg of compound 3 were obtained in the form of a white powder (yield=40%). The molecule was characterized by its 1H NMR spectrum and its mass spectrum (ES).

Compound 4:

NaOH (2M, 5 drops) were added to a suspension of 23 (94 mg, 0.21 mmol, 1 eq.) in water (1 ml). A solution of 20 (136 mg, 0.3 mmol, 1.4 eq.) in water (1 ml) was added to the slightly cloudy solution obtained and the mixture obtained was thoroughly stirred. After 1 h, the pH of the slightly cloudy solution obtained was adjusted to 7 with a few drops of concentrated phosphate buffer. After 16 h at RT, the nearly transparent solution was introduced into a C18 column. After elution (gradient from 3% MeOH/$H_2O$ to 50% MeOH/$H_2O$), compound 4 was obtained (150 mg, yield=81%). The molecule was characterized by its 1H NMR spectrum and its mass spectrum (ES).

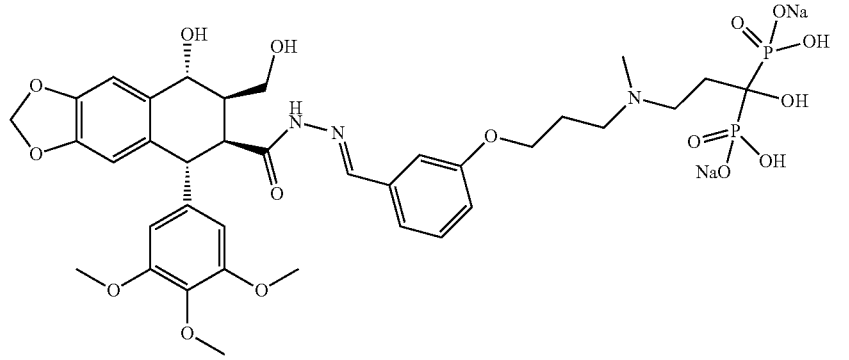

Compound 32, a nitrogen-containing mustard gas analog (antitumor alkylating agent), was prepared according to the following reaction diagram:

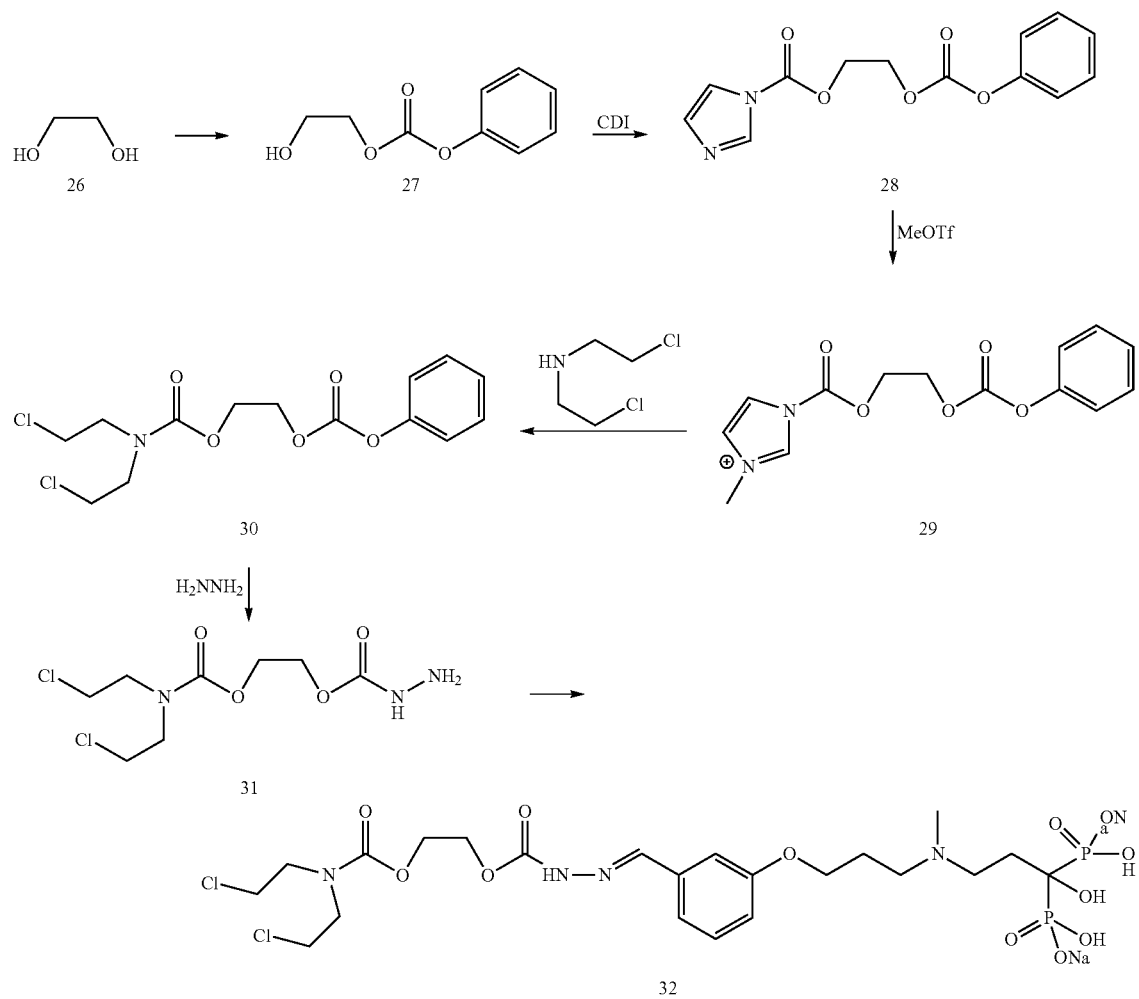

Compound 27:

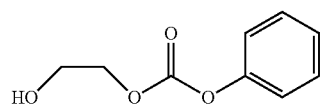

THF (20 ml) and DCM (10 ml) were added to NaHCO$_3$ (3 g) under argon, then ethylene glycol (8 ml, 144 mmol, 5.8 eq.) followed by phenyl chloroformate (3.2 ml, 25 mmol, 1 eq.) at RT. The reaction mixture was well stirred for 5 h at RT (release of CO$_2$ observed). DCM was then added (150 ml) and the mixture obtained was well stirred. The solution was filtered through anhydrous Na$_2$SO$_4$ and the residue obtained was washed several times with DCM filtered through anhydrous Na$_2$SO$_4$. The solution obtained was concentrated under vacuum and chromatographed on silica gel (gradient from DCM to Et$_2$O) which gave compound 27 in the form of a colorless oil (2.5 g, yield=56%). The molecule was characterized by its 1H NMR spectrum.

Compound 28:

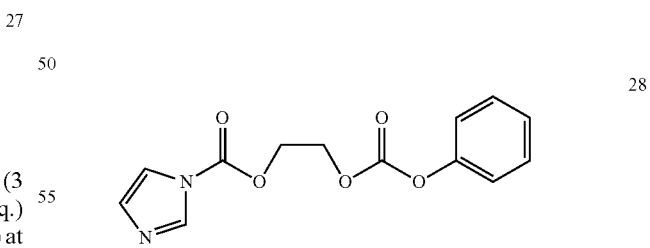

CDI (1.39 g, 8.58 mmol, 3 eq.) was added to a solution of 27 (520 mg, 2.86 mmol, 1 eq.) in THF (4 ml) at RT under argon. After 10 min, the precipitate formed was separated and the remaining solution was introduced into a silica gel column and chromatographed (Et$_2$O) to give compound 28 (270 mg, yield=34%). The molecule was characterized by its 1H NMR spectrum.

Compound 30:

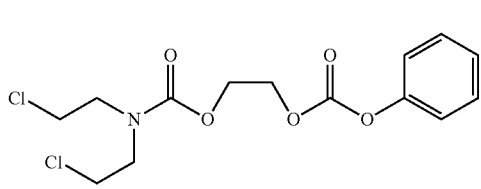

MeOTf (97 mg, 67 μl, 0.59 mmol, 1.2 eq.) was added to a solution of 28 (135 mg, 0.49 mmol, 1 eq.) in DCM (3 ml) at 0° C. under argon. After 1 of stirring di(2-chloroethyl)amine (139 mg, 124 μl, 0.98 mmol, 2 eq.), freshly prepared from its hydrochloride (DCM/2M NaHCO$_3$ extraction), the organic phase was dried on anhydrous Na$_2$SO$_4$ and concentrated under vacuum at RT), were added and the reaction mixture was left to progressively warm up at RT for 3 h. The resulting reaction mixture was then introduced into a silica gel column and chromatographed (gradient from cyclohexane to Et$_2$O) to give compound 30 (130 mg, yield=76%). The molecule was characterized by its 1H NMR spectrum.

Compound 31:

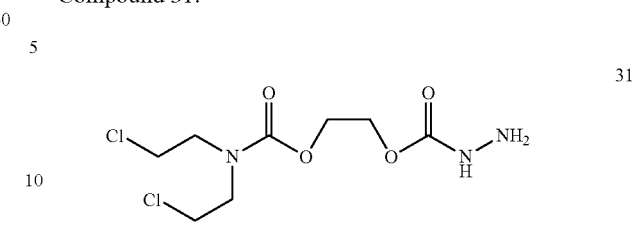

NH$_2$NH$_2$.H$_2$O (1M/MeCN, 342 μl, 342 mmol, 2 eq.) was added to a solution of 30 (60 mg, 0.171 mmol, 1 eq.) in DCM (1 ml). After 40 min, the reaction mixture was introduced onto a silica gel column (20 cm$^3$) and chromatographed (gradient from DCM to DCM:MeOH=10:1) to give compound 31 in the form of a clear yellow oil (32 mg, 65%). The molecule was characterized by its 1H NMR spectrum.

Compound 32:

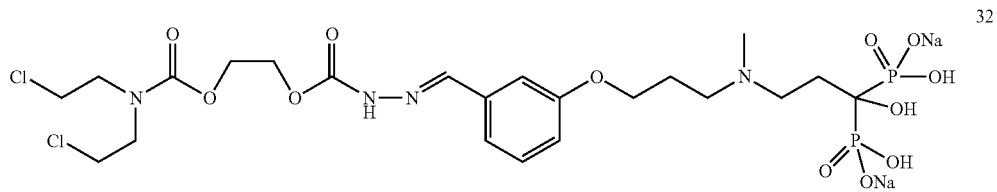

A solution of 20 (46 mg, 0.101 mmol, 1 eq.) in water (300 μl) was added to a solution of 31 (29 mg, 0.101 mmol, 1 eq.) in MeOH (300 μl) at RT. An oil then separated from the cloudy mixture obtained. After stirring, the oil gradually transformed into crystals. The mixture was left at RT for 16 h, then the crystals were filtered, washed (50% MeOH in water, then with MeOH) and dried under vacuum. Thus, compound 32 was obtained (30 mg, yield=41%). The molecule was characterized by its 1H NMR spectrum and its mass spectrum (ES).

Compound 36, an analog of compound 3, was prepared according to the following reaction diagram and according to the protocols described previously:

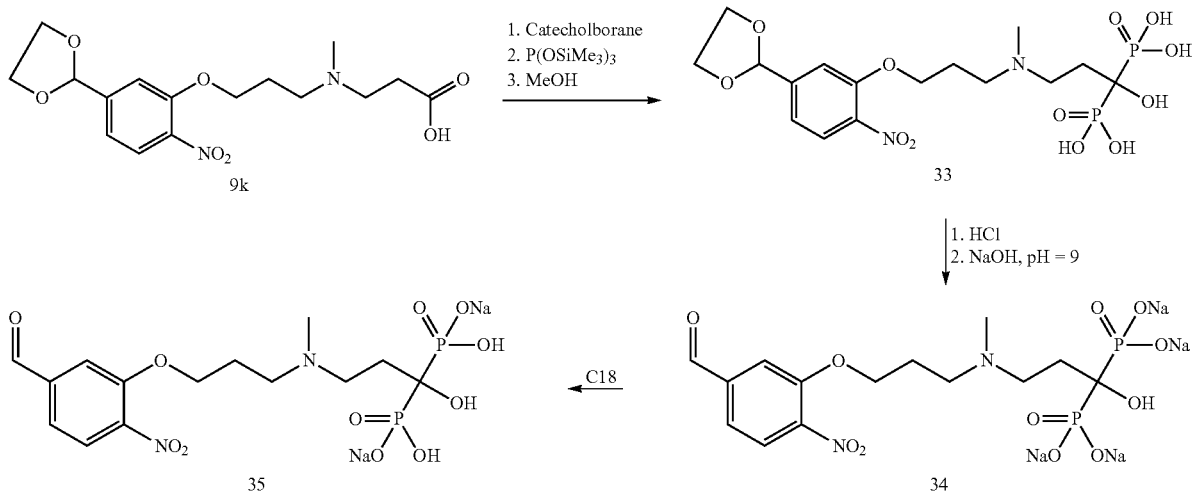

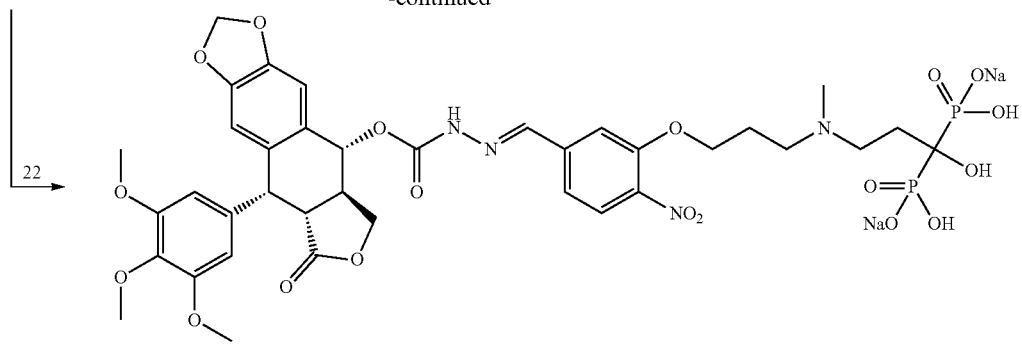
Molecule 36 was characterized by its 1H and 31P NMR spectrum.
Molecules 41 and 42, bearing a mustard gas residue, were synthesized according to the following reaction diagram, according to protocols described previously:
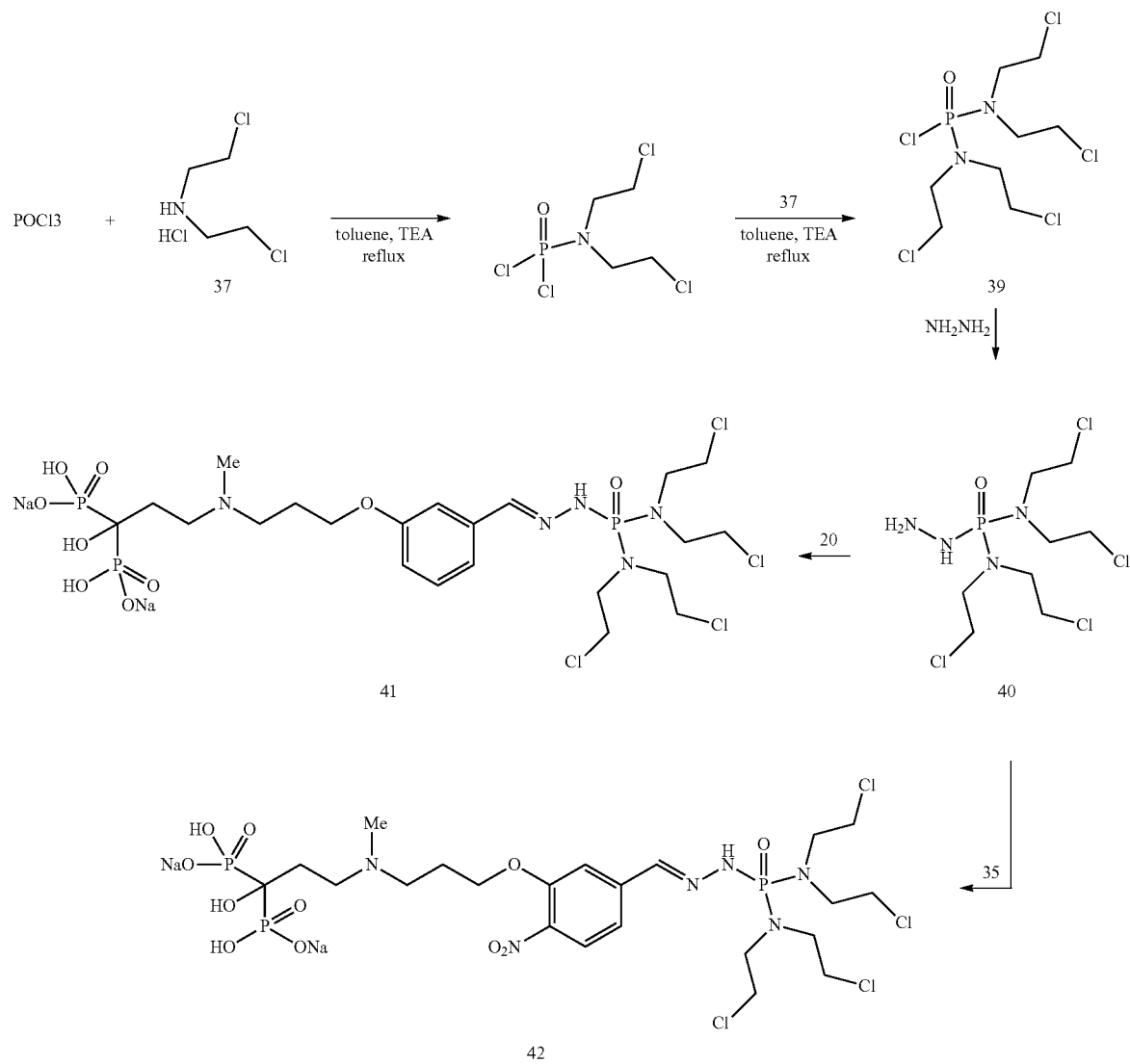

Molecules 41 and 42 were characterized by their 1H and 31P NMR spectra.

Compound 46, bearing a mustard gas residue, was synthesized according to the following reaction diagram, according to protocols described previously:

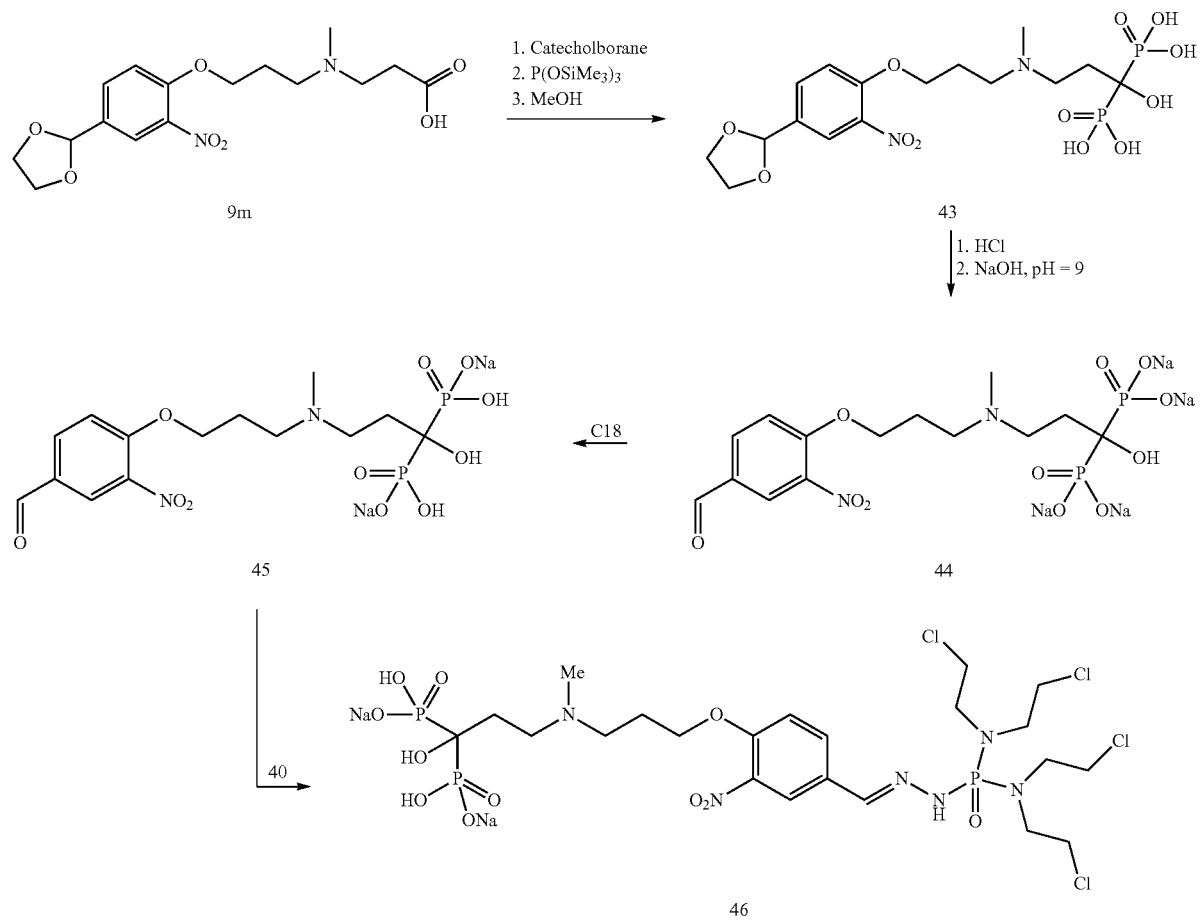

Molecule 46 was characterized by its 1H and 31P NMR spectra.

Molecule 48, bearing a dansyl residue useful for medical imaging by fluorescence, was synthesized according to the following reaction diagram from commercial compound 47, according to protocols described previously.

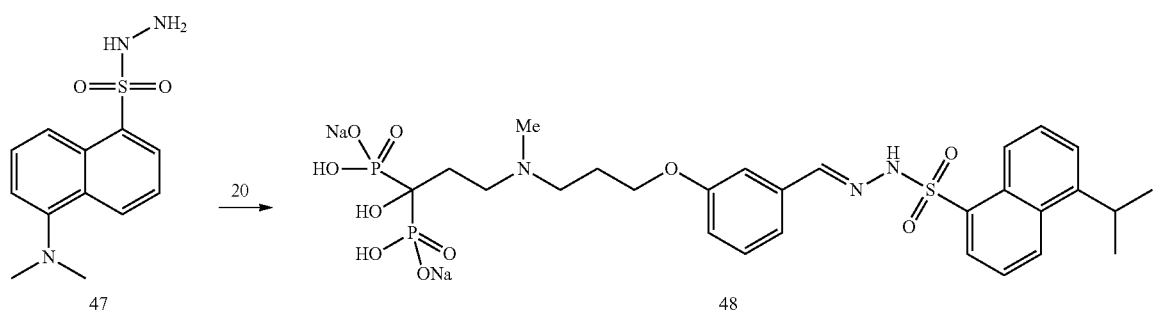

Molecule 48 was characterized by its 1H and 31P NMR spectra.

Molecule 50, bearing a modified fluorescein residue useful for medical imaging by fluorescence, was synthesized according to the following reaction diagram from commercial compound 49, according to protocols described previously:

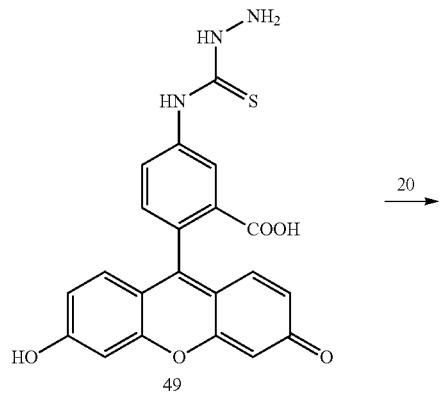

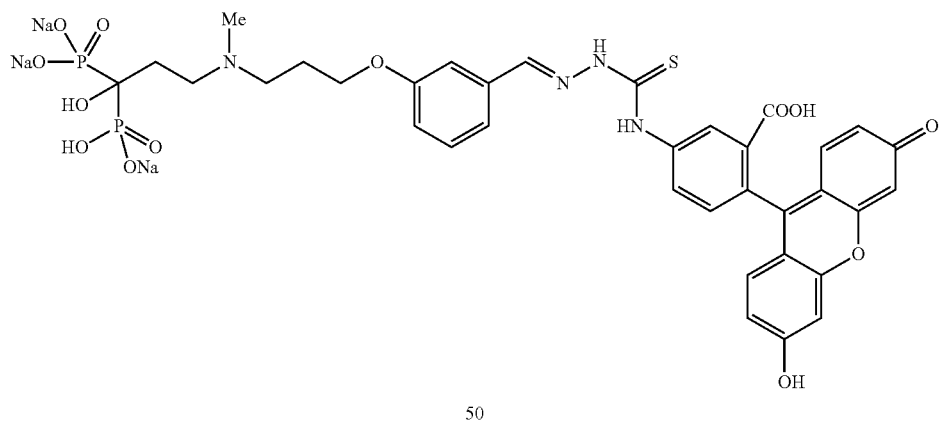

Molecule 50 was characterized by its 1H and 31P NMR spectra.

Molecules 55 and 56, bearing a pyrene residue useful for medical imaging by fluorescence, was synthesized according to the following reaction diagram:

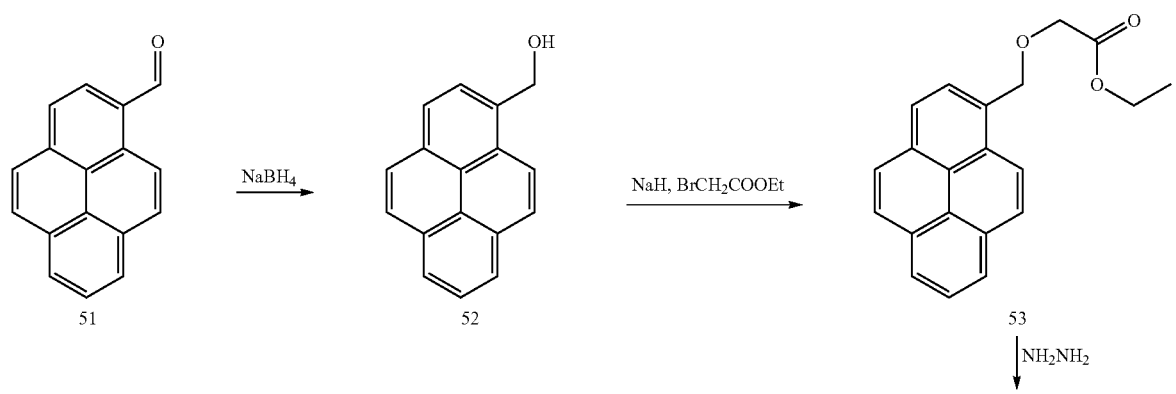

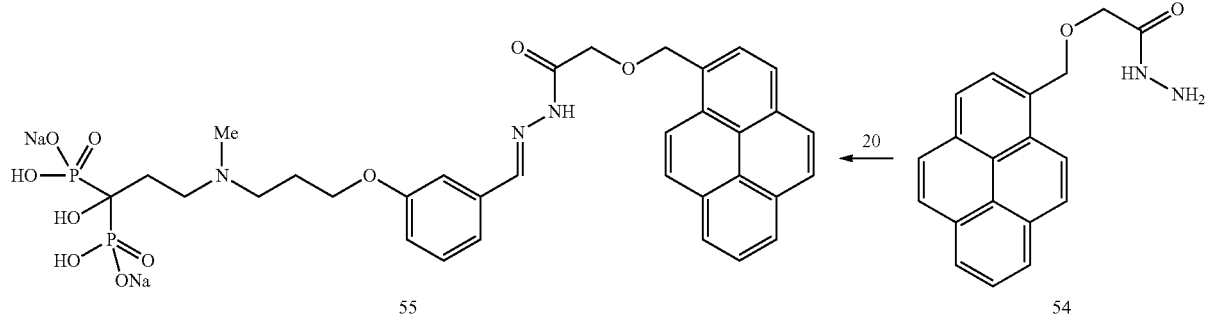

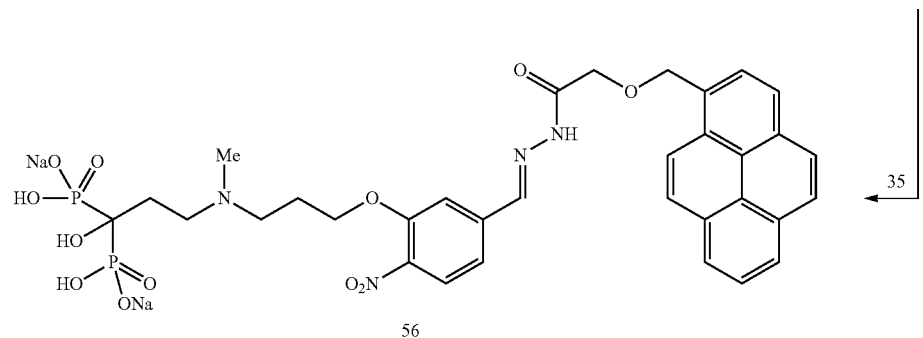

Compound 52:

NaBH$_4$ (124 mg, 3.27 mmol) was added to a solution of commercial compound 51 (250 mg, 1.09 mmol) in MeOH (2 ml). Five min later, the pH was adjusted to 1 with a solution of 1M HCl and the mixture obtained was diluted with water. The precipitate was filtered, washed with water and dried. 250 mg of compound 52 were obtained with yield of 99%.

Compound 54:

NaH (41 mg, 1.03 mmol) was added to a solution of compound 52 (200 mg, 0.862 mmol) in dimethylformamide (3 ml) and the mixture was stirred for 2 min at room temperature. Ethyl bromoacetate (144 μl, 1.03 mmol) was added at the same temperature and stirring was continued for 1 h. NH$_2$NH$_2$.H$_2$O (1 ml) was added and stirring was continued for 2 h at room temperature. Water (40 ml) was added, followed by cyclohexane (40 ml). The precipitate obtained was filtered, washed with MeOH and dried. 102 mg of compound 54 were obtained with yield of 39% (in two steps).

Compounds 55 and 56:

These compounds were obtained from compound 54 by the protocols described previously.

Molecules 55 and 56 were characterized by their 1H and 31P NMR spectra.

Molecule 57, bearing a modified fluorescein residue useful for medical imaging by fluorescence, was synthesized according to the following reaction diagram from commercial compound 49, according to protocols described previously.

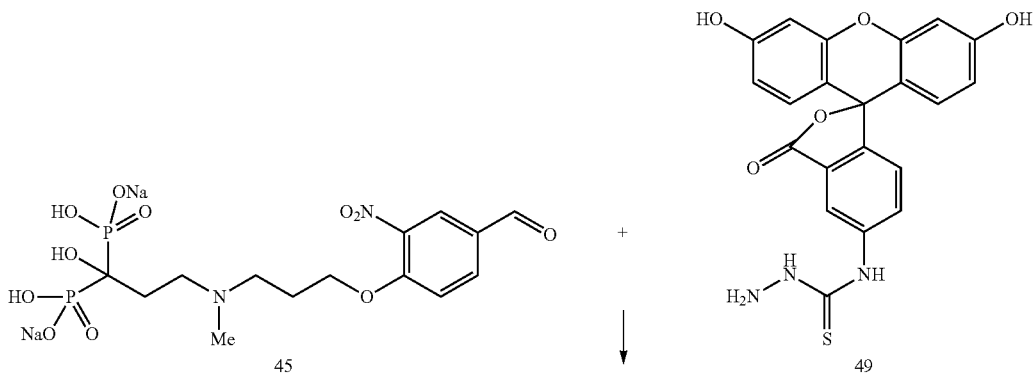

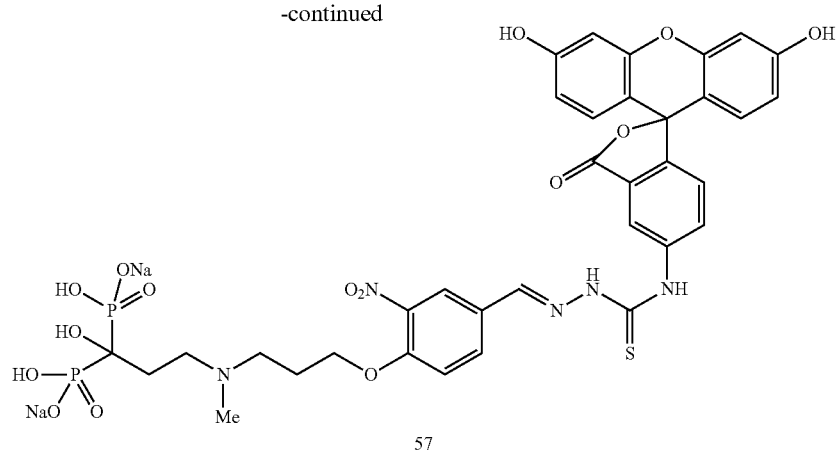

57

Molecule 57 was characterized by its 1H and 31P NMR spectra.

Molecule 58, bearing a modified dansyl residue useful for medical imaging by fluorescence, was synthesized according to the following reaction diagram from commercial compound 47, according to protocols described previously.

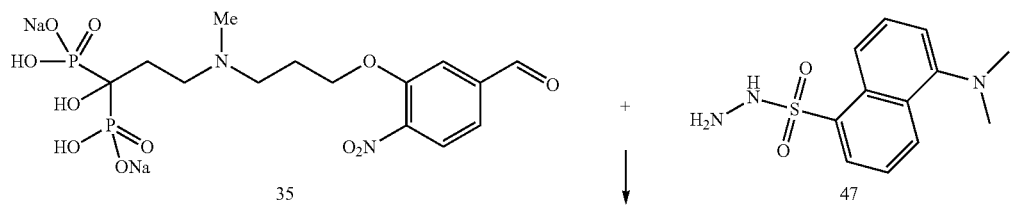

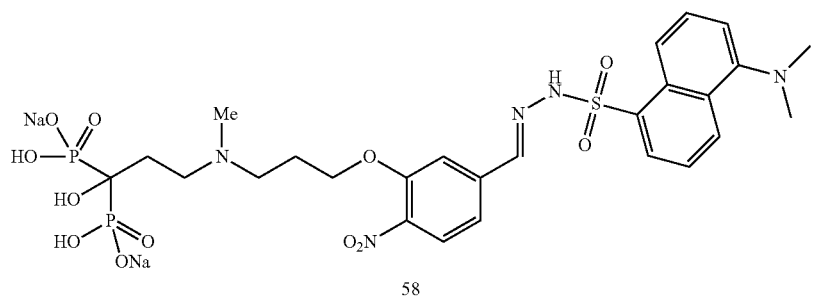

58

Molecule 58 was characterized by its 1H and 31P NMR spectra.

Molecules 59, bearing a rhodamine B residue useful for medical imaging by fluorescence, was synthesized according to the following reaction diagram:

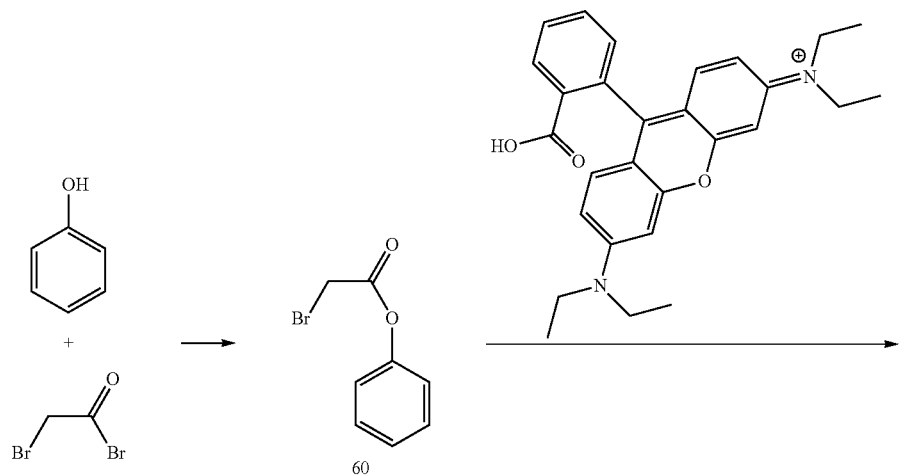
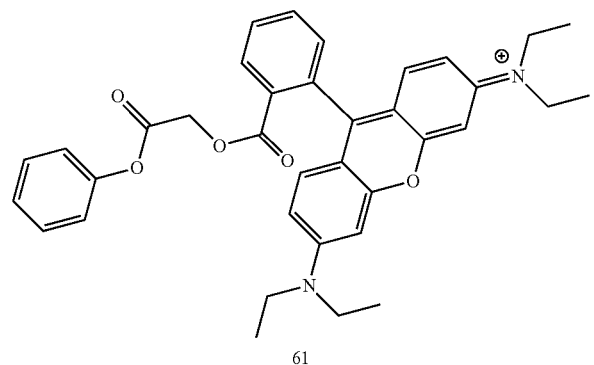
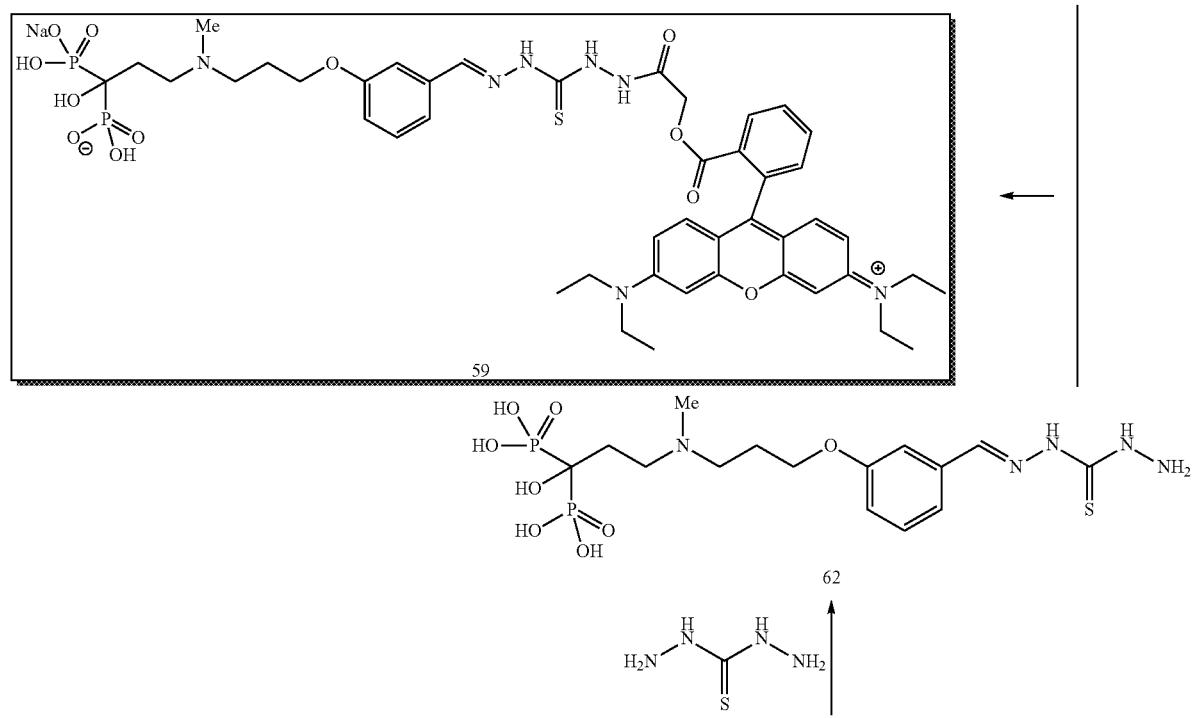

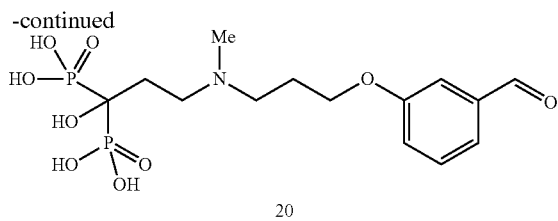

20

Compound 60:
The mixture of phenol (10 g, 106 mmol) and bromoacetic acid bromoanhydride (9.16 ml, 106 mmol) was heated to 90° C. for 10 min then all the volatile components were evaporated to dry at 90° C. under vacuum. 23 g of compound 60 were obtained with a nearly quantitative yield.

Compound 61:
A solution of 60 (0.243 ml, 2.2 mmol) and commercial rhodamine B (884 mg, 2 mmol) in MeNO₂ (5 ml) was stirred at 80° C. for 5 min, then evaporated to dry under vacuum at the same temperature. Compound 61 was thus obtained in the form of an amorphous black solid (1.22 g, yield≅100%).

Compound 62:
A solution of thiocarbohydrazide (233 mg, 2.2 mmol) in NaOH 2M (2 ml) was added to a solution of 20 (100 mg, 0.22 mmol) in water (2 ml). The transparent solution was evaporated at 60° C. to dry. Water (2 ml) was added and the solution was evaporated again at 60° C. to dry. The residue was chromatographed on column C18 to give compound 62, 71 mg, amorphous solid, yield=60%.

Compound 59:
A solution of 62 (10 mg, 0.0184 mmol) and 61 (48 mg, 0.073 mmol) in a mixture of water (1 ml) and THF (1 ml) was stirred for 2 h at 40° C. MeOH followed by Et₂O were then added. The precipitate formed was filtered (14 mg) and chromatographed on column C18. 2 mg of compound 59 were thus obtained, yield=10%.

Molecule 59 was characterized by its 1H and 31P NMR spectra.

Molecule 63, bearing a mustard gas residue, was synthesized according to the following reaction diagram:

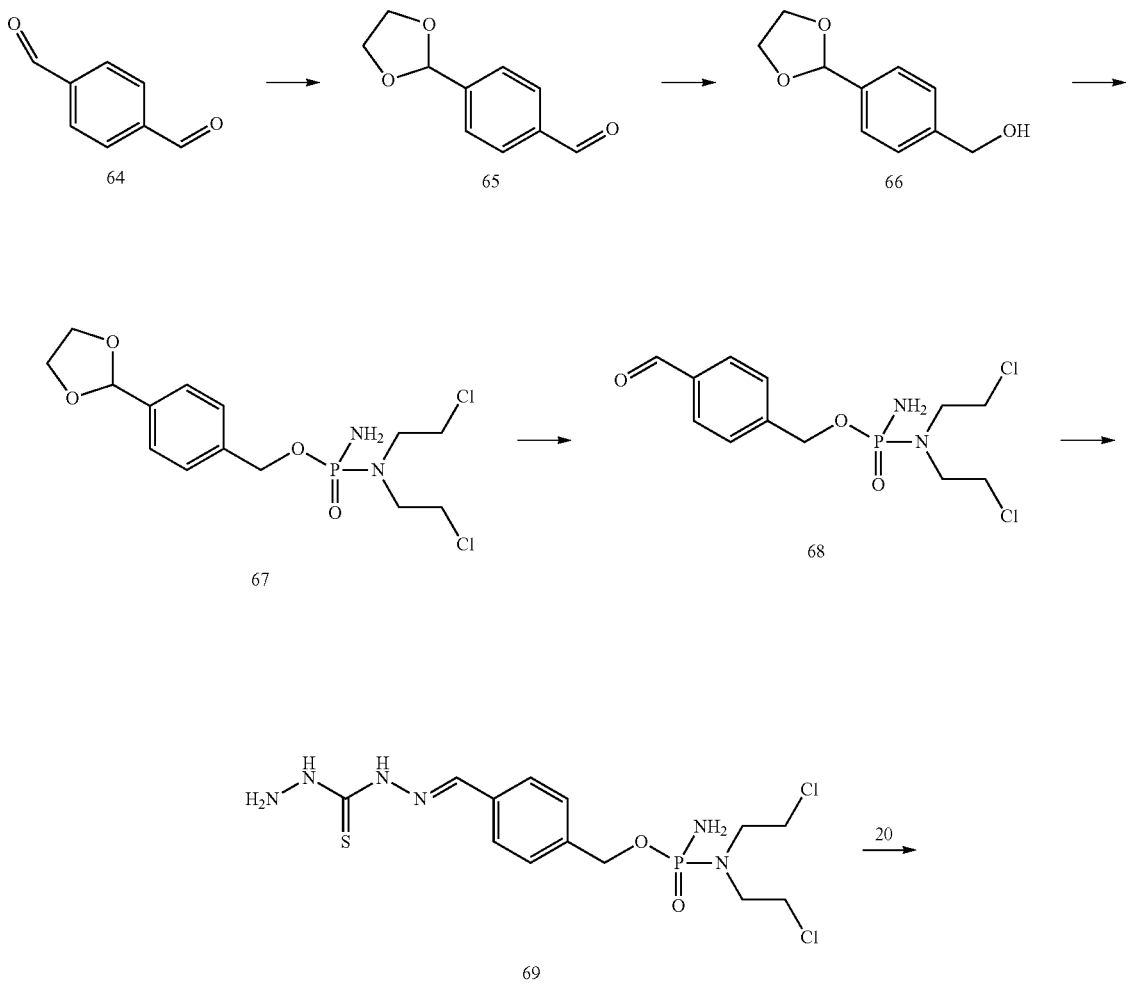

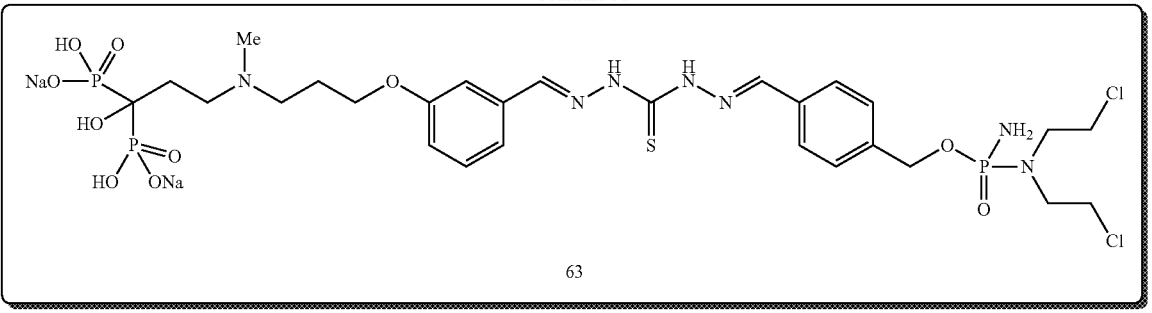

63

Compound 65:
A mixture of 64 (10 g, 74.6 mmol), glycerol (4.6 g, 74.6 mmol) and para-toluene sulfonic acid (710 mg, 3.7 mmol) in benzene was heated under reflux (Dean-Stark) for 5 h, then cooled at RT. An excess of anhydrous $K_2CO_3$ was added, the mixture was well stirred, then filtered through anhydrous $K_2CO_3$, evaporated under vacuum and chromatographed on silica gel. Compound 65 was thus obtained (6.3 g, yield=47%) in the form of a light yellow oil.

Compound 66:
$NaBH_4$ (427 mg, 11.2 mmol) was gradually added to a solution cooled with cold water of 65 (1 g, 5.6 mmol) in MeOH (5 ml) and the mixture obtained was stirred for 5 min at RT. The pH of the mixture was adjusted to 7 with a phosphate buffer. An MeOH: DCM=1:1 mixture was added, followed by anhydrous $Na_2SO_4$ and the final mixture was well stirred, then filtered through anhydrous $Na_2SO_4$ anhydride and concentrated under vacuum. Compound 66 was obtained (980 mg, yield=96%).

Compound 67:
HMDS-Na (2M in THF, 1.67 ml, 3.34 mmol) is added at −120° C. under argon to a solution of 66 (500 mg, 2.78 mmol) in THF (23 ml). After 10 min at −120° C., bis(2-chloroethyl) phosphoramidic dichloride (720 mg, 2.78 mmol) in THF (4 ml) was added all at once. The reaction mixture was heated gradually to RT for 1.5 h, then cooled at −90° C. A solution of ammonia in DCM (1.5 M, 5.7 ml, 8.62 mmol) was added at this temperature. The cold bath was removed, the reaction medium was stirred at RT for 1 h, silica with MeOH was added and the solvent was evaporated under reduced pressure at 40° C. After chromatography on silica (gradient from DCM to DCM:MeOH=5:1) and evaporation of the solvent, compound 67 was obtained (1.03 mg, 96%).

Compound 68:
Compound 67 (1 g, 2.6 mmol) was solubilized in 15 ml of DCM to which 50 ml of $Et_2O$ were added. The solution obtained was well stirred with 2M HCl, washed with water, then with a saturated solution of $NaHCO_3$. The organic phase was dried with anhydrous $Na_2SO_4$ and concentrated under vacuum at 40° C. Compound 68 was obtained (610 mg, 69%).

Compound 69:
A solution of thiocarbohydrazide (400 mg, 3.78 mmol) in 1M NaOH (6 ml) was added to a solution of 68 (128 mg, 0.378 mmol) in MeOH (11 ml) at RT. After 40 min, the mixture was diluted with a saturated solution of NaCl and extracted with DCM (5 times). The organic phase was dried with anhydrous $Na_2SO_4$ and concentrated under vacuum at 40° C. Compound 69 was obtained (50 mg, 31%).

Compound 63:
A solution of 20 (50 mg, 0.11 mmol) in water (1 ml) was added to a solution of 69 (50 mg, 0.117 mmol) in THF (3 ml) at RT. The solution obtained was evaporated under vacuum at 60° C. THF (3 ml) followed by water (0.5 ml) were added to the residue obtained and the mixture was heated 5 min at 60° C. Three drops of 2M NaOH were added to the solution obtained and the reaction mixture (pH=9-10) was left for 16 h at RT. After purification by chromatography on column C18, compound 63 (20 mg, yield=21%) was obtained.

Molecule 63 was characterized by its 1H and 31P NMR spectra.

Molecule 70, bearing an ibuprofen residue, was synthesized according to the following reaction diagram:

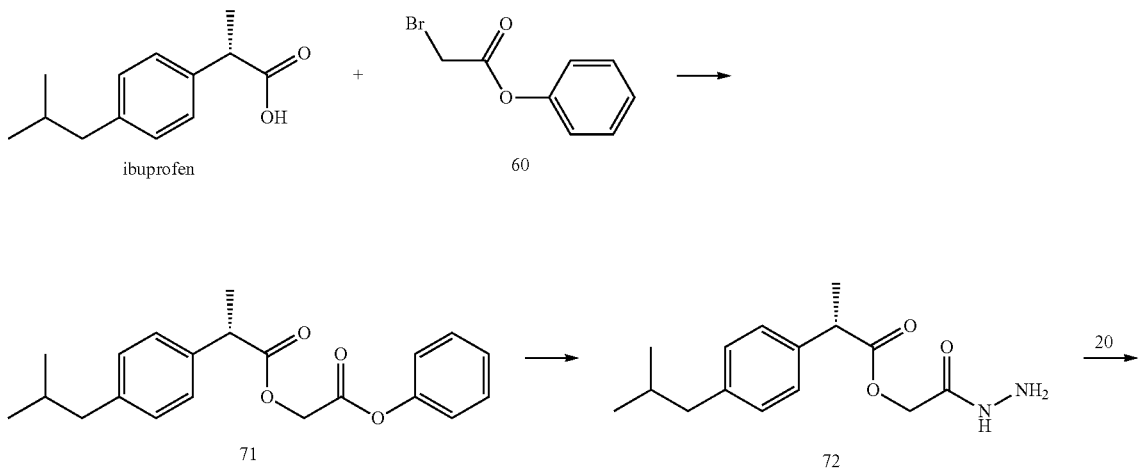

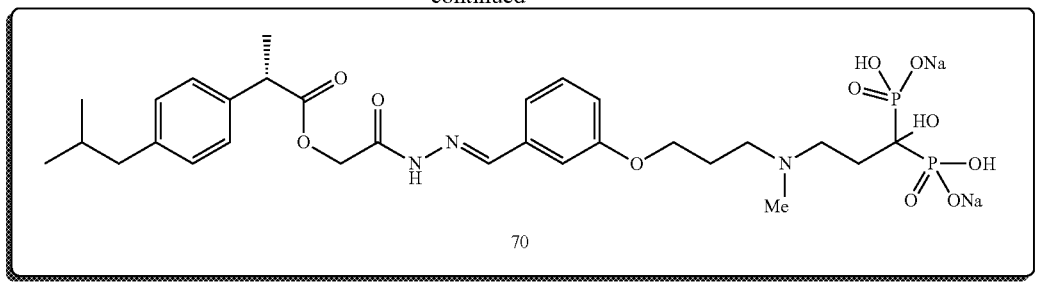

Compound 72:

At RT, compound 60 (312 mg, 1.45 mmol) was added to a mixture of ibuprofen (250 mg, 1.21 mmol) and Na$_2$CO$_3$ (128 mg, 1.21 mmol) in DMF (3 ml) and the mixture obtained was stirred 30 min at RT. DCM (20 ml) were added to this mixture containing crude compound 71 at RT, followed by hydrazine hydrate (1M in MeCN, 3.7 ml, 3.7 mmol), the mixture obtained was stirred for 30 min, then diluted with ether (60 ml), extracted 5 times with 0.1 M NaOH, dried with anhydrous Na$_2$SO$_4$ and concentrated under vacuum at 40° C. Compound 72 (170 mg, yield=51% over two steps) was obtained.

Compound 70:

A solution of 20 (25 mg, 0.0568 mmol) and 72 (19 mg, 0.0681 mmol) in a mixture of H$_2$O:THF=1:1 (3 ml) were evaporated under vacuum at 60° C. The same solubilization/evaporation cycle was repeated twice. After purification by chromatography on column C18, compound 70 (24 mg, yield=49%) was obtained.

Molecule 70 was characterized by its 1H and 31P NMR spectra.

Molecule 73, bearing a methotrexate anticancer product residue, was synthesized according to the following reaction diagram:

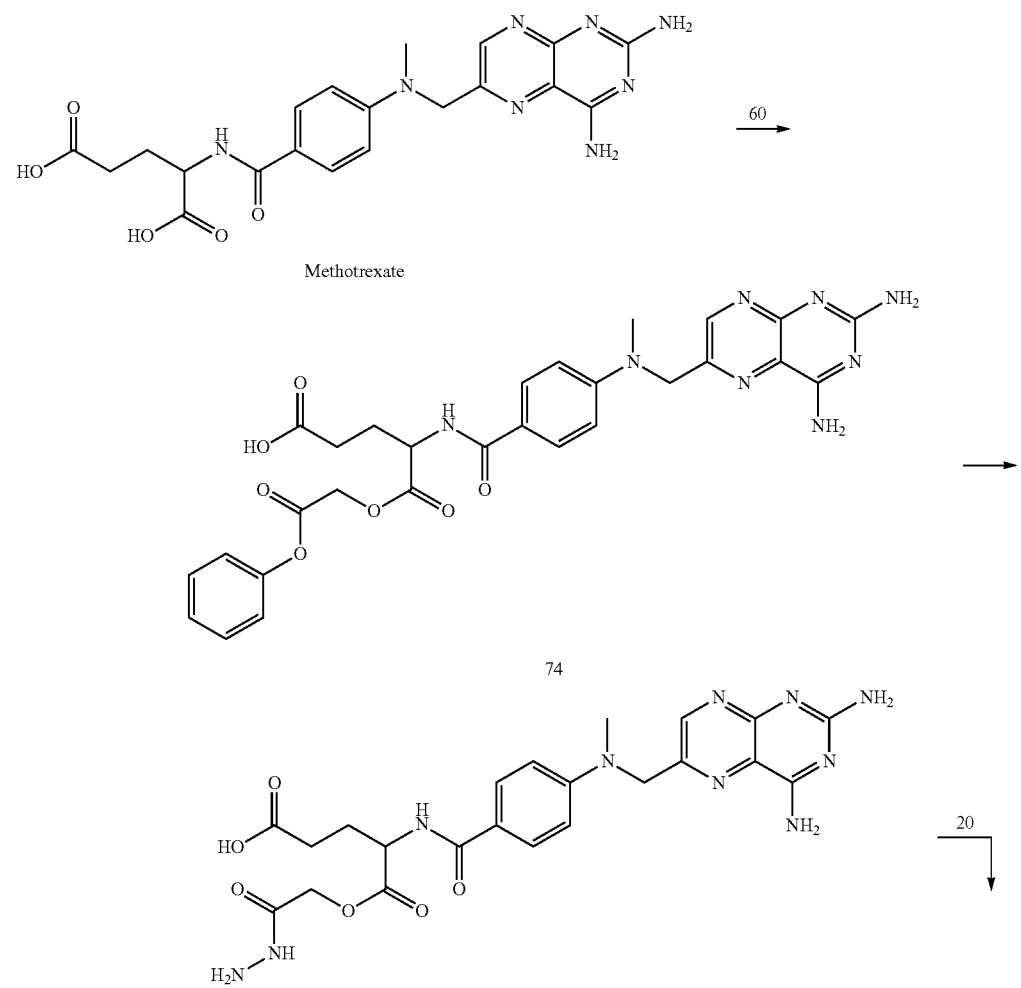

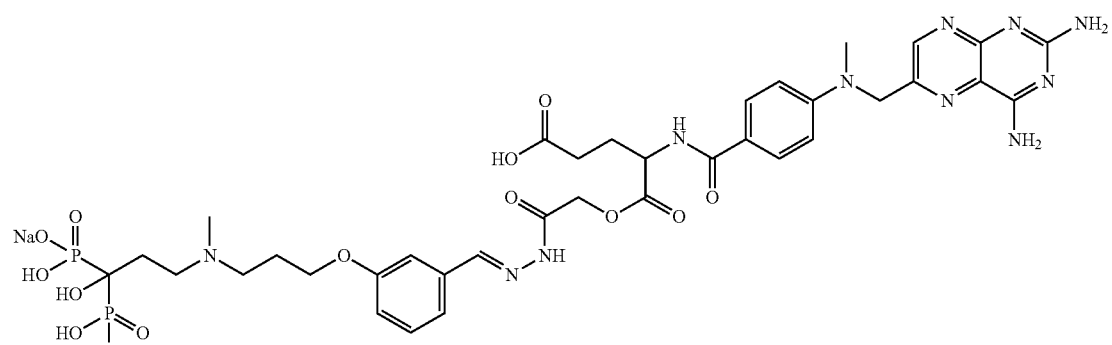

73

Compound 74:

At RT, compound 60 (57 mg, 264 mmol) was added to a mixture of methotrexate (100 mg, 0.22 mmol) and $Na_2CO_3$ (23 mg, 0.22 mmol) in DMF (1 ml) and the mixture obtained was stirred 24 h at RT. This mixture was chromatographed on silica (DCM→MeOH). Compound 74 (45 mg, yield=35%) was obtained.

Compound 75:

A mixture of 74 (40 mg, 0.0679 mmol), MeOH (16 ml), DCM (10 ml), THF (2 ml) and hydrazine hydrate (1M in MeCN, 0.1 ml, 0.1 mmol) was evaporated at 40° C. under vacuum. The residue was solubilized in 1 ml of water with MeOH, then with an excess of $Et_2O$. The precipitate obtained was filtered, washed with $Et_2O$ and dried. Compound 75 (30 mg, yield=84%) was obtained.

Compound 73:

A solution of 20 (32 mg, 0.0712 mmol) and 75 (25 mg, 0.0474 mmol) in a mixture of $H_2O$:THF=1:1 (3 ml) were evaporated under vacuum at 60° C. The same solubilization/evaporation cycle was repeated twice. After purification by chromatography on column C18, compound 73 (23 mg, yield=50%) was obtained.

Molecule 73 was characterized by its 1H and 31P NMR spectra.

Molecule 80, bearing a methotrexate anticancer product residue, was synthesized according to the following reaction diagram:

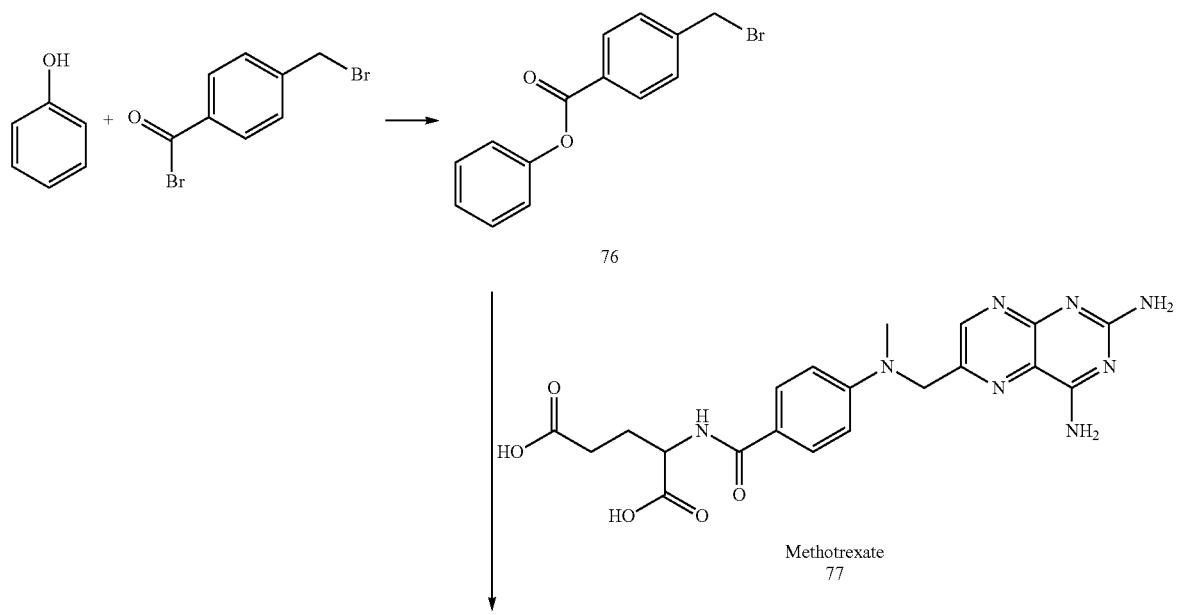

-continued
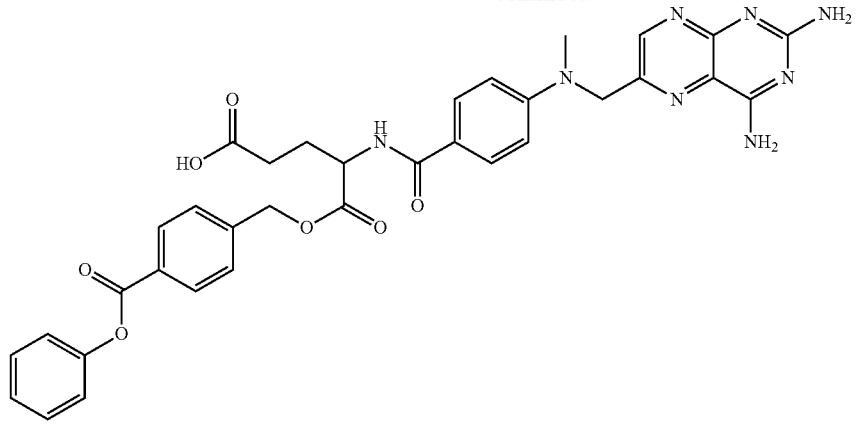
78
↓ 20
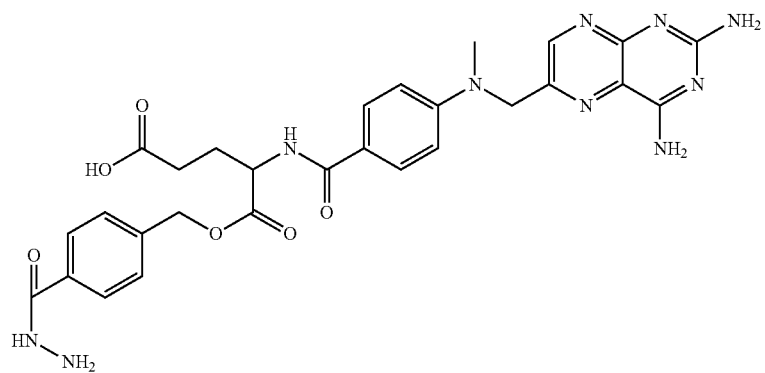
79
↓
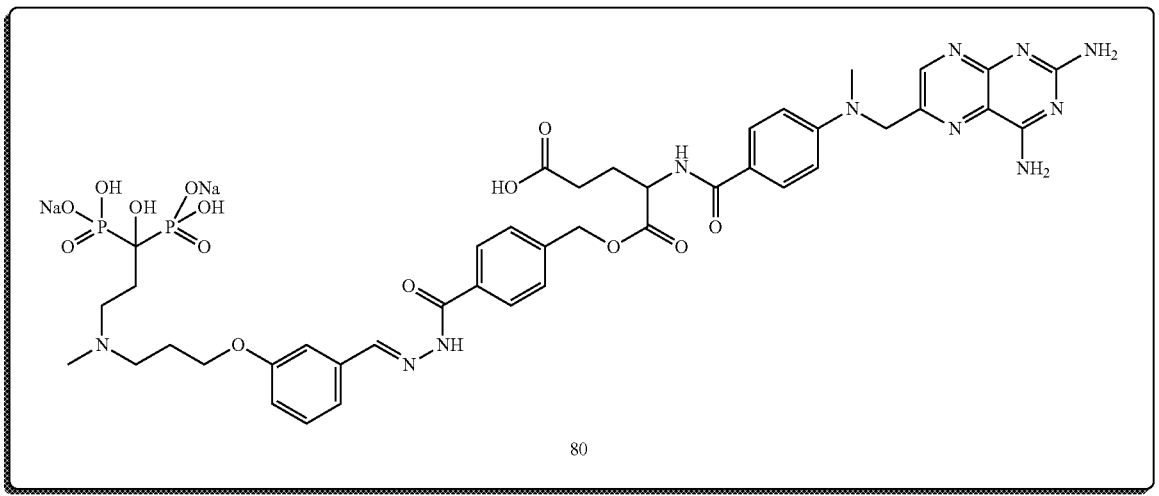
80

Compound 76:

It was prepared in the same way as compound 60. The final crystalline product was obtained with a nearly quantitative yield.

Compound 78:

It was prepared in the same way as compound 74 starting from compounds 76 and 77, with a yield of 38%. Molecule 78 was characterized by its 1H NMR spectrum.

Compound 79:

It was prepared in the same way as compound 75 starting from compounds 78, with a yield of 77%. Molecule 79 was characterized by its 1H NMR spectrum.

Compound 80:

It was prepared in the same way as compound 73 starting from compounds 79 and 20, with a yield of 65%. Molecule 80 was characterized by its mass, 1H NMR and 31P NMR spectra.

Molecule 90, bearing a methotrexate anticancer product residue, was synthesized according to the following reaction diagram:

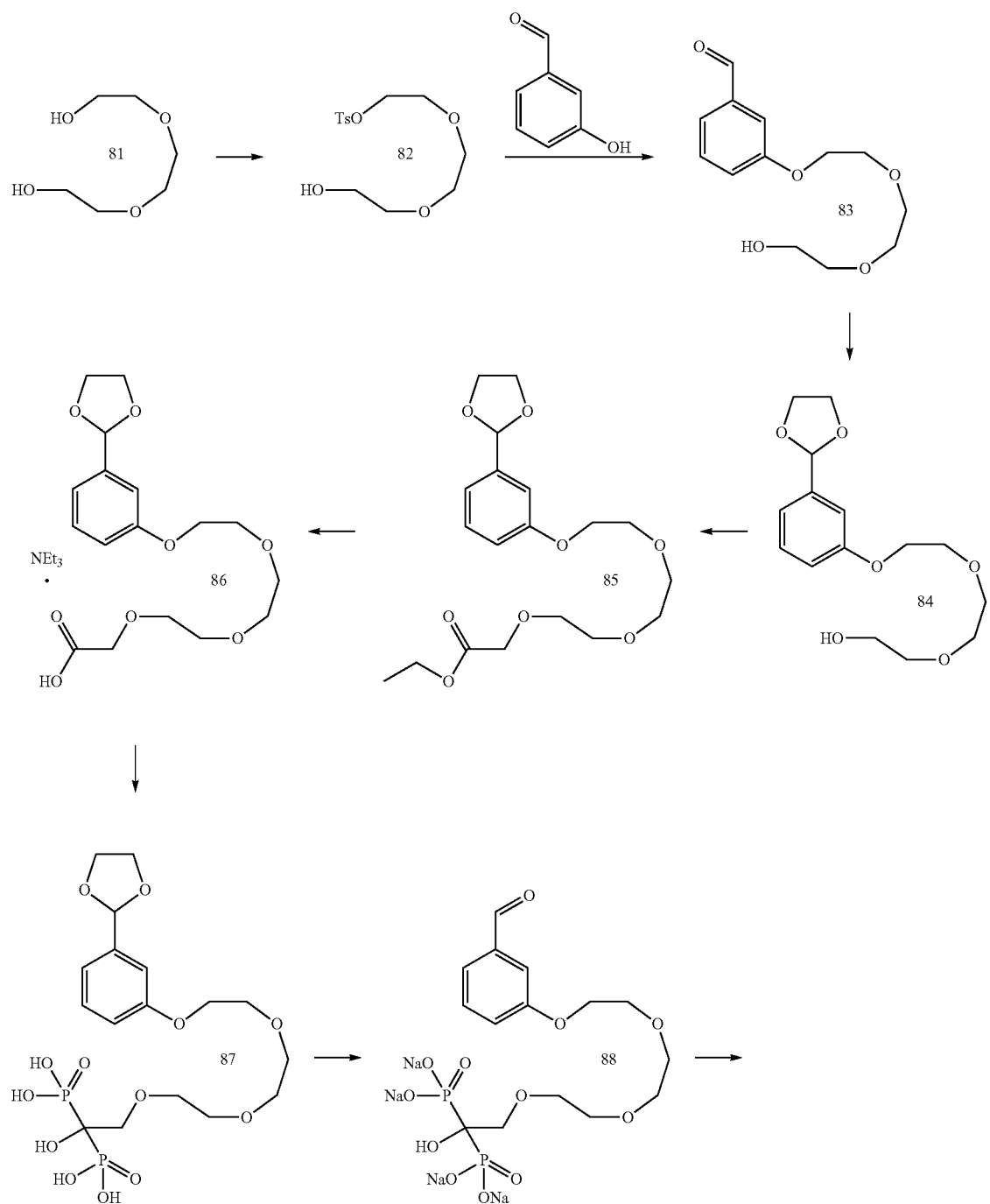

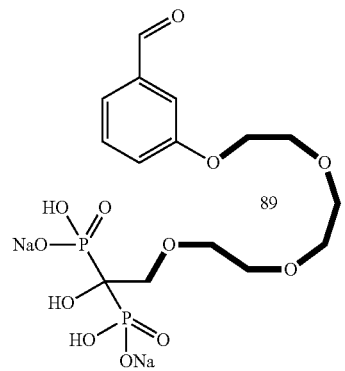

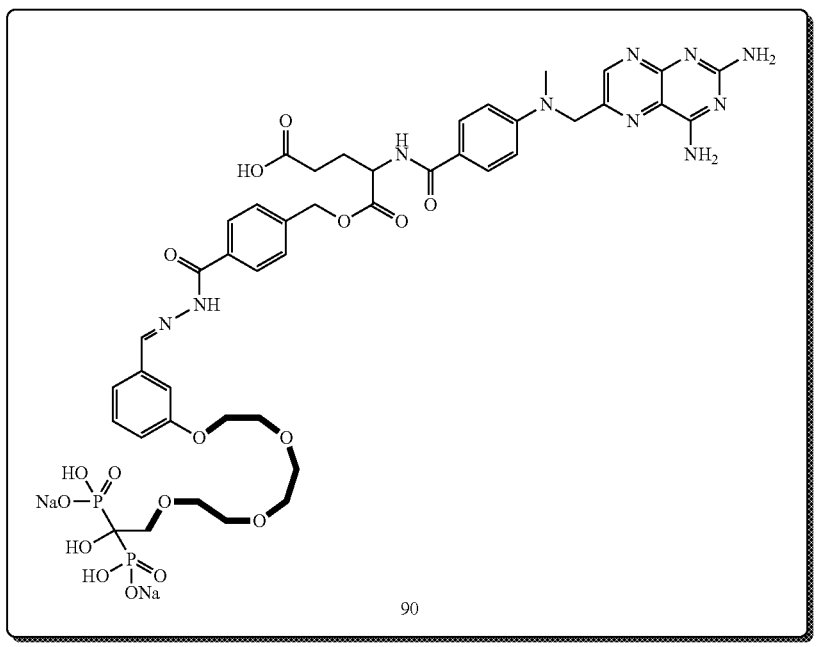

Compound 83:

Tosyl chloride TsCl (1.01 g, 5.3 mmol) was added to the mixture of compound 81 (4.7 ml, 6 eq.) and K$_2$CO$_3$ (814 mg, 5.9 mmol) stirred 3 min at 80° C. and the mixture obtained was stirred 5 min more. Then the dry mixture of K$_2$CO$_3$ (814 mg, 5.9 mmol), 3-hydroxybenzaldehyde (500 mg, 4.1 mmol) and NaI (73 mg) was added and the mixture obtained was stirred 16 h at 80° C. A 2M solution of NaOH (1 ml) was added and the mixture was stirred 10 min at room temperature. After extraction with DCM-H$_2$O—NaCl—NaOH, the organic solution was dried with Na$_2$SO$_4$ and concentered under vacuum. Pure compound 83 was obtained (800 mg) with a yield of 77%. Molecule 83 was characterized by its 1H NMR spectrum.

Compound 84:

Anhydrous Na$_2$SO$_4$ (2.5 g) was added to a solution of compound 83 (800 mg, 3.15 mmol) in benzene (10 ml). Pyridine (12 μl, 0.158 mmol), PTSA.H$_2$O (30 mg, 0.158 mmol) and ethylene glycol (578 μl, 10.4 mmol) were added to this solution and the mixture obtained was stirred at 77° C. for 3 h. K$_2$CO$_3$ (1 g) was added and after 15 min of stirring and cooling, the mixture was filtered through K$_2$CO$_3$ that had been washed with Et$_2$O. After concentration under vacuum, pure compound 84 was obtained (750 mg) with a yield of 80%. Molecule 84 was characterized by its 1H NMR spectrum.

Compound 85:

NaH (60% in mineral oil, 403 mg, 10.08 mmol) was added to a solution of compound 84 in DMF (10 ml) and the mixture was stirred 5 min at room temperature. An ethyl bromoacetate (1.12 ml, 10.08 mmol) was added and the mixture was stirred 4 h at room temperature. Methanol (2 ml) was added. The solution obtained was introduced onto a silica gel column (160 g) and eluted with a cyclohexane-DCM gradient. The organic solution was dried under vacuum (80° C., 40 mbar, 30 min). Compound 85 was obtained (1.1 g) with a yield of 71%. Molecule 85 was characterized by its 1H NMR spectrum.

Compound 86:

A solution of compound 85 (540 mg, 1.41 mmol) and NaOH (2M, 0.6 ml) in MeOH (2 ml) was stirred 40 min at room temperature, then chromatographed on silica gel (40 g, eluent: gradient from DCM to DCM:MeOH:TEA=2:1:0.2). The organic solution was concentrated under vacuum at 40° C. the co-evaporated three times with THF at the same temperature Compound 86 was obtained (348 mg) with a yield of 66%. Molecule 86 was characterized by its 1H NMR spectrum.

Compound 89:

Catecholborane (0.3 ml, 1M/THF, 0.3 mmol) was added to a solution of compound 86 (60 mg, 0.14 mmol) and TEA (5.8 µl, 0.086 mmol) in THF (360 µl), with stirring, at room temperature, under argon (hydrogen release). Three minutes later, tris(trimethylsilyl)phosphite (150 mg, 0.5 mmol) was added at once and stirring was continued for 3 h at room temperature. MeOH (0.4 ml) was added and the mixture was stirred for 15 min. Next, an excess of ether was added and after stirring, a colorless oil was separated, washed with ether, dried under vacuum and dissolved in 1 ml of water and $HCl_{conc.}$ (0.25 ml) at room temperature. After 30 min, the solution was basified to pH=14 with concentrated NaOH, then the pH was adjusted to 7 with a phosphate buffer and the solution obtained was chromatographed (C18, 3% MeOH/$H_2O$). 15 mg of pure compound 86 were obtained with yield of 21%. The molecule was characterized by its mass, 1H NMR and 31P NMR spectra.

Compound 90:

It was prepared in the same way as compound 73 starting from compounds 79 and 89, and was characterized.

Molecule 94, bearing a doxorubicin anticancer product residue, was synthesized according to the following reaction diagram:

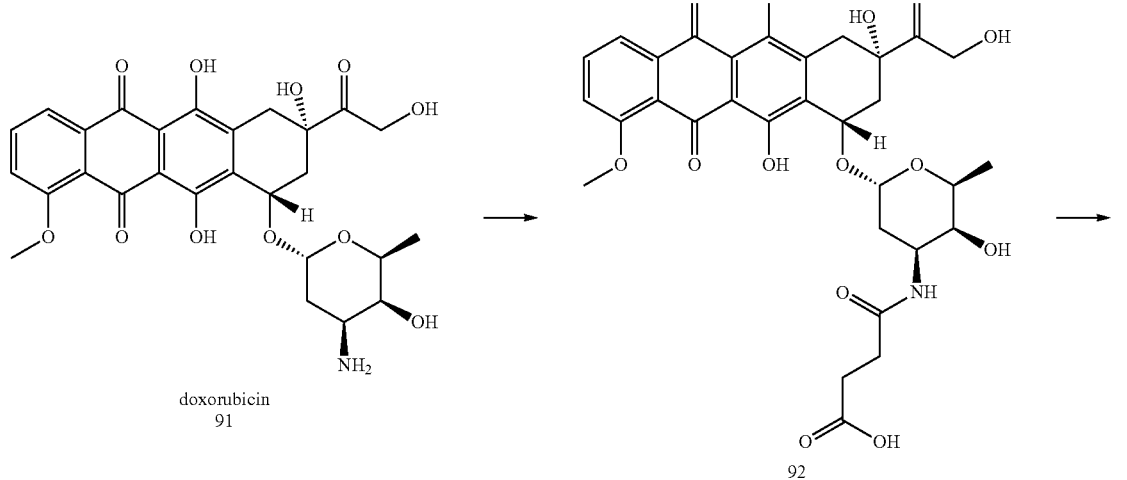

doxorubicin
91

92

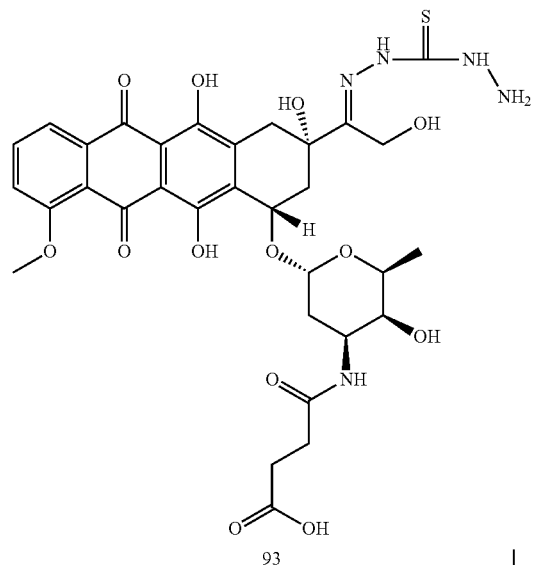

93

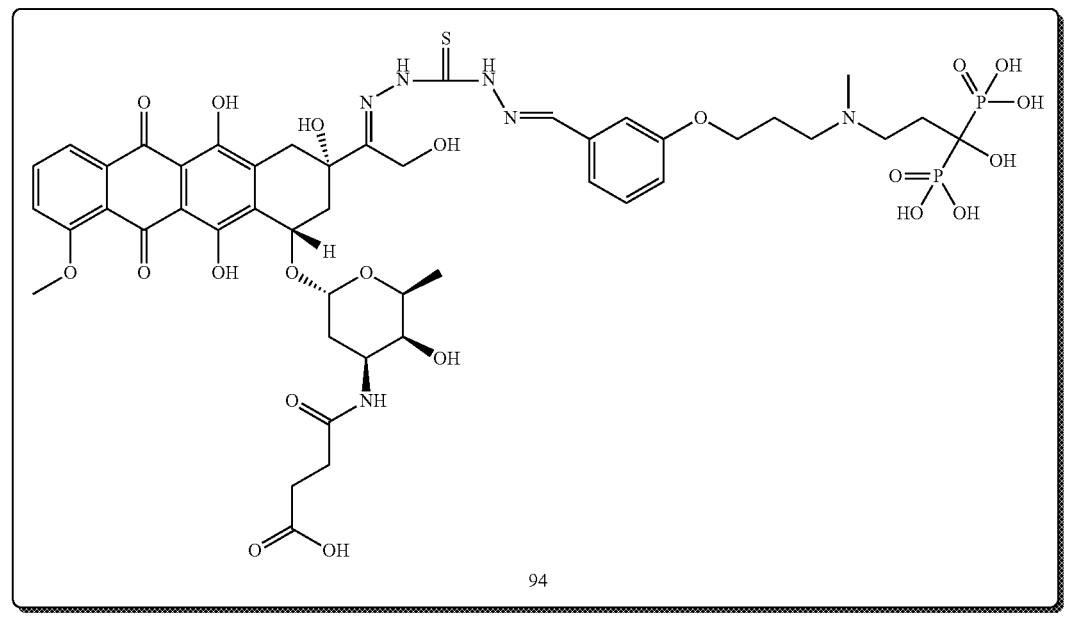

94

Compound 92:
Succinic anhydride (8.6 mg, 0.086 mmol) was added to a mixture of doxorubicin (50 mg, 0.086 mmol) and TEA (0.1 ml) in DMF (2 ml) and the mixture obtained was stirred 10 min at room temperature then chromatographed on silica gel (eluent: gradient from DCM to MeOH). Pure compound 92 was obtained (53 mg) with a yield of 96%. Molecule 92 was characterized by its mass and 1H NMR spectra.

Compound 93:
A solution of compound 92 (50 mg, 0.078 mmol) and thiocarbohydrazide (55 mg, 0.52 mmol) in a mixture of MeOH:TFA 1000:1 was stirred 16 h at room temperature, then chromatographed on silica gel (eluent: gradient from DCM to DCM:MeOH=1:1). Compound 93 was obtained (53 mg) with a yield of 95%.

Compound 94:
A solution of compound 93 (10 mg, 0.0137 mmol), compound 20 (8 mg, 0.0176 mmol) and 4 drops of AcOH in a water:THF=1:1 mixture (4 ml) was stirred 16 h at room temperature, then THF was eliminated under vacuum at room temperature and the precipitate formed was filtered, washed with water, MeOH and Et$_2$O and dried. Compound 94 was obtained (8 mg) with a yield of 52%. Molecule 94 was characterized by its mass, 1H NMR and 31P NMR spectra.

Molecule 99, bearing a SN38 anticancer product residue, was synthesized according to the following reaction diagram:

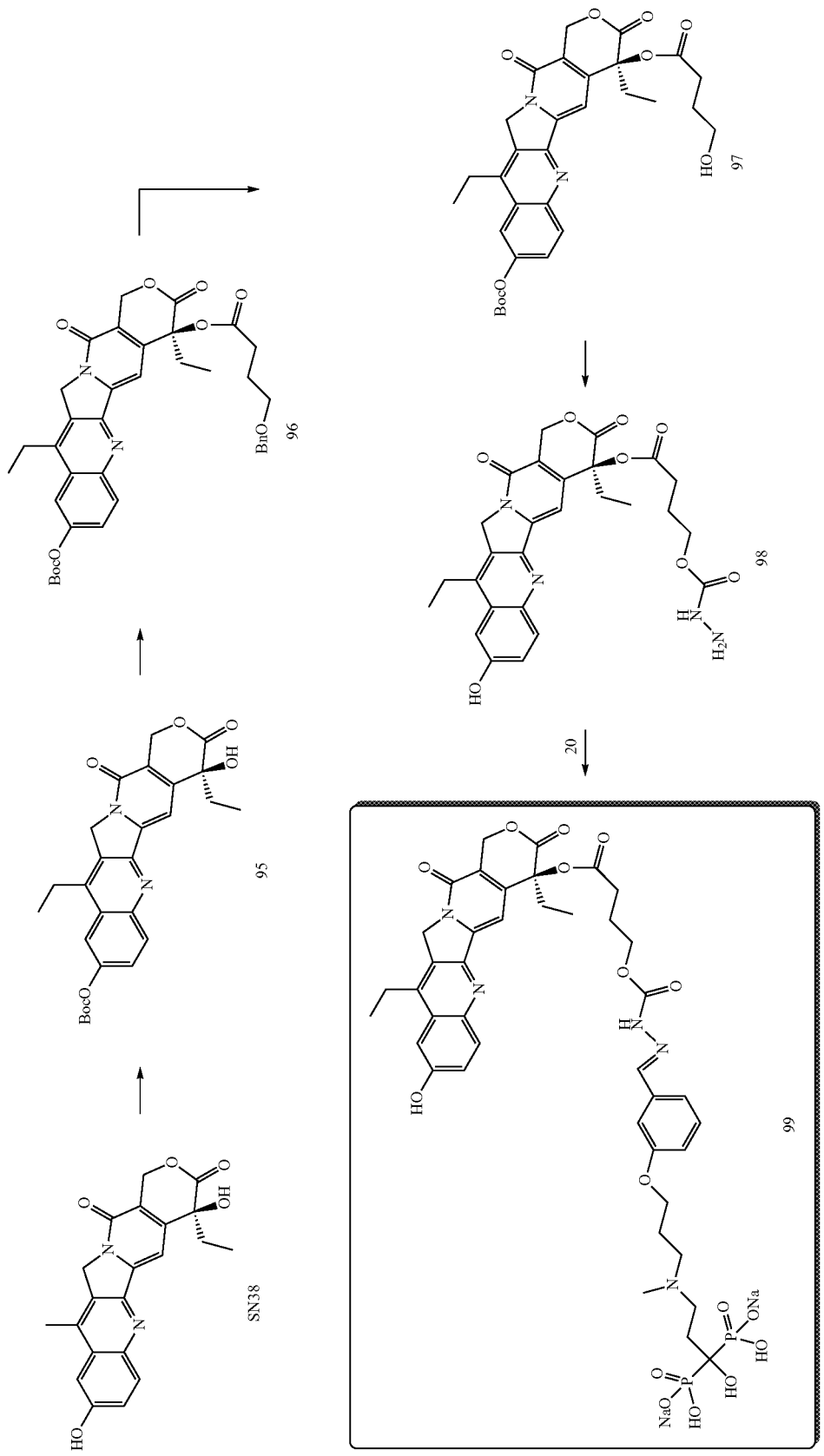

Compound 95:

Compound 95 was synthesized according to the operating procedure described in *Bioconjugate Chem.* 19, 4, 2008, 849-859.

Compound 96:

4-benzyloxybutyric acid (460 mg, 2.43 mmol), DMAP (100 mg, 0.81 mmol) and EDCI (460 mg, 2.43 mmol) were added to a solution of compound 95 (400 mg, 0.81 mmol) in DCM (20 ml). The mixture obtained was stirred 2 h at room temperature. Water was added, the organic phase was dried ($Na_2SO_4$) and evaporated under vacuum. The residue was chromatographed on silica gel (eluent: DCM→MeOH). Compound 96 (375 mg, yield=70%) was obtained. Molecule 96 was characterized by its 1H NMR spectrum.

Compound 97:

Cyclohexene (4 ml) and 10% palladium on charcoal (100 mg) were added to a solution of compound 96 (375 mg, 0.56 mmol) in a mixture dioxane/EtOH (20 ml). The mixture obtained was stirred 24 h at 80° C. then filtered on Celite and evaporated under vacuum. The residue was chromatographed on silica gel (eluent: DCM→MeOH). Compound 97 (100 mg, yield=30%) was obtained. Molecule 97 was characterized by its 1H NMR spectrum.

Compound 98:

CDI (210 mg, 1.29 mmol) was added to a solution of compound 97 (150 mg, 0.26 mmol) in THF (10 ml). The solution was stirred 20 minutes at room temperature, then hydrazine hydrate (1M in MeCN, 2.6 ml, 2.6 mmol) was added and the mixture was stirred 2 h at room temperature. This mixture was chromatographed on silica gel (eluent: DCM→MeOH). Compound 98 (80 mg, yield=57%) was obtained. Molecule 98 was characterized by its 1H NMR spectrum.

Compound 99:

In solution of compound 20 (18 mg, 0.040 mmol) and 98 (24 mg, 0.044 mmol) in a mixture of $H_2O$:THF=1:1 (2 ml) were evaporated under vacuum at 60° C. The same solubilization/evaporation cycle was repeated twice. After purification by chromatography on column C18, compound 99 (10 mg, yield=25%) was obtained. Molecule 99 was characterized by its mass, 1H NMR and 31P NMR spectra.

Molecule 102, bearing a chlorambucil anticancer product residue, was synthesized according to the following reaction diagram:

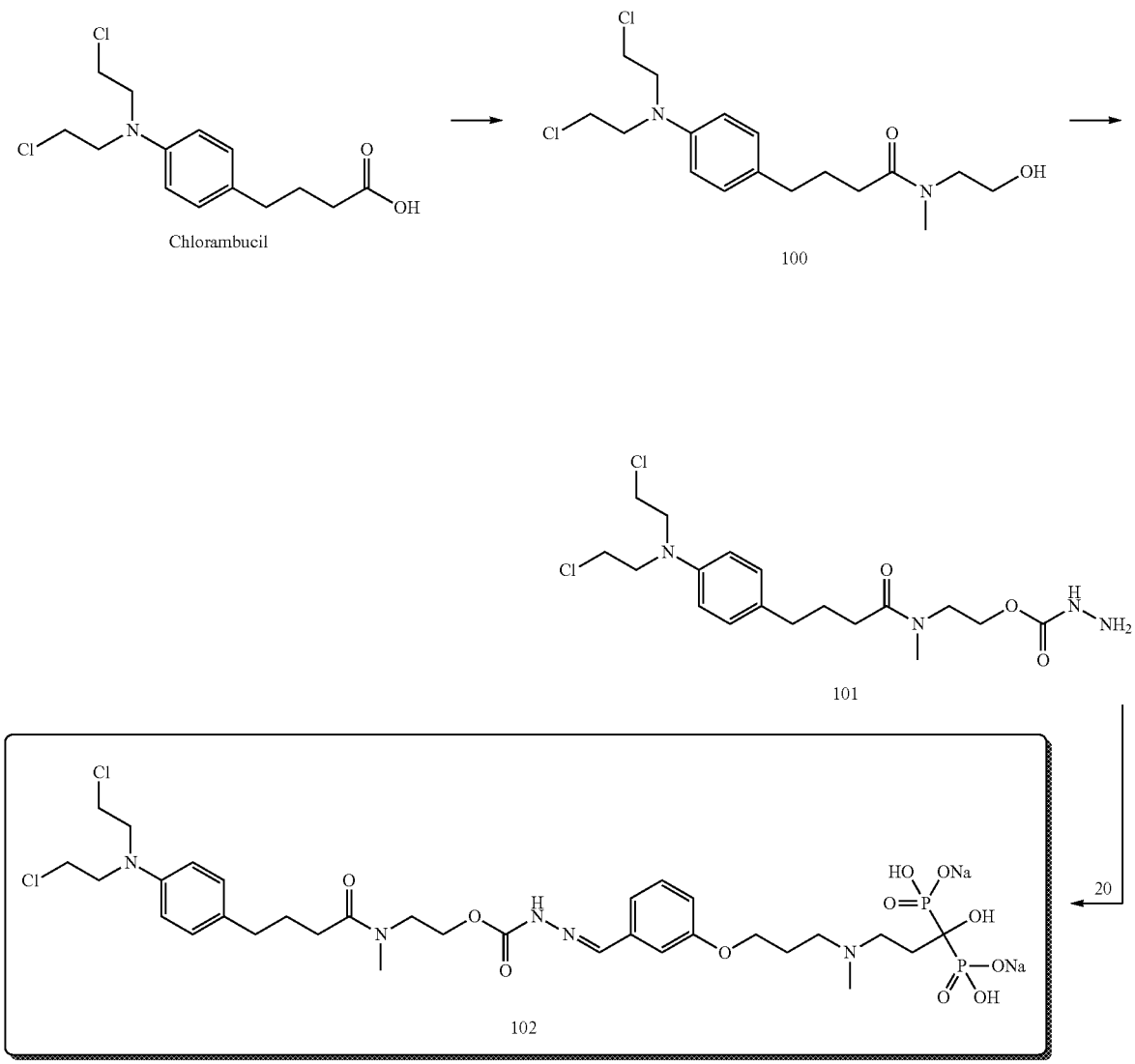

Compound 100:

2-methylaminoethanol (195 mg, 2.6 mmol), Et₃N (0.54 ml, 3.9 mmol), HOBt (350 mg, 2.6 mmol) and EDCI (500 mg, 2.6 mmol) were added to a solution of chlorambucil (400 mg, 1.3 mmol) in DCM (20 ml). The mixture obtained was stirred 24 h at room temperature. Water was added, the organic phase was dried (Na₂SO₄) and evaporated under vacuum. The residue was chromatographed on silica gel (eluent: DCM→MeOH). Compound 100 (375 mg, yield=80%) was obtained. Molecule 100 was characterized by its 1H NMR spectrum.

Compound 101:

CDI (448 mg, 2.77 mmol) was added to a solution of compound 100 (200 mg, 0.55 mmol) in THF (10 ml). The solution was stirred 20 minutes at room temperature, then hydrazine hydrate (1M in MeCN, 3.8 ml, 3.8 mmol) was added and the mixture was stirred 2 h at room temperature. This mixture was chromatographed on silica gel (eluent: DCM→MeOH). Compound 101 (100 mg, yield=43%) was obtained. Molecule 101 was characterized by its 1H NMR spectrum.

Compound 102:

In solution of compound 20 (27 mg, 0.059 mmol) and compound 101 (30 mg, 0.071 mmol) in a mixture of H₂O:THF=1:1 (2 ml) were evaporated under vacuum at 60° C. The same solubilization/evaporation cycle was repeated twice. After purification by chromatography on column C18, compound 102 (13 mg, yield=25%) was obtained. Molecule 102 was characterized by its mass, 1H NMR and 31P NMR spectra.

Molecule 104, bearing an estrone hormonal product residue, was synthesized according to the following reaction diagram:

Compound 103:

A mixture of estrone (50 mg, 0.183 mmol) and thiocarbohydrazide (97 mg, 0.916 mmol) was solubilized in a mixture of 2M NaOH (1 ml) and MeOH (1 ml) at 90° C. and stirred 5 min at this temperature, then cooled and chromatographed on silica gel (eluent: gradient from DCM to MeOH). Pure compound 103 was obtained (60 mg, yield=92%). Molecule 103 was characterized by its mass and 1H NMR spectra.

Compound 104:

A mixture of compound 103 (55 mg, 0.153 mmol) and compound 20 (80 mg, 0.153 mmol) was solubilized in a mixture of water (1 ml) and THF (2 ml) at room temperature and stirred 16 h at this temperature, then co-evaporated four times to dry at 80° C. with a THF-water mixture and chromatographed on C18. Pure compound 104 was obtained (28 mg, yield=92%). Molecule 104 was characterized by its mass, 1H NMR and 31P NMR spectra.

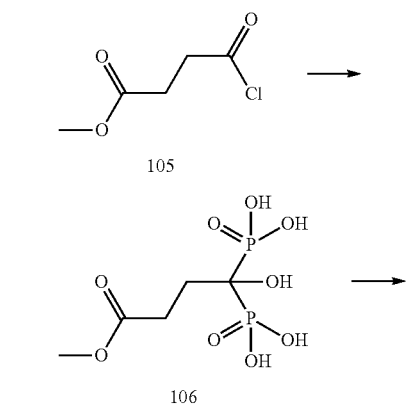

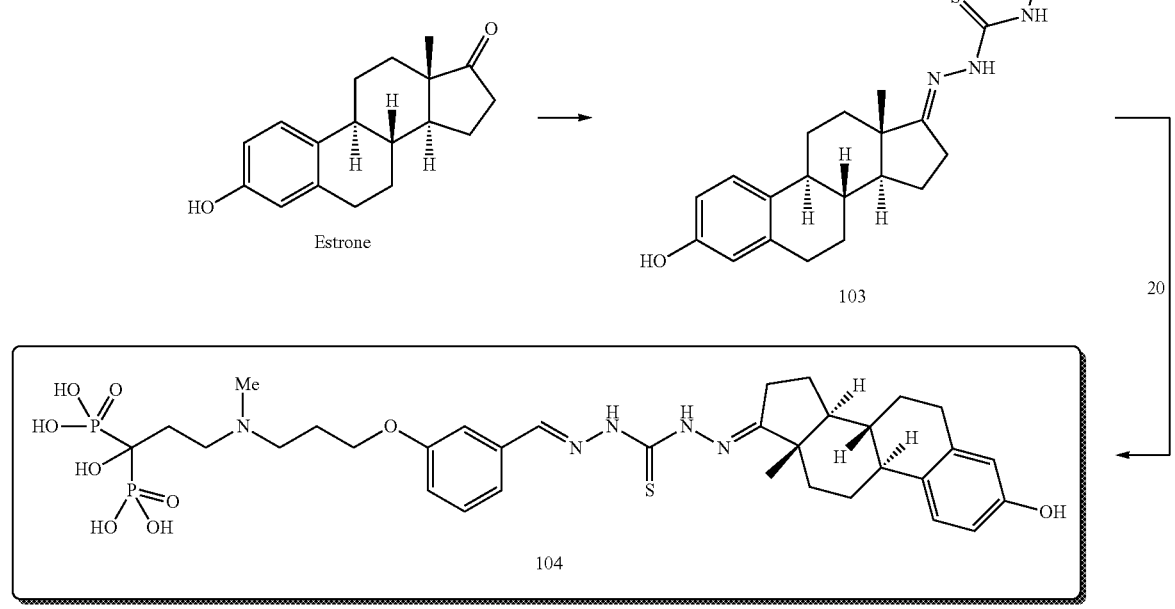

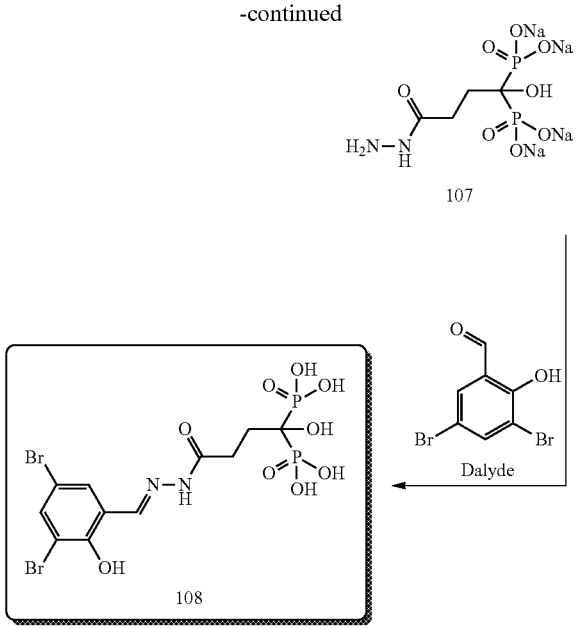

Compound 107:

The mixture of 105 (166 μl, 1.34 mmol) and tris(trimethylsilyl)phosphite (800 mg, 2.68 mmol) was stirred for 30 min under Ar, then MeOH (2 ml) was added and the mixture was stirred 15 min then concentrated to dry at 60° C. The crude product obtained was dissolved in $NH_2NH_2 \cdot H_2O$ and stirred 3 h at RT. 2 eq. of NaOH were added, followed by MeOH and the precipitate formed was filtered, redissolved in 2 ml of water and crystallized MeOH then filtered. The product obtained was solubilized in water (3 ml), 3 eq. of NaOH were added and then the solution was freeze dried. Thus, pure compound 107 was obtained, 230 mg, yield=93%. Molecule 107 was characterized by its mass, 1H NMR and 31P NMR spectra.

Compound 108:

It was prepared in the same way as compound 73 starting from compound 107 and Dalyde and was characterized.

Molecule 111, bearing a benzocaine local anesthetic residue, was synthesized according to the following reaction diagram:

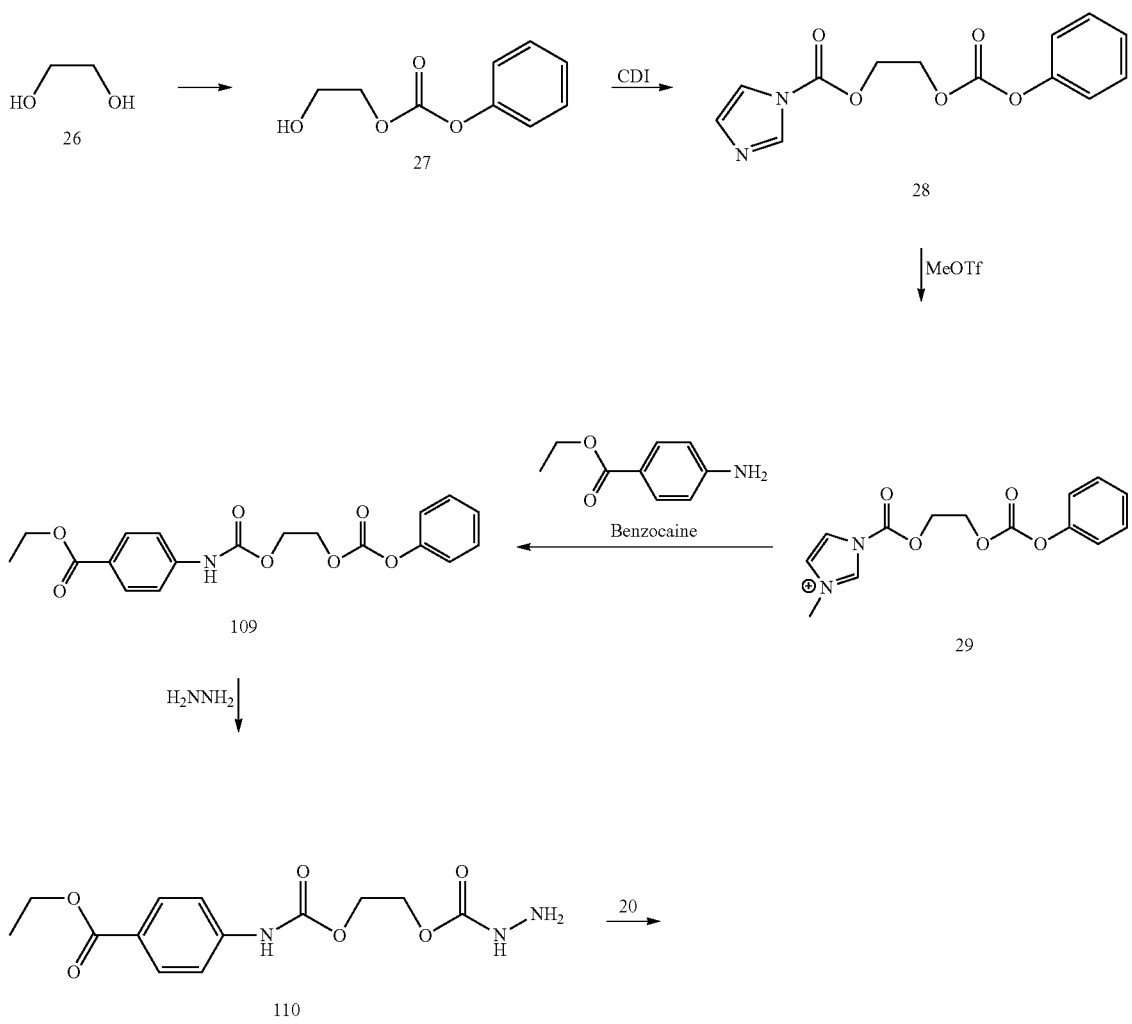

-continued

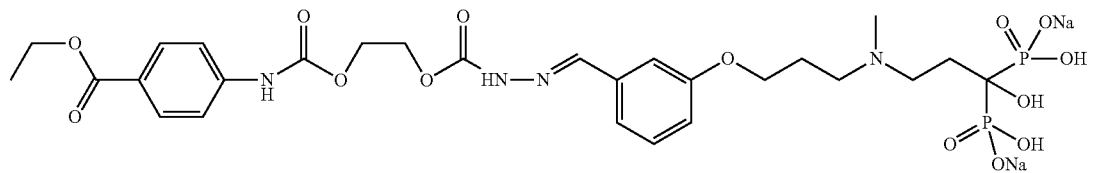

111

Compound 109:
It was prepared in the same way as compound 30 starting from compound 28 and benzocaine and was characterized.

Compound 110:
It was prepared in the same way as compound 31 starting from compound 109 and was characterized.

Compound 111:
It was prepared in the same way as compound 32 starting from compounds 110 and 20, and was characterized by its mass, 1H NMR and 31P NMR spectra.

The fluorescent analog of 3—molecule 115—bearing a dansyl residue, was synthesized according to the following reaction diagram:

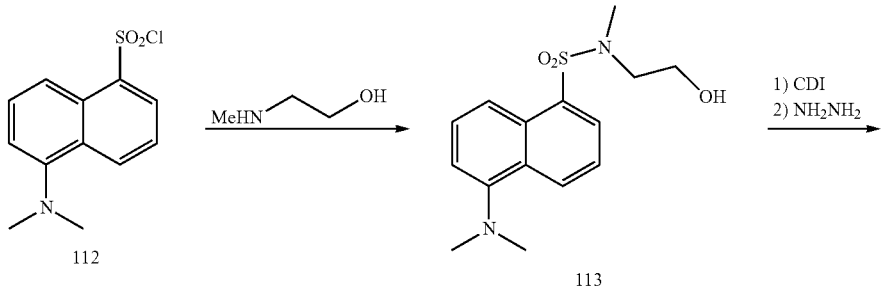

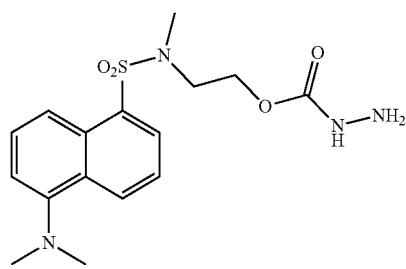

114

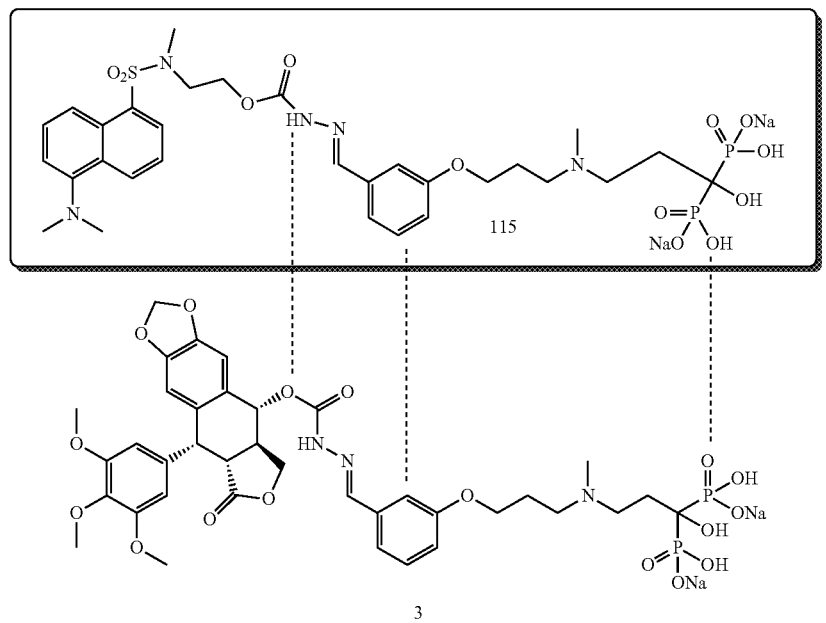

Compound 114:
It was prepared in the same way as compound 22 starting from compound 113 and was characterized.

Compound 115:
It was prepared in the same way as compound 3 starting from compounds 114 and 20, and was characterized by its mass, 1H NMR and 31P NMR spectra.

Fluorescent derivatives—molecules 124, 125, 126 and 127—bearing a dansyl residue, were synthesized according to the following reaction diagram:

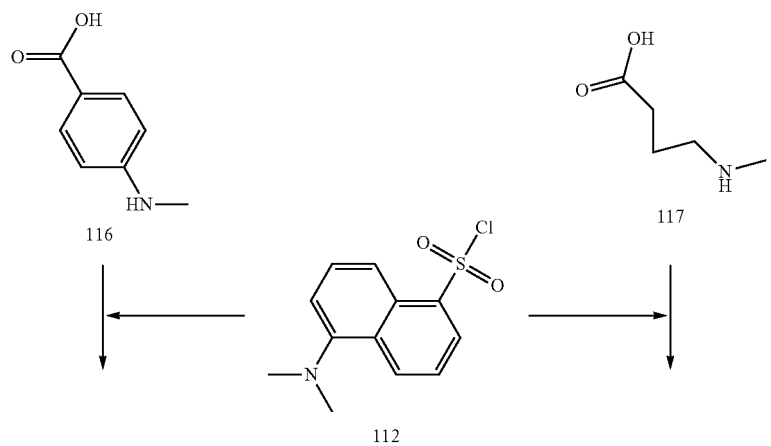

89
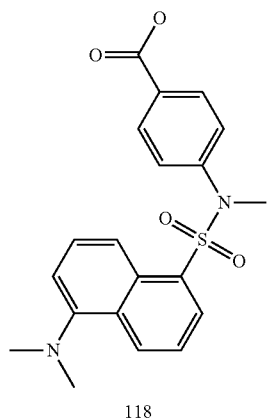
118
90
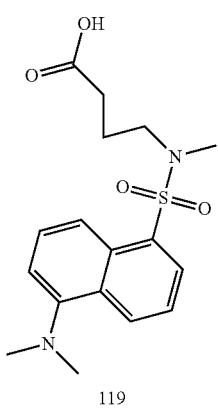
119
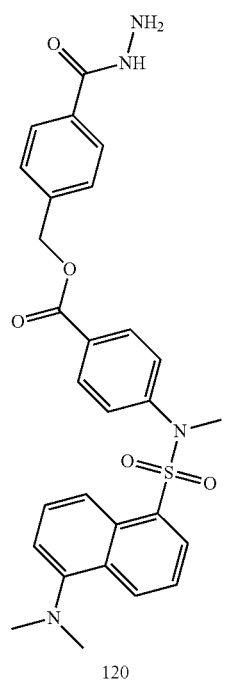
120
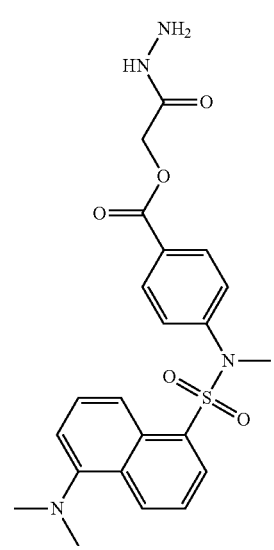
121
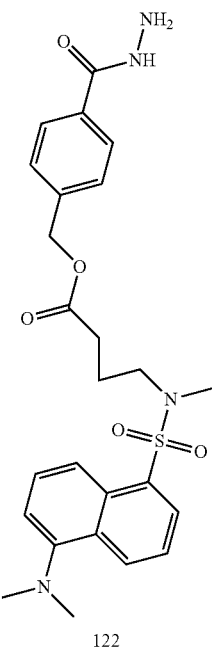
122
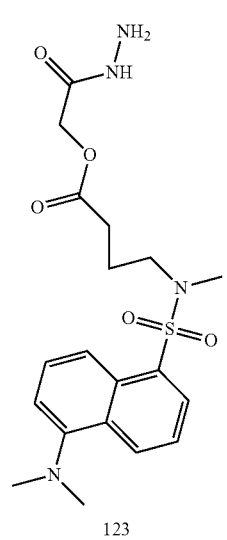
123

-continued

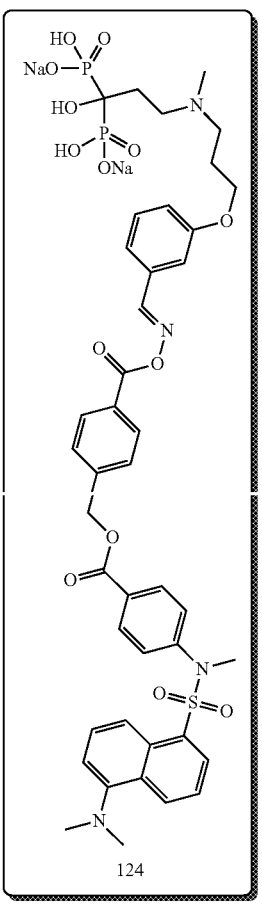

124

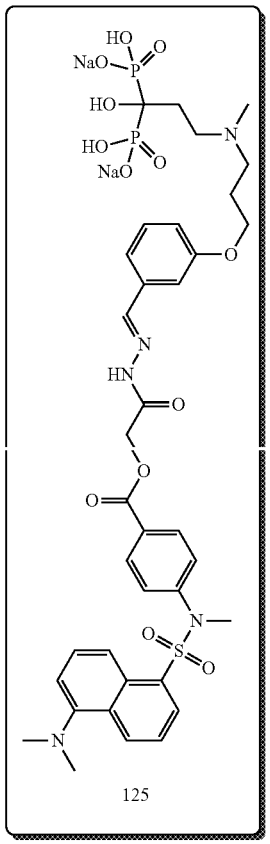

125

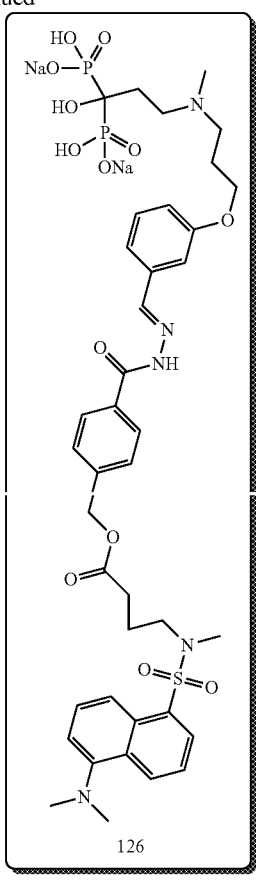

126

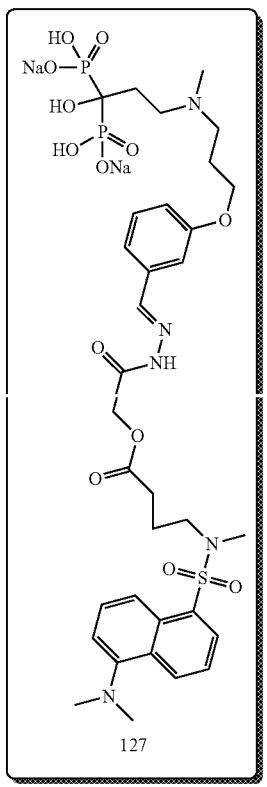

127

Compounds 120, 121, 122 and 123:
They were prepared in the same way as compound 75 starting respectively from compounds 118 119, 60 and 76 and were characterized.

Compounds 124, 125, 126 and 127:
They were prepared in the same way as compound 73, 80 and 90 starting, respectively, from compounds 120, 121, 122, 123 and 20 and were characterized by their mass, 1H NMR and 31P NMR spectra.

A fluorescent derivative—molecule 131—, bearing a dansyl residue, was synthesized according to the following reaction diagram:

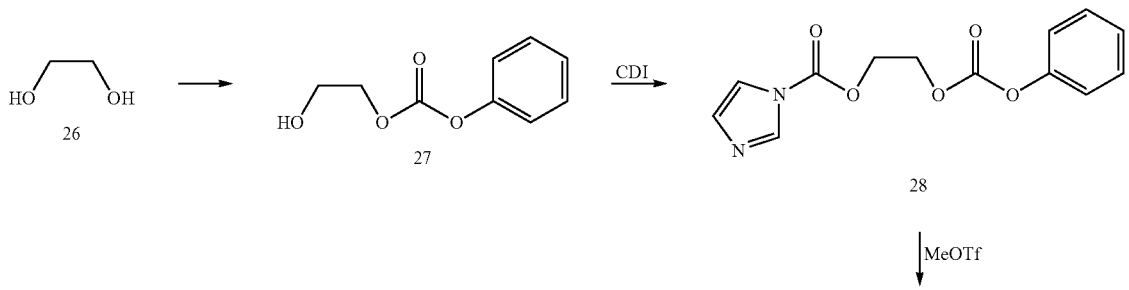

-continued

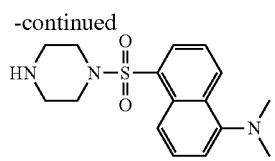
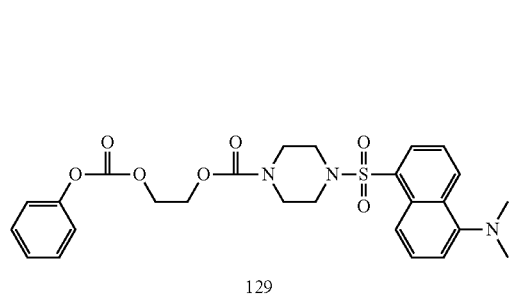
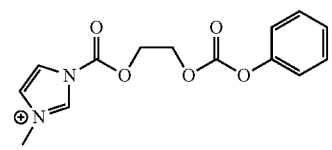

129 ← 128    29

H₂NNH₂ ↓

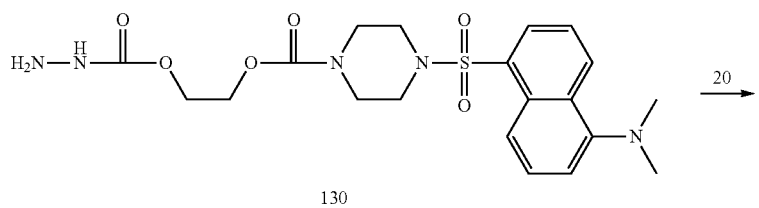

130 →20

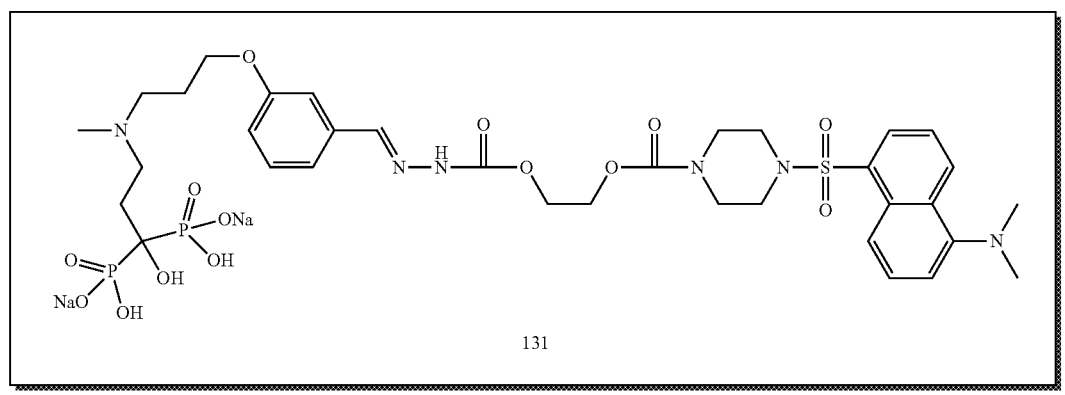

131

Compound 129:
It was prepared in the same way as compound 30 starting from commercial compounds 28 and 128 and was characterized.

Compound 130:
It was prepared in the same way as compound 31 starting from compound 129 and was characterized.

Compound 131:
It was prepared in the same way as compound 32 starting from compounds 130 and 20, and was characterized by its mass, 1H NMR and 31P NMR spectra.

2. Dissociation Test of the Compounds According to the Invention in Biological Media The dissociation of the imine $X_2$ bond and the release of the compounds of biological interest were demonstrated. To this end, fluorescent derivatives were used for better detection of dissociation products in biological media such as minced tumor preparation, physiological saline, etc.

This dissociation test was especially conducted with molecule 115 having a dansyl residue that particularly represents an analog of molecule 3, the podophyllotoxin motif being replaced by a dansyl group.

For this, compound 115 was placed in a minced tumor medium at 37° C. and HPLC was used to measure the release kinetics of compound 114 and compound 113 (see diagram below).

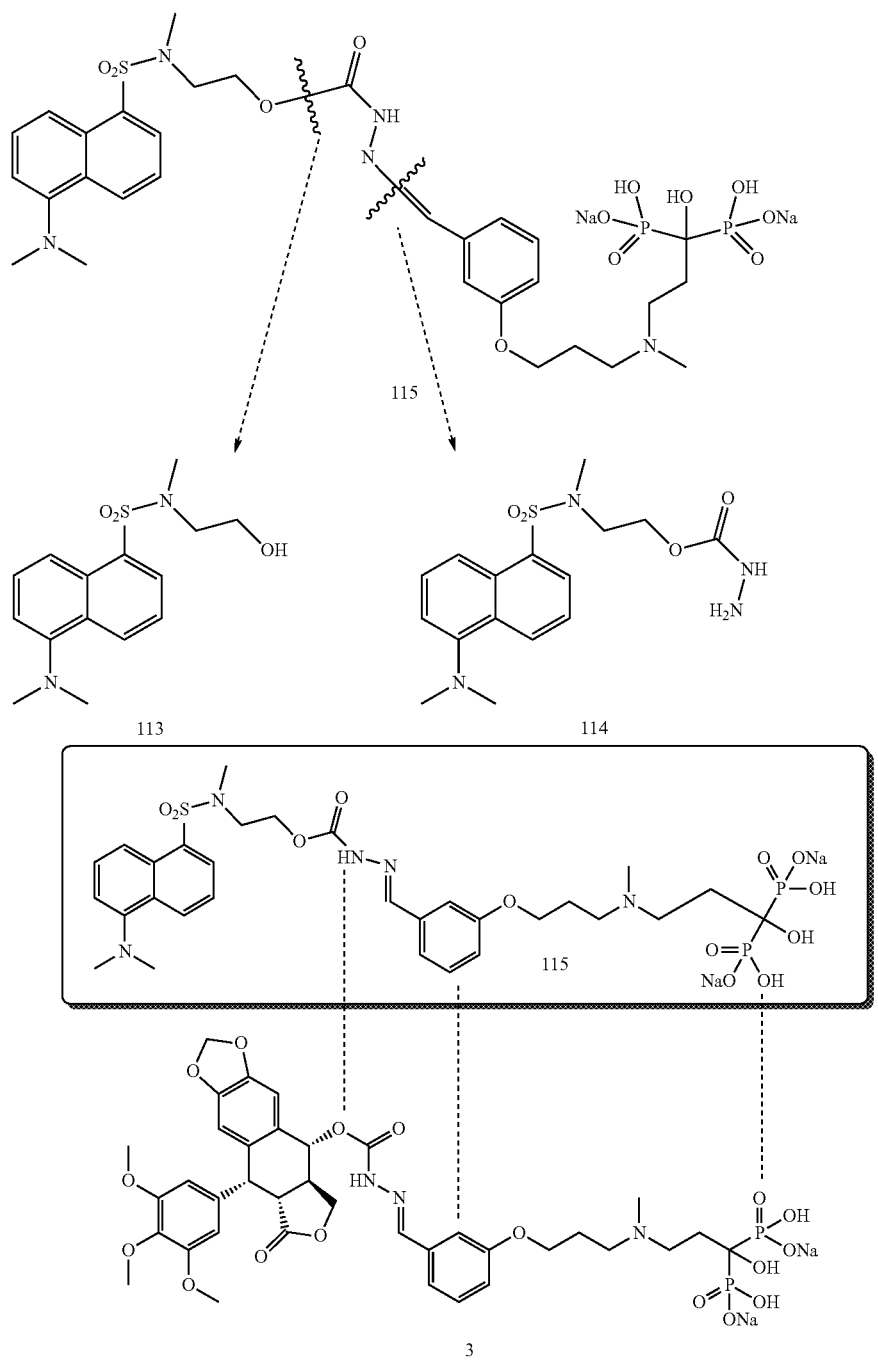

Figure 3:
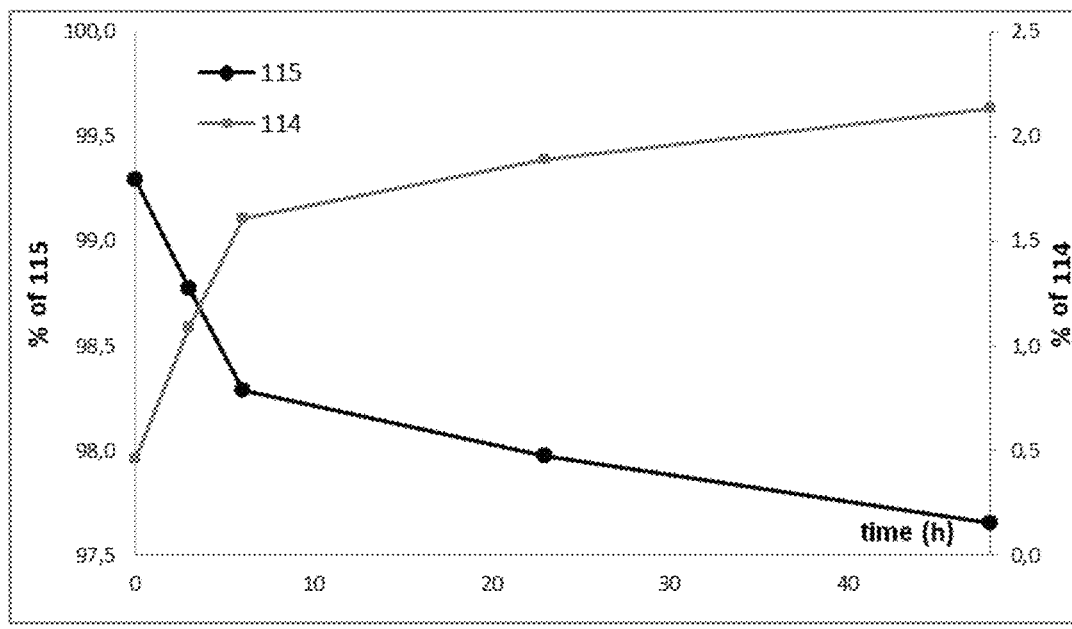
FIG. 3 shows the evolution over time of the release of molecule 114 from compound 115 according to the invention in a minced tumor preparation.

The results obtained are shown in in FIG. 3.

This dissociation test was also conducted with molecule 80. For this, compound 80 was placed in a minced tumor medium at 37° C. and HPLC was used to measure the release kinetics of methotrexate (MTX).

Figure 4:
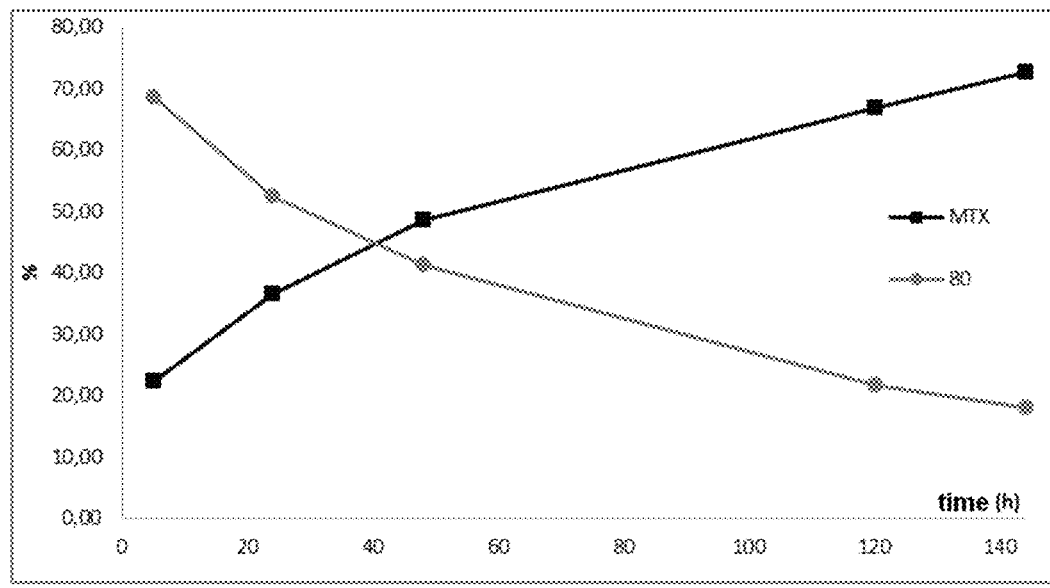
FIG. 4 shows the evolution over time of the release of methotrexate (MTX) from compound 80 according to the invention in a minced tumor preparation.

The results obtained are shown in FIG. 4.

3. Biological Tests

The results of dissociation tests of the compounds according to the invention in biological media, where the dissociation of the imine bond and the release of the compounds of biological interest was demonstrated, are in agreement with the biological activity of these compounds according to the invention.

In Vitro Study

Studies were conducted to evaluate the in vivo cytotoxic or anti-proliferative potential of the compounds according to the invention in three cell lines: two tumor lines (POS1, mouse osteosarcoma cells; SaOS$_2$, human osteosarcoma cells) and a non-tumor fibroblastic line (L929, fibroblasts of murine origin).

The mouse osteosarcoma cells (POS1) were cultured in RPMI medium (Roswell Park Memorial Institute), FCS (Fetal Calf Serum) (5%), in a humid atmosphere at 37° C. containing 5% $CO_2$.

The human osteosarcoma cells (SaOS2) were cultured in DMEM (Dulbecco's Modified Eagle Medium), FCS (Fetal Calf Serum) (10%), in a humid atmosphere at 37° C. containing 5% $CO_2$.

Fibroblasts of murine origin (L929) were cultured in RPMI medium, FCS (5%), in a humid atmosphere at 37° C. containing 5% of $CO_2$.

To conduct cytotoxicity tests, the various cell lines were inoculated (1000 cells per well) at $T_0$ in 96-well plates.

The peripheral wells were completed with 100 μl of culture medium alone. The concentrations of the compound to be tested were contacted at $T_{24}$ (24 hours after inoculation).

An XTT test (XTT kit, supplier ROCHE) was conducted after 72 h of contact of the cells with different extracts at different concentrations. A reading was performed at 4 hours on a VICTOR2, 1420 multi-label counter plate reader, PERKIN ELMER.

This test permits measuring the activity of mitochondrial dehydrogenase, an enzyme present only in living cells. This enzyme cleaves XTT, releasing crystals of orange formazan soluble in the culture medium. The staining intensity was measured by spectrophotometry.

Cytotoxicity tests were conducted for compounds 3, 41, 42, 46 and 80 solubilized in 0.5% tween 20, after 72 hours of culture in the presence of the compound to be tested (several concentrations of 0.005 μM to 100 μM).

Each concentration was evaluated in triplicate for a cell viability test. Each range of concentrations tested was prepared extemporaneously from the compound.

The results obtained are shown in in FIG. 1 for compound 3.

The cell viability test performed after 72 hours of contact between the different cell lines and compound 3 shows an anti-proliferative or cytotoxic effect on both cell lines at concentrations of 0.5 μM to 100 μM for the tumor line POS1 and the non-tumor line L929.

Figure 5:
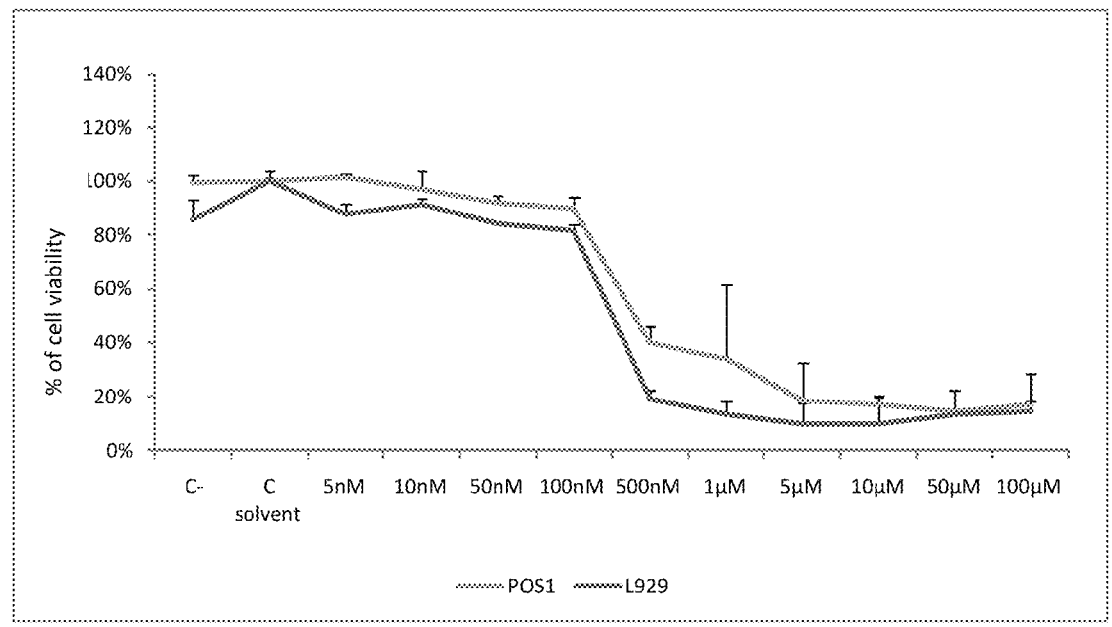
FIG. 5 shows the anticancer activity results on cell lines POS1 and L929 as a function of the concentration of compound 3.
Figure 6:
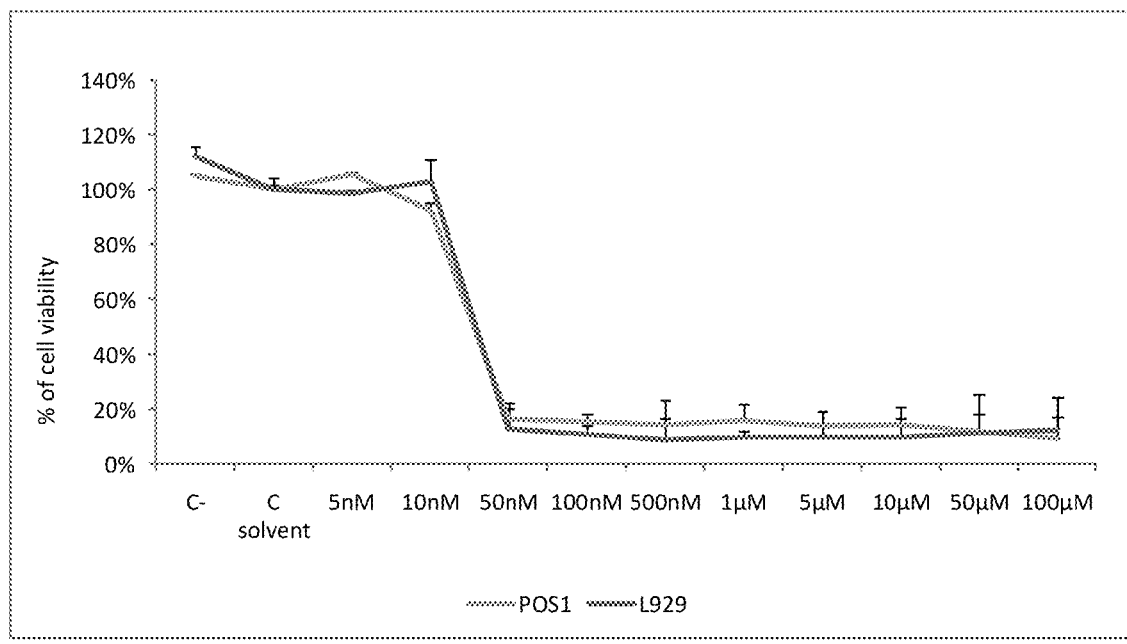
FIG. 6 shows the anticancer activity results on cell lines POS1 and L929 as a function of the concentration of compound 21.
Figure 7:
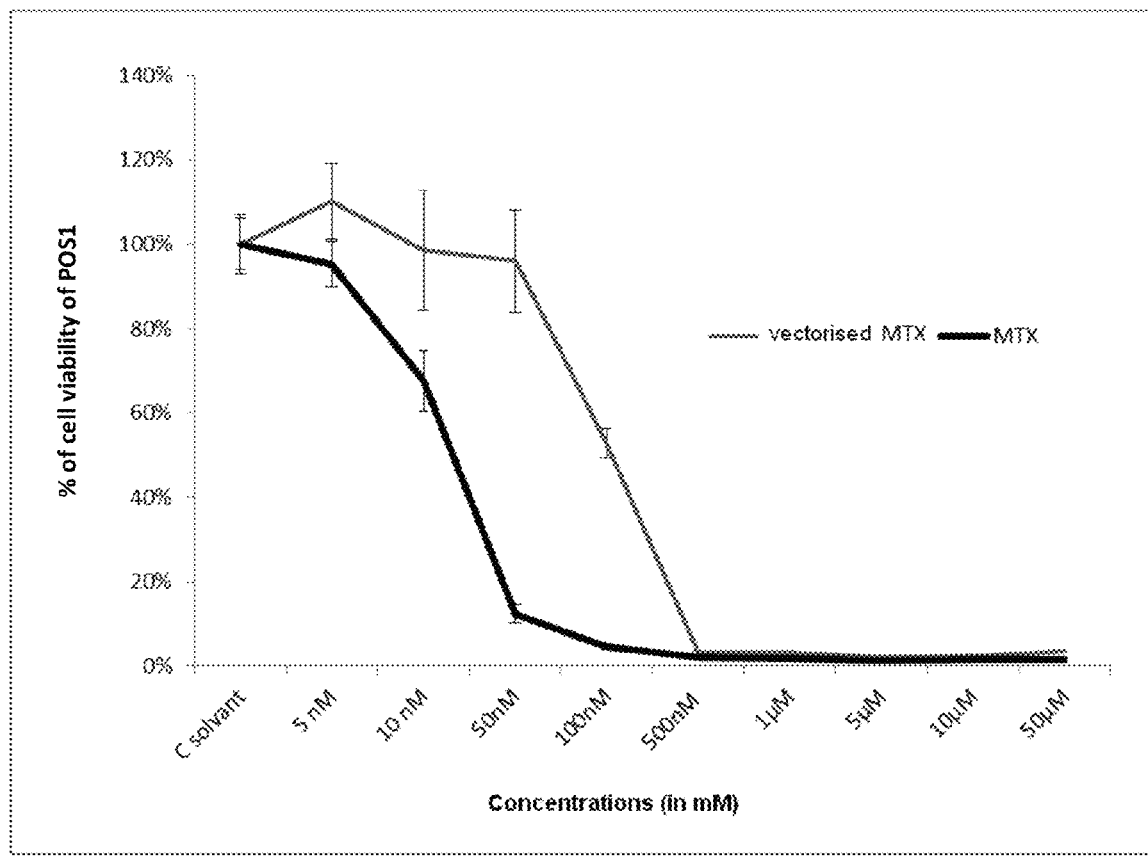
FIG. 7 shows the results of the anticancer activity results on cell lines POS1 as a function of the concentration of compound 80 (vectorized MTX) or methotrexate (MTX).
Figure 8:
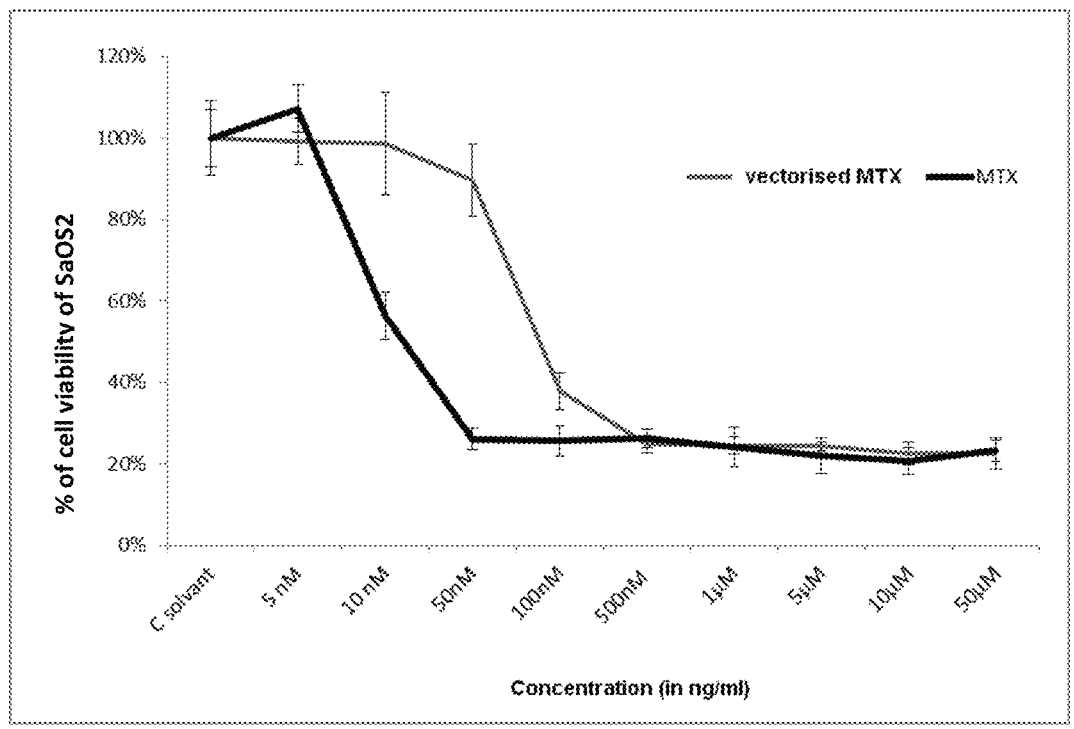
FIG. 8 shows the results of the anticancer activity results on cell lines SaOS2 as a function of the concentration of compound 80 (vectorized MTX) or methotrexate (MTX).

The results obtained on POS1 and L929 are shown in FIG. 5 for compound 3 according to the invention (vectorized podophyllotoxin) and in FIG. 6 for compound 21 (podophyllotoxin). The results obtained with compound 80 according to the invention (vectorized methotrexate) and methotrexate (MTX) are shown in FIG. 7 for POS1 and FIG. 8 for SaOS2.

For line POS1, reductions of cell viability comprised between 75% and 90% compared to the control were recorded at concentrations of 0.5 μM to 100 μM.

For line L929, reductions of cell viability comprised between 87% and 99% compared to the control were recorded at concentrations of 0.5 μM to 100 μM.

It was also observed that compounds 41, 42 and 46 induce a reduction of cell viability associated with a dose effect at concentrations of 5 μM, 10 μM, 50 μM and 100 μM for tumor line POS1, the only line tested.

The $CI_{50}$s are comprised between 1 μM and 5 μM for all the compounds tested.

Figure 9:
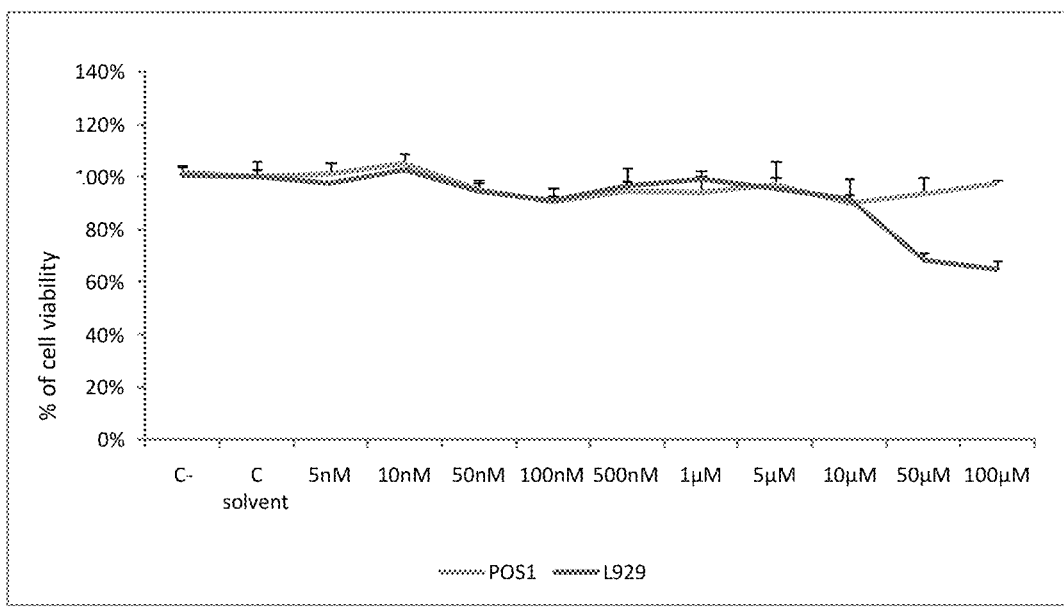
FIG. 9 shows the anticancer activity results on cell lines POS1 and L929 as a function of the concentration of compound (III) of WO 2009/083614.

It was thus demonstrated that the compounds according to the invention possess an imine bond and an $R_1$ group representing an anticancer compound residue have a biological anti-cancer activity, which is not the case for molecule (III) of patent application WO 2009/083614 or a type of bond other than the imine bond is used, as shown in FIG. 9.

molecule (III) of WO 2009/083614

In Vivo Study

Antitumor Effect of Compound 3

Molecule 3 was tested in vivo in an osteosarcoma model where murine tumor cells (POS-1) were transplanted close to the mice tibias according to a protocol described in Ory B. et al. Cancer 2005, 104(11), 2522-2529. The tumor developed around 14 days after the transplant and progressed rapidly. It may be the cause of lung metastases increasing the mortality of the animals. Molecule 3 at the concentration of 0.5 μmol/kg reduced tumor progression when the compound was administered after establishment of tumors in vivo.

Use of Compound 50 for Medical Imaging by Fluorescence

Fluorescent molecule 50 was tested for medical imaging by in vivo fluorescence on six-week old male Swiss mice. The non-vectorized ingredient 49 was tested under the same conditions, i.e. 50 μmol/kg injected (in the form of a solution in an aqueous solution of 0.9% NaCl) intraperitoneally, with a diffusion time of 120 min after injection of the molecules.

The mice also received an injection of the carrier alone (aqueous 0.9% NaCl solution) to serve as the negative control.

Figure 2A:
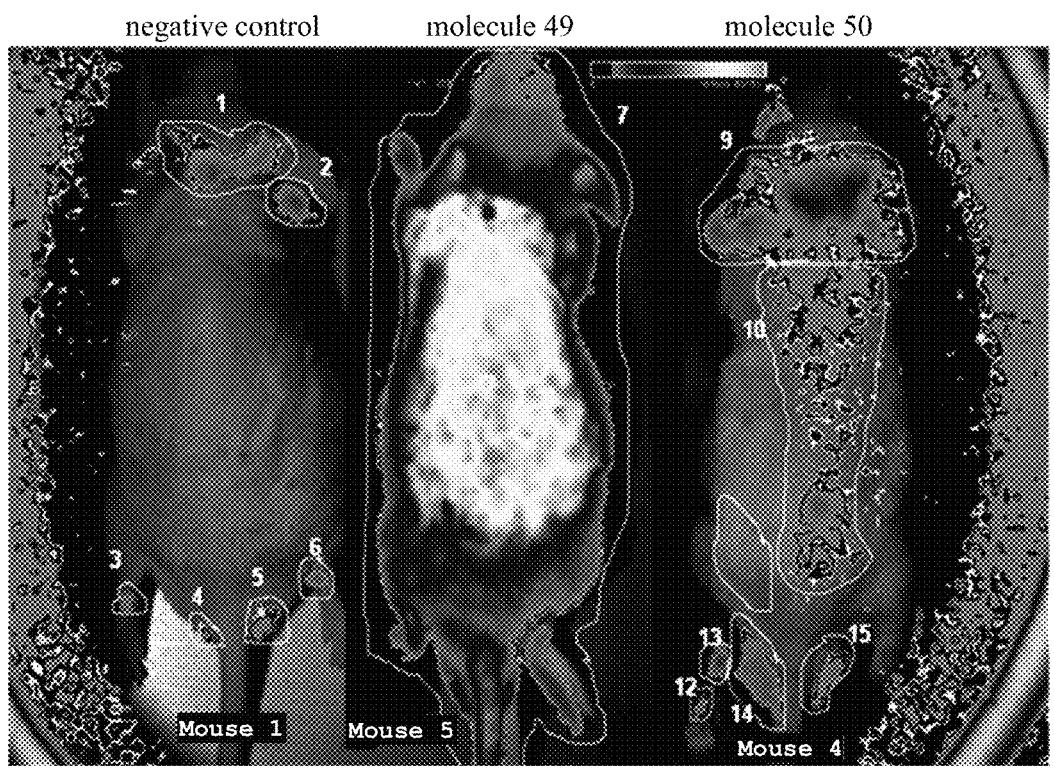
Figure 2B:
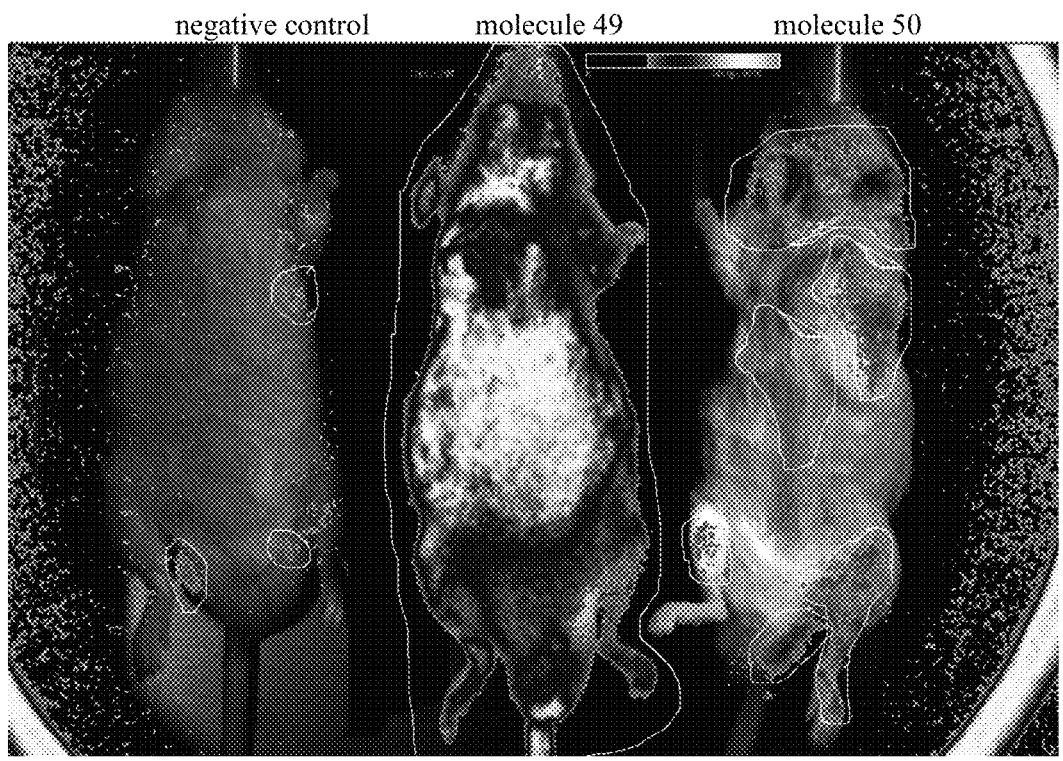

The results of the test are shown in FIGS. 2a and 2b. It clearly appears that the distribution of fluorescence for molecules 49 and 50 is different, vectorized molecule 50 giving a less widespread location of fluorescence, located in the bones.

The invention claimed is:

1. A bifunctional hydroxy-bisphosphonic acid derivative of formula (I) below:

for which:
- ---- $A_0$ represents a single bond, $A_0$ then being absent, or a =N or =$CR_0$ group, $A_0$ then representing N or $CR_0$, with $R_0$=H or ($C_1$-$C_6$)alkyl,
- $R_1$ represents a molecule of therapeutic or diagnostic interest,
- $X_1$ represents an —$X_4$-$A_1$-$(CH_2)_n$-$A_2$-$(CH_2)_m$— chain,
- $X_2$ represents an imine function (—C=N— or —N=C—),
- $X_3$ represents a single bond or a ($C_1$-$C_{20}$)alkyl chain optionally broken up and/or followed and/or replaced by one or more moieties chosen from the group consisting of aryl, heteroaryl, cycloalkyl, heterocyclic, —C≡C—, —C($R_7$)=C($R_8$)—, —O—, —S—, —$NR_9$—, —C(O)—, —C(S)—, —C=N—, —N=C—, —C≡C—, —OC(O)—, —C(O)O—, —SC(O)—, —C(O)S—, —N($R_{10}$)C(O)— and —C(O)N($R_{11}$)— groups, the aryl, heteroaryl and heterocyclic rings being optionally substituted when ==== represents a single bond, or, $X_3$ represents N, when ==== represents a double bond, $X_4$ represents a single bond or an optionally substituted aryl or heteroaryl group, $A_1$ represents a single bond, O, S, $NR_{27}$, —C(O)—, —C(S)—, —C=N—, —N=C—, —C=C—, —C≡C—, —OC(O)—, —C(O)O—, —SC(O)—, —C(O)S—, —N($R_{28}$)C(O)— or —C(O)N($R_{29}$)—, $A_2$ represents a single bond, O, S, $NR_{30}$, —C(O)—, —C(S)—, —C=N—, —N=C—, —C=C—, —C≡C—, —OC(O)—, —C(O)O—, —SC(O)—, —C(O)S—, —N($R_{31}$)C(O)—, —C(O)N($R_{32}$)—, —O—($CH_2CH_2O$)$_k$— or an —$A_9$—($CH_2$)$_a$—$A_{10}$—$CH_2$)$_b$—$A_{11}$— group, $A_9$ and $A_{11}$ each represent, independently of one another, O, S, or $NR_{38}$, $A_{10}$ represents an aryl, heteroaryl or heterocyclic group, n represents a whole number comprised between 0 and 5, m represents a whole number comprised between 0 and 5, k represents a whole number comprised between 1 and 10, a and b represent, independently of one another, a whole number comprised between 0 and 5, $R_7$ to $R_8$ represent, independently of one another, a hydrogen atom or a ($C_1$-$C_6$)alkyl group, and $R_9$ to $R_{11}$ represent, independently of one another, a hydrogen atom or a ($C_1$-$C_6$)alkyl, cycloalkyl, heterocyclic, aryl, heteroaryl or acyl group, $R_{27}$ to $R_{29}$ represent, independently of one another, a hydrogen atom or a ($C_1$-$C_6$)alkyl group, and $R_{30}$ to $R_{32}$ and $R_{38}$ represent, independently of one another, a hydrogen atom or a ($C_1$-$C_6$)alkyl, cycloalkyl, heterocyclic, aryl, heteroaryl or acyl group, or pharmaceutically-acceptable salts thereof wherein the molecules of diagnostic interest is chosen from fluorescent molecules, luminescent molecules and the molecules of therapeutic interest is chosen from anticancer agents, anti-inflammatories, antibiotics, antibacterial agents, anesthetics, and steroids.

2. The bifunctional hydroxy-bisphosphonic acid derivative according to claim 1, wherein $X_4$ represents a phenyl, naphthyl or indolyl group optionally substituted by one or more groups chosen from a group consisting of a halogen atom, $NO_2$, —CN, —OH, —SH, —$NR_{12}R_{13}$, —B(OH)$_2$, —$SO_3R_{14}$, —$COOR_{15}$, —C(O)$ONR_{16}R_{17}$, —OPH(O)$OR_{18}$, —PH(O)$OR_{19}$, —OP(O)($OR_{20}$)($OR_{21}$), —P(O)($OR_{22}$)($OR_{23}$), —C(O)$R_{24}$, —$PR_{25}R_{26}$, ($C_1$-$C_6$)alkyl and ($C_1$-$C_6$)alkoxy, with $R_{12}$ to $R_{24}$ representing, independently of one another, a hydrogen atom or a ($C_1$-$C_6$)alkyl group and $R_{25}$ and $R_{26}$ representing, independently of one another, a ($C_1$-$C_6$)alkyl group.

3. The bifunctional hydroxy-bisphosphonic acid derivative according to claim 1, wherein $A_1$ represents a single bond, O, S or $NR_{27}$.

4. The bifunctional hydroxy-bisphosphonic acid derivative according to claim 1, wherein $A_2$ represents O, S, $NR_{30}$ or —O—($CH_2CH_2O$)$_k$—.

5. The bifunctional hydroxy-bisphosphonic acid derivative according to claim 1, wherein $X_3$ represents a -$A_3$-, -$A_3$-$A_4$-$A_5$- or -$A_3$-$A_4$-$A_5$-$A_{12}$-$A_{13}$- group, with:

$A_3$ representing a single bond, O, S, $NR_{33}$, —$X_5$—C(=$X_6$)—$X_7$—, —$X_5$—$CH_2$—$X_7$— or

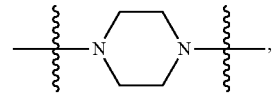

$A_4$ and $A_{12}$ representing, independently of one another, a ($C_1$-$C_6$)alkyl, aryl, ($C_1$-$C_6$)alkyl-aryl or aryl-($C_1$-$C_6$)alkyl group, $A_5$ representing a single bond, O, S, $NR_{34}$, —$X_8$—C(=$X_9$)—$X_{10}$—, —$X_8$—$CH_2$—$X_{10}$— or

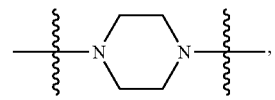

$A_{13}$ representing a single bond, O, S, $NR_{39}$, —$X_5$—C(=$X_6$)—$X_7$—, —$X_5$—$CH_2$—$X_7$— or

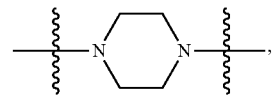

$X_5$ to $X_{10}$ representing, independently of one another, a single bond or O, S, $NR_{35}$ or

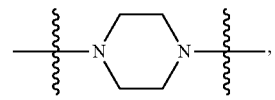

and $R_{33}$ to $R_{35}$ and $R_{39}$ representing, independently of one another, a hydrogen atom or a ($C_1$-$C_6$)alkyl group.

6. The bifunctional hydroxy-bisphosphonic acid derivatives according to claim 1, wherein $R_1$ is a active ingredient useful for the treatment or diagnosis of a osteolytic or osteocondensing bone remodeling disease.

7. The bifunctional hydroxy-bisphosphonic acid derivatives according to claim 6, wherein the osteolytic or osteocondensing bone remodeling disease is selected from primary bone tumors; bone metastases; multiple myeloma; phosphate-calcium metabolism deregulation; osteoporosis; and inflammatory diseases.

8. The bifunctional hydroxy-bisphosphonic acid derivative according to claim 1, wherein it is a compound of formula (Ia) below:

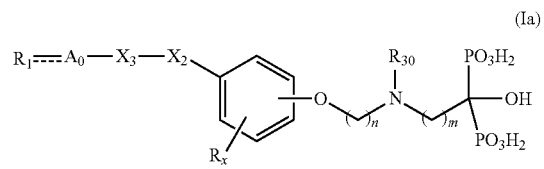

(Ia)

for which ==== $A_0$, $R_1$, $R_{30}$, $X_2$, $X_3$, n and m are as defined in claim 1 and $R_x$ represents one or more substituents of the phenyl ring chosen from the group consisting of a hydrogen atom, a halogen atom, $NO_2$, —CN, —OH, —SH, —$NR_{12}R_{13}$, —B(OH)$_2$, —$SO_3R_{14}$, —$COOR_{15}$, —C(O)

$ONR_{16}R_{17}$, $-OPH(O)OR_{18}$, $-PH(O)OR_{19}$, $-OP(O)(OR_{20})(OR_{21})$, $-P(O)(OR_{22})(OR_{23})$, $-C(O)R_{24}$, $-PR_{25}R_{26}$, $(C_1-C_6)$alkyl and $(C_1-C_6)$alkoxy, with $R_{12}$ to $R_{24}$ representing, independently of one another, a hydrogen atom or a $(C_1-C_6)$alkyl group and $R_{25}$ and $R_{26}$ representing, independently of one another, a $(C_1-C_6)$alkyl group.

9. The bifunctional hydroxy-bisphosphonic acid derivative according to claim 1, wherein it is chosen from among:

3

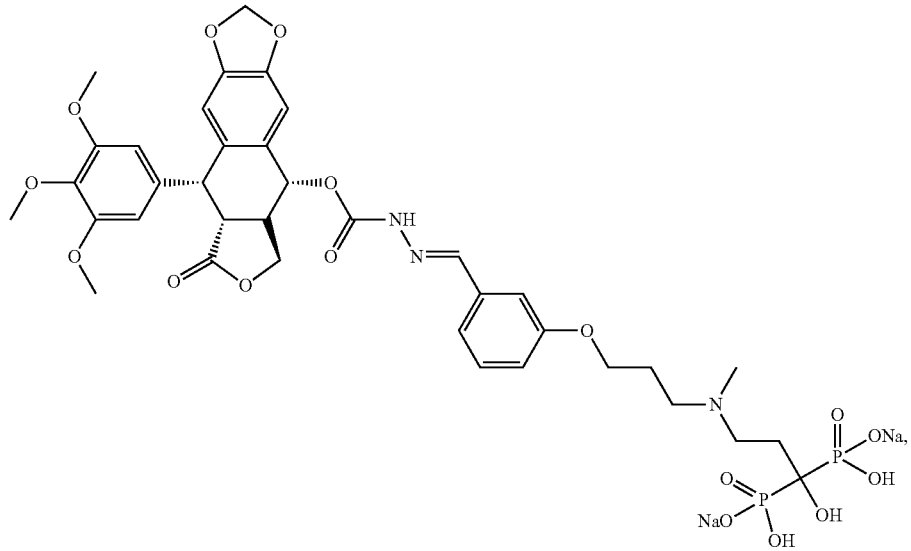

4

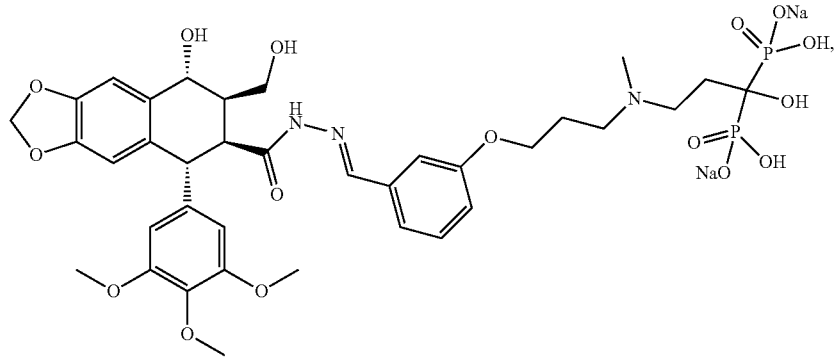

32

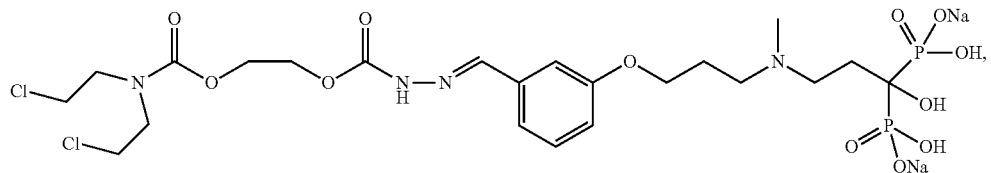

36

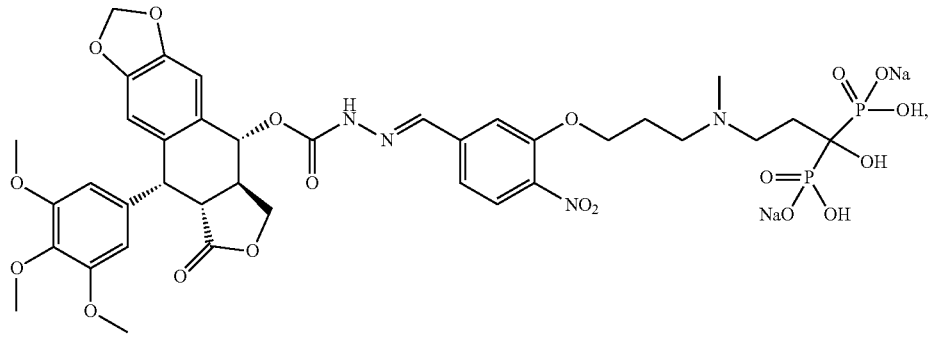

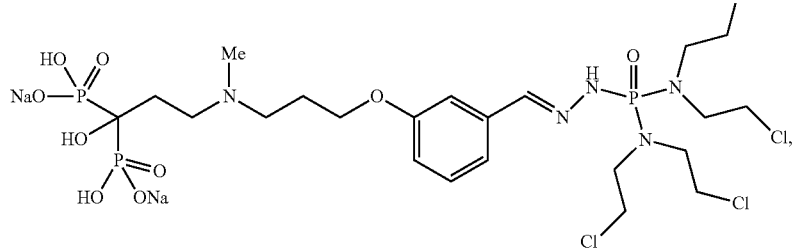
41
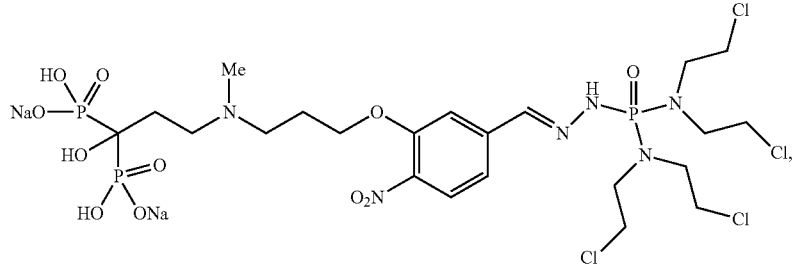
42
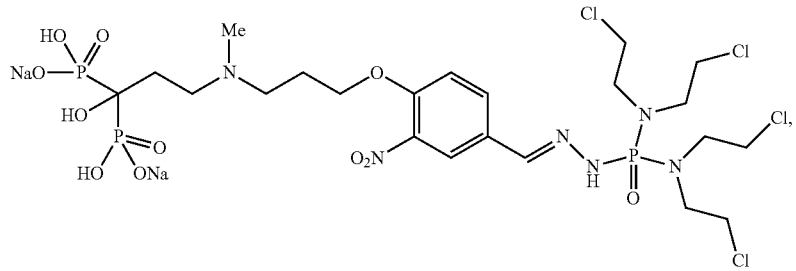
46
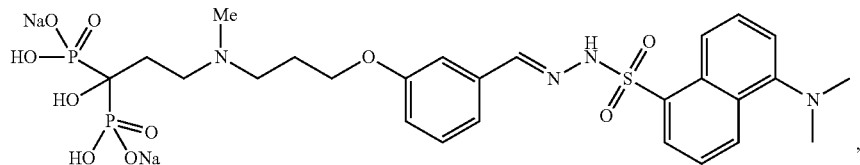
48
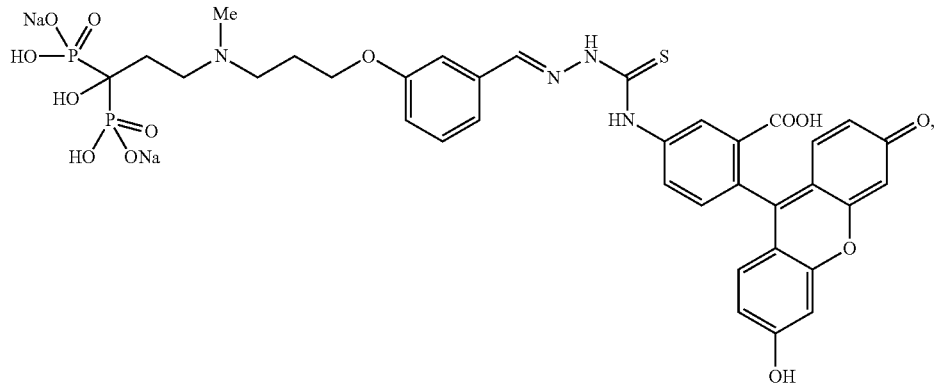
50

-continued
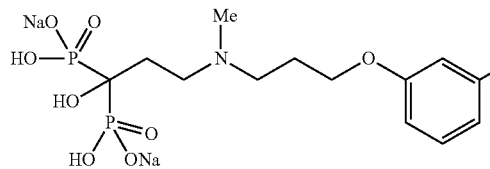 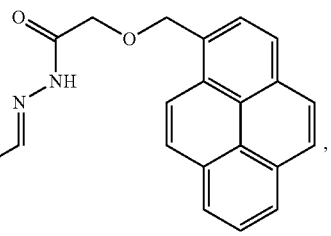 55
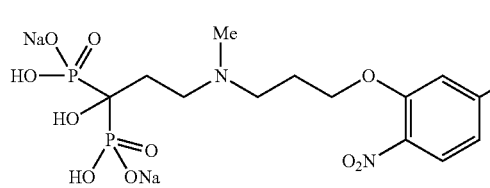 56
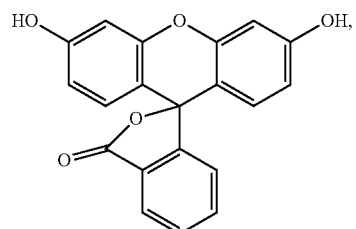 57
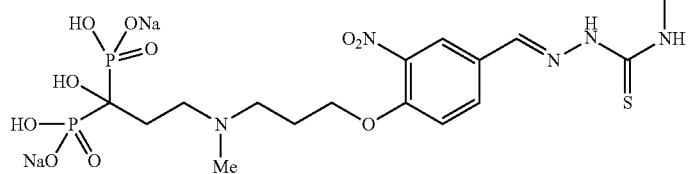 58
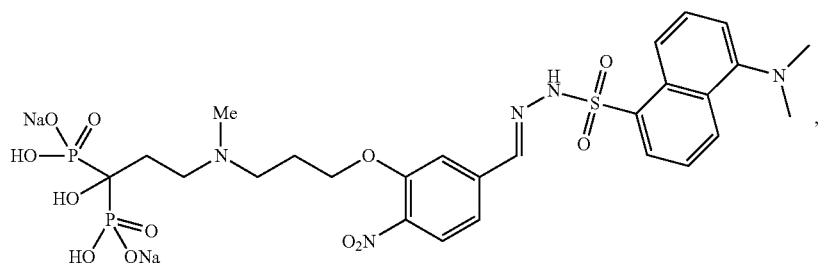 
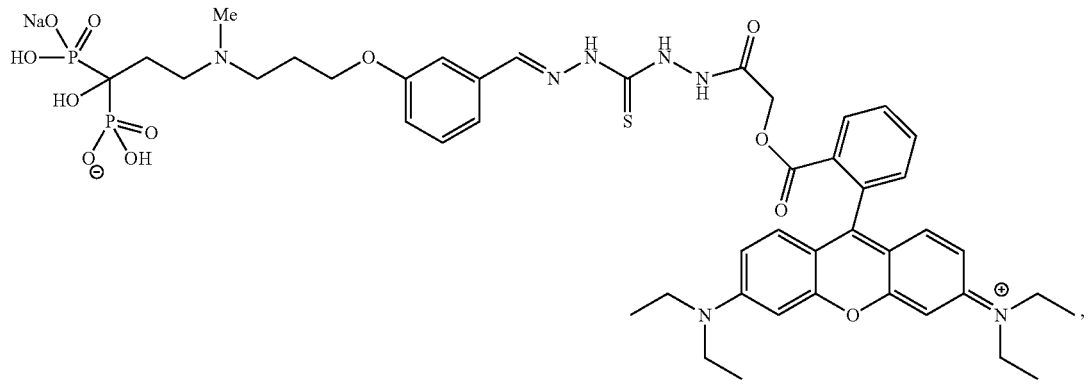 59

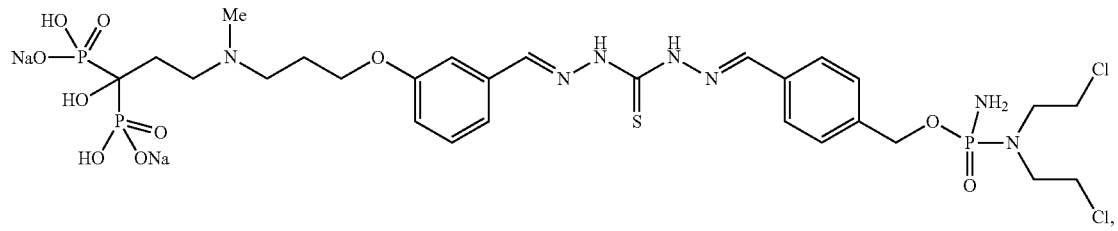
63
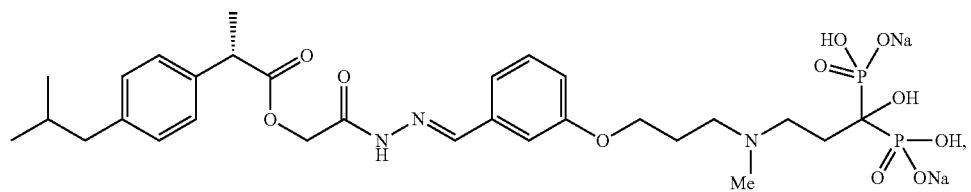
70
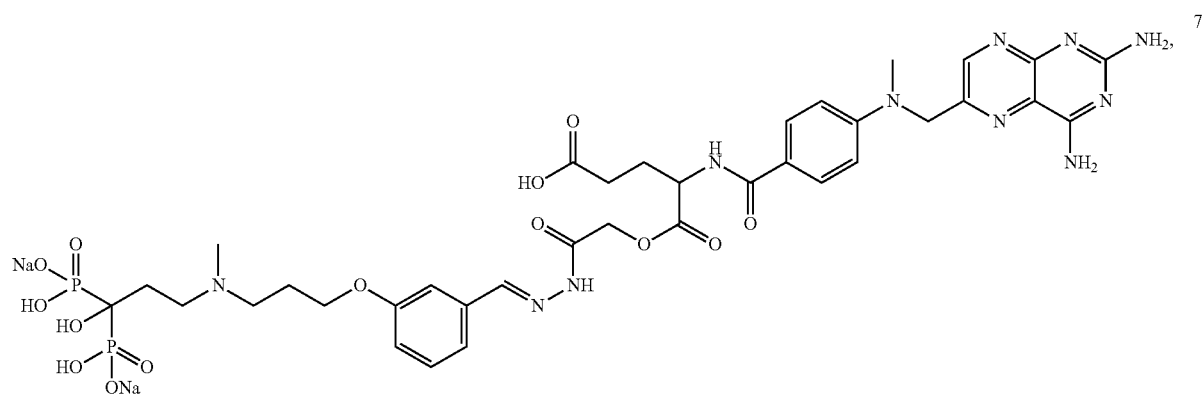
73
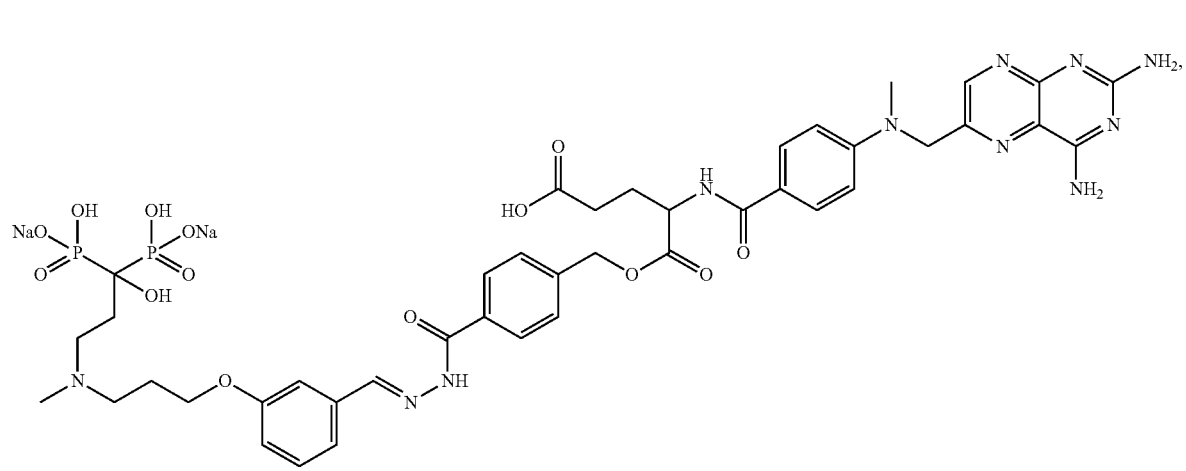
80

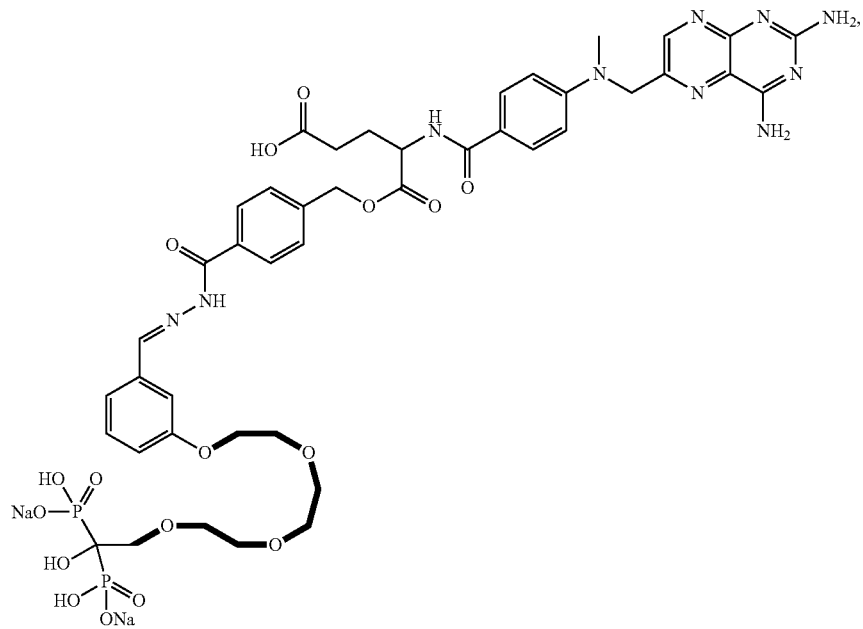
90
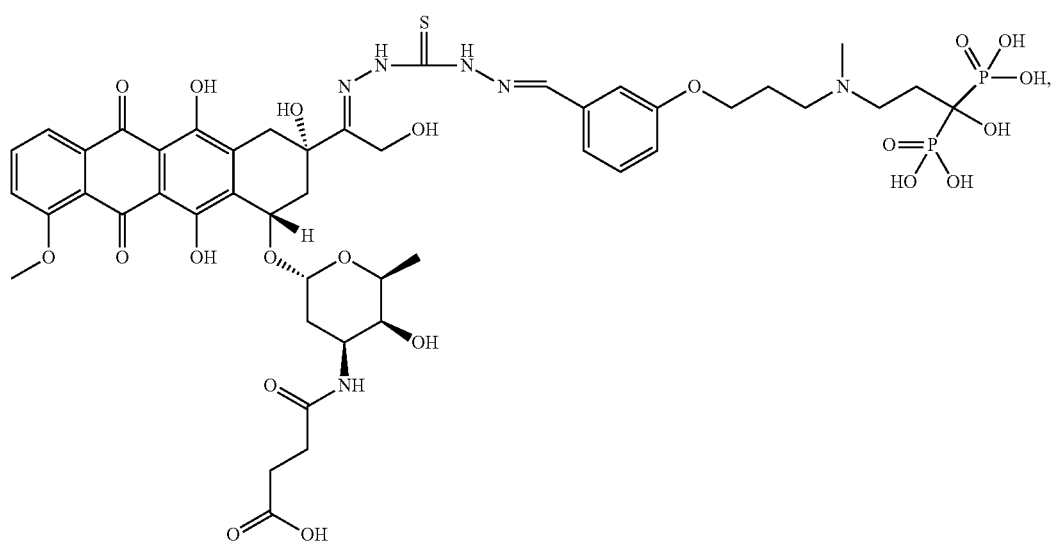
94

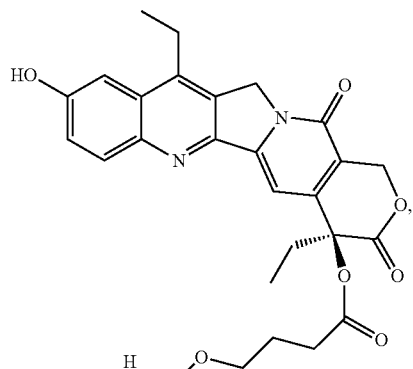
99
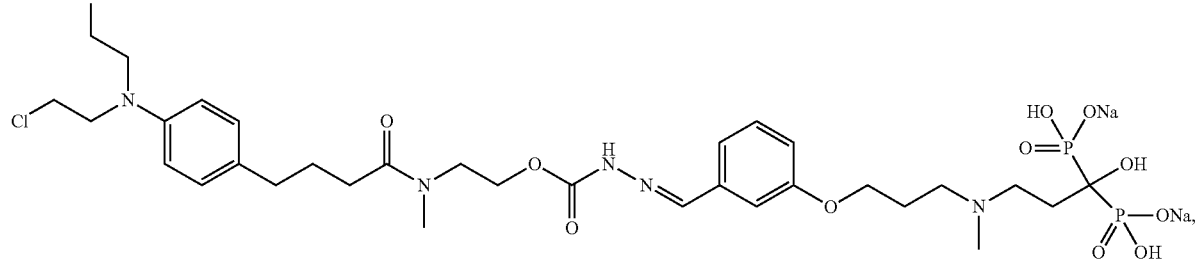
102
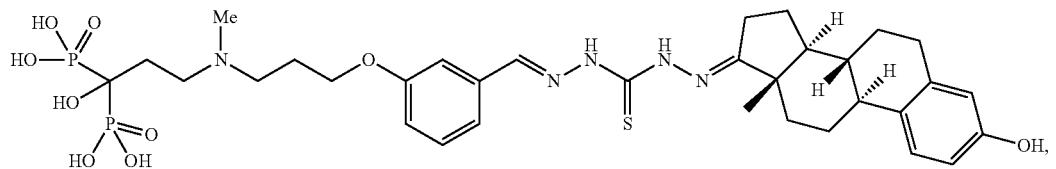
104
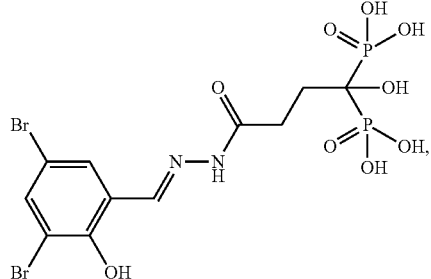
108
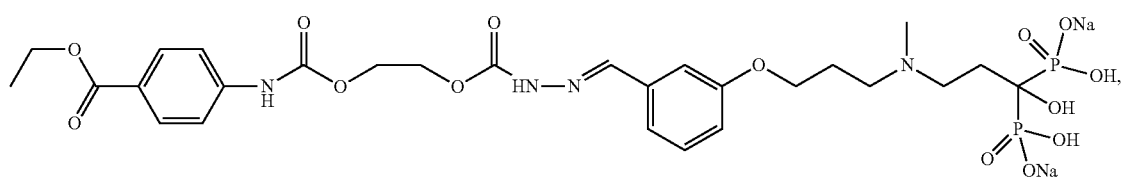
111

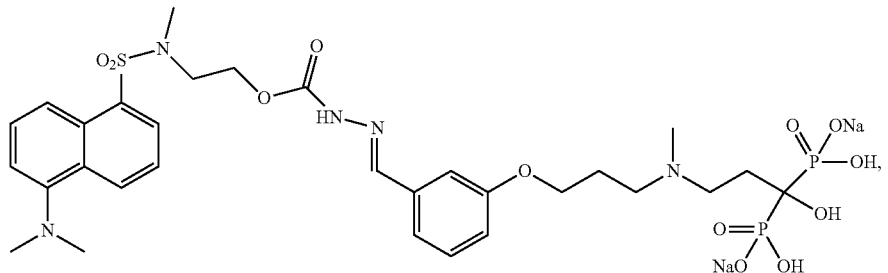
115
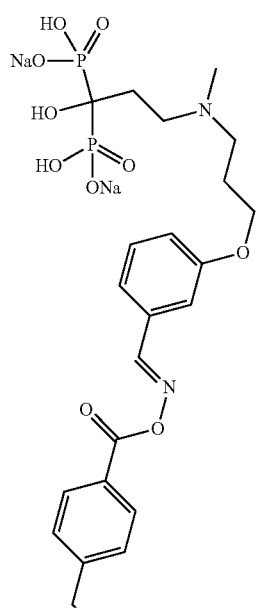
124
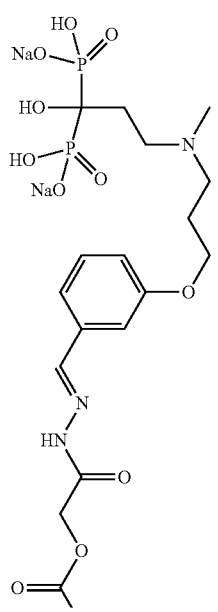
125
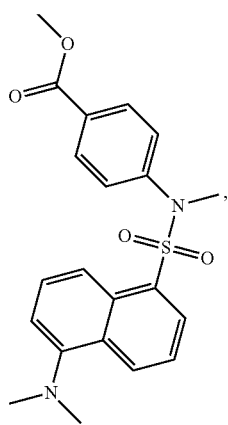
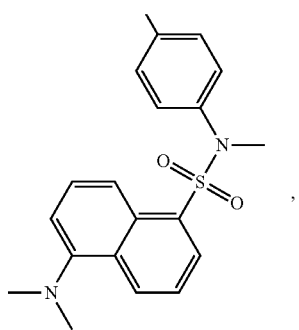

-continued
115 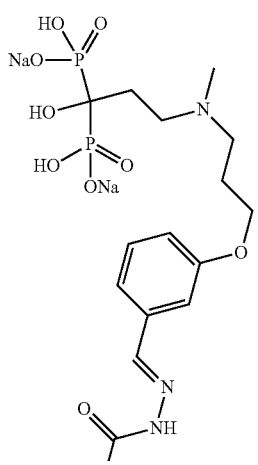
126 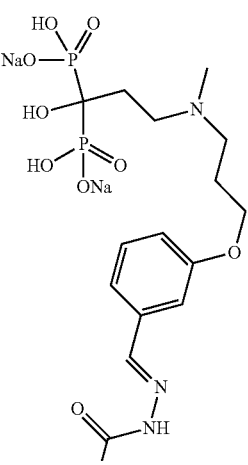
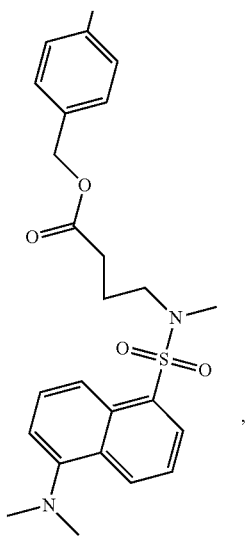,
127 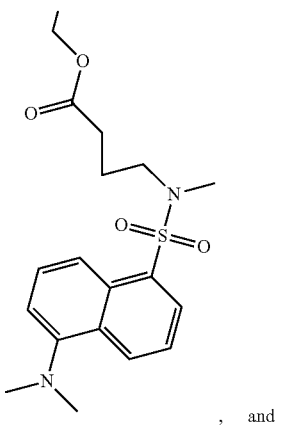, and
131 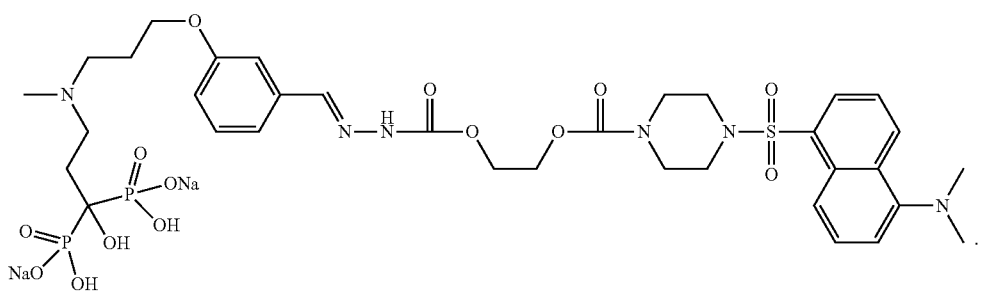

10. A pharmaceutical or diagnostic composition comprising at least one bifunctional hydroxy-bisphosphonic acid derivative according to claim 1 and at least one pharmaceutically-acceptable carrier.

11. A method for preparation of a compound of formula (I) such as defined in claim 1, comprising the successive steps below:
(a1) coupling between a compound of formula (II) below:

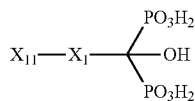

(II)

for which $X_1$ is as defined in claim 1 and $X_{11}$ represents a —CHO, or —NH$_2$ function,
with a compound of formula (III) below:

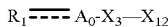

(III)

for which $\rightleftharpoons$, $A_0$, $R_1$ and $X_3$ are as defined in claim 1 and $X_{12}$ represents a —NH$_2$ function when $X_{11}$=CHO and represents a —CHO function when $X_{11}$=NH$_2$,
to give a compound of formula (I),
(b1) optionally salifying the compound of formula (I) obtained on step (a1) above to give a pharmaceutically-acceptable salt thereof, and
(c1) separation from the reaction medium of the compound of formula (I) or one of its pharmaceutically-acceptable salts obtained in step (a1) or (b1) above.

12. The bifunctional hydroxy-bisphosphonic acid derivatives according to claim 1, wherein n represents a whole number comprised between 1 and 5 and m represents a whole number comprised between 1 and 5.

13. The bifunctional hydroxy-bisphosphonic acid derivatives according to claim 1, wherein n represents 3 and m represents 2.

14. The bifunctional hydroxy-bisphosphonic acid derivative according to claim 1, wherein:
the fluorescent molecule is selected from (5-dimethylamino)naphthalene-1-sulfonyl (dansyl group), 7-nitro-1,2,3-benzoxadiazole (NBD group), a 1-pyrene carboxaldehyde, fluorescein and derivatives thereof, rhodamine and cyanine derivatives,
the luminescent molecule is selected from dioxetane derivatives and alkaline or alkaline earth sulfides,
the anticancer agent is selected from alkylating, antineoplastic molecules and topoisomerase 1 inhibitors,
the anti-inflammatory is selected from corticosteroids and nonsteroidal anti-inflammatories,
the antibiotics is spiramycin,
the antibacterial agent is selected from salicylaldehyde and derivatives thereof,
the anesthetic is benzocaine, and
the steroid is a derivative of estradiol or estrone.

15. The bifunctional hydroxy-bisphosphonic acid derivative according to claim 14, wherein the fluorescein derivative is fluorescein isothiocyanate (FITC); the rhodamine is rhodamine B; the cyanine derivative is selected from fluorescyanines and gallocyanine; the alkylating molecule is selected from nitrogen containing analogs of mustard gas, ifosfamide and derivatives thereof, and chlorambucil and derivatives thereof; the antineoplastic molecule is selected from doxorubicin, cisplatin, adriamycin, actinomycin, fluorouracil, methotrexate, etoposide, vincristine, podophyllotoxin, busulfan, docetaxel, 5-fluorouracil and derivatives thereof; the topoisomerase 1 inhibitors is selected from irinotecan and SN38; the corticosteroid is selected from dexamethasone and derivatives thereof; the nonsteroidal anti-inflammatory is selected from ibuprofen, indomethacin, bendazac, etodolac, diclofenac, lonazolac, and derivatives thereof; and the antibacterial agent is selected from salicylaldehyde and dalyde.

16. A method to treat or diagnose osteosarcoma comprising the administration to a patient in need thereof of an effective amount of a bifunctional hydroxy-bisphosphonic acid derivative according to claim 1.

17. A compound of formula (II) below:

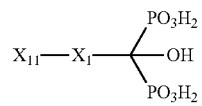

(II)

for which:
$X_{11}$ represents a —CHO, or —NH$_2$ function,
$X_1$ represents an —$X_4$-$A_1$-(CH$_2$)$_n$-$A_2$-(CH$_2$)$_m$— chain,
$X_4$ represents a single bond or an optionally substituted aryl or heteroaryl group,
$A_1$ represents a single bond, O, S, NR$_{27}$, —C(O)—, —C(S)—, —C=N—, —N=C—, —C=C—, —C≡C—, —OC(O)—, —C(O)O—, —SC(O)—, —C(O)S—, —N(R$_{28}$)C(O)— or —C(O)N(R$_{29}$)—,
$A_2$ represents a single bond, O, S, NR$_{30}$, —C(O)—, —C(S), —C=N—, —N=C—, —C=C—, —C≡C—, —OC(O)—, —C(O)O—, —SC(O)—, —C(O)S—, —N(R$_{31}$)C(O)—, —C(O)N(R$_{32}$)—, —O—(CH$_2$CH$_2$O)$_k$— or an -A$_9$—(CH$_2$)$_a$—A$_{10}$—CH$_2$)$_b$-A$_{11}$- group,
$A_9$ and $A_{11}$ each represent, independently of one another, O, S, or NR$_{38}$,
$A_{10}$ represents an aryl, heteroaryl or heterocyclic group,
n represents a whole number comprised between 0 and 5,
m represents a whole number comprised between 0 and 5,
k represents a whole number comprised between 1 and 10,
a and b represent, independently of one another, a whole number comprised between 0 and 5,
$R_{27}$ to $R_{29}$ represent, independently of one another, a hydrogen atom or a (C$_1$-C$_6$)alkyl group, and
$R_{30}$ to $R_{32}$ and $R_{38}$ represent, independently of one another, a hydrogen atom or a (C$_1$-C$_6$)alkyl, cycloalkyl, heterocyclic, aryl, heteroaryl or acyl group,
or a pharmaceutically-acceptable salt thereof.

18. The compound according to claim 17, wherein it has formula (IIa) below:

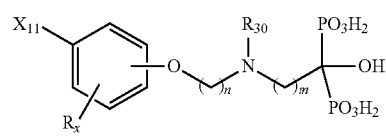

(IIa)

for which $X_{11}$, $R_{30}$, n and m are as defined in claim 17 and $R_x$ represents one or more substituents of the phenyl ring chosen from the group consisting of a hydrogen atom, a halogen atom, NO$_2$, —CN, —OH, —SH, —NR$_{12}$R$_{13}$, —B(OH)$_2$, —SO$_3$R$_{14}$, —COOR$_{15}$, —C(O)ONR$_{16}$R$_{17}$, —OPH(O)OR$_{18}$, —PH(O)OR$_{19}$, —OP(O)(OR$_{20}$)(OR$_{21}$), —P(O)(OR$_{22}$)(OR$_{23}$), —C(O)R$_{24}$, —PR$_{25}$R$_{26}$, (C$_1$-C$_6$)alkyl and (C$_1$-C$_6$)alkoxy, with R$_{12}$ to R$_{24}$ representing, independently of one another, a hydrogen atom or a (C$_1$-C$_6$)alkyl group and R$_{25}$ and R$_{26}$ representing, independently of one another, a (C$_1$-C$_6$)alkyl group.
19. The compound according to claim 17, wherein it is chosen from among:
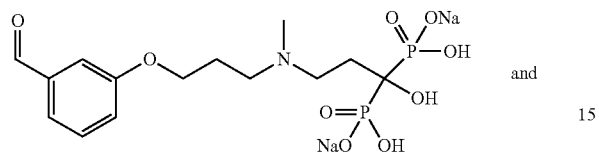
and
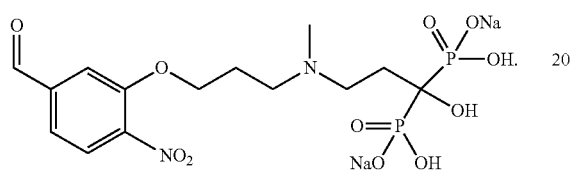
* * * * *